(12) United States Patent
Corso et al.

(10) Patent No.: US 12,709,727 B2
(45) Date of Patent: Aug. 18, 2026

(54) DEVICES AND METHODS FOR INCREASING THROUGHPUT OF FLOW-BASED ELECTROPORATION SYSTEMS

(71) Applicant: CyteQuest, Inc., Ithaca, NY (US)

(72) Inventors: Thomas N. Corso, Groton, NY (US); Harold G. Craighead, Ithaca, NY (US); Jacob Vanderburgh, Ithaca, NY (US)

(73) Assignee: CyteQuest, Inc., Ithaca, NY (US)

( * ) Notice: Subject to any disclaimer, the term of this patent is extended or adjusted under 35 U.S.C. 154(b) by 878 days.

(21) Appl. No.: 17/965,367

(22) Filed: Oct. 13, 2022

(65) Prior Publication Data

US 2023/0114435 A1 Apr. 13, 2023

Related U.S. Application Data

(60) Provisional application No. 63/399,024, filed on Aug. 18, 2022, provisional application No. 63/255,294, filed on Oct. 13, 2021.

(51) Int. Cl.

| | |
|---|---|
| ***C12M 1/42*** | (2006.01) |
| ***C12N 13/00*** | (2006.01) |
| ***C12N 15/87*** | (2006.01) |

(52) U.S. Cl.

CPC ............. *C12M 35/02* (2013.01); *C12N 13/00* (2013.01); *C12N 15/87* (2013.01)

(58) Field of Classification Search

CPC ......... C12M 35/02; C12N 13/00; C12N 15/87

See application file for complete search history.

(56) References Cited

U.S. PATENT DOCUMENTS

| | | | |
|---|---|---|---|
| 4,752,586 | A | 6/1988 | Ropars et al. |
| 5,612,207 | A | 3/1997 | Nicolau et al. |
| 6,074,605 | A | 6/2000 | Meserol et al. |
| 6,090,617 | A | 7/2000 | Meserol |
| 6,653,136 | B1 | 11/2003 | Dodgson et al. |
| 6,773,699 | B1 | 8/2004 | Soltz et al. |
| 7,131,325 | B2 | 11/2006 | Nilsson et al. |
| 7,141,425 | B2 | 11/2006 | Dzekunov et al. |

(Continued)

FOREIGN PATENT DOCUMENTS

| | | |
|---|---|---|
| CN | 101928666 B | 4/2013 |
| JP | 2006/197872 A | 8/2006 |

(Continued)

OTHER PUBLICATIONS

Burgel, Sebastian C., et al., "On-chip electroporation and impedance spectroscopy of single-cells," Sensors and Actuators B: Chemical, vol. 210, Dec. 17, 2014, pp. 82-90.

(Continued)

*Primary Examiner* — John McGuirk

(74) *Attorney, Agent, or Firm* — Merchant & Gould P.C.

(57) ABSTRACT

Disclosed are flow devices and methods for electroporation, which allow controlling the throughput of electroporation, for example by operating the electroporation process at selected throughput or operating at an increased or decreased level of throughput compared to a reference level of throughput by scaling a subset of electroporation parameters, while allowing maintaining cell viability and transfection efficiency.

17 Claims, 28 Drawing Sheets

(56) References Cited

U.S. PATENT DOCUMENTS

| | | | |
|---|---|---|---|
| 7,771,984 B2 | 8/2010 | Dzekunov et al. | |
| 8,021,867 B2 | 9/2011 | Smith et al. | |
| 8,119,381 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,143,015 B2 | 3/2012 | Smith et al. | |
| 8,143,016 B2 | 3/2012 | Smith et al. | |
| 8,148,098 B2 | 4/2012 | Smith et al. | |
| 8,163,514 B2 | 4/2012 | Smith et al. | |
| 8,222,909 B2 | 7/2012 | Ragsdale | |
| 8,304,222 B1 | 11/2012 | Smith | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 10,266,850 B2 | 4/2019 | Doudna et al. | |
| 11,225,638 B2 | 1/2022 | Corso et al. | |
| 2002/0058019 A1 | 5/2002 | Berenson et al. | |
| 2003/0044832 A1 | 3/2003 | Blankenstein | |
| 2003/0075446 A1 | 4/2003 | Culbertson et al. | |
| 2004/0106189 A1 | 6/2004 | Dodgson et al. | |
| 2006/0121446 A1 | 6/2006 | Abassi et al. | |
| 2006/0134067 A1 | 6/2006 | Liu et al. | |
| 2009/0281477 A1 | 11/2009 | Mikus et al. | |
| 2012/0190040 A1 | 7/2012 | Talebpour et al. | |
| 2012/0225424 A1 | 9/2012 | Abassi et al. | |
| 2013/0052711 A1 | 2/2013 | Chen | |
| 2014/0066836 A1 | 3/2014 | Cancedda et al. | |
| 2014/0113356 A1 | 4/2014 | Tseng et al. | |
| 2014/0170646 A1 | 6/2014 | Kelley et al. | |
| 2014/0170753 A1 | 6/2014 | Zhang | |
| 2014/0287509 A1 | 9/2014 | Sharei et al. | |
| 2015/0056705 A1 | 2/2015 | Conway | |
| 2017/0191078 A1 | 7/2017 | Zhang et al. | |
| 2017/0283761 A1 | 10/2017 | Corso | |
| 2019/0040350 A1* | 2/2019 | Chang | C12N 15/89 |
| 2019/0100774 A1* | 4/2019 | Bernate | C12M 23/44 |
| 2020/0399578 A1 | 12/2020 | Corso et al. | |
| 2021/0284948 A1 | 9/2021 | Hauwaerts et al. | |
| 2022/0056392 A1 | 2/2022 | Corso et al. | |
| 2024/0191172 A1 | 6/2024 | Corso et al. | |

FOREIGN PATENT DOCUMENTS

| | | | |
|---|---|---|---|
| KR | 100807852 B1 | 2/2008 | |
| WO | WO-2006112870 A1 * | 10/2006 | C12N 15/87 |
| WO | 2013163628 | 10/2013 | |
| WO | WO-2020/232437 A1 | 11/2020 | |

OTHER PUBLICATIONS

Chang, Lingqian, et al., "Micro-/nanoscale electroporation," Lab on a Chip, vol. 16, No. 21, Sep. 19, 2016, pp. 4047-4062.
Cho et al., "A high throughput microelectroporation device to introduce a chimeric antigen receptor to redirect the specificity of human T cells," Biomed Microdevices, 12(5):855-863 (2010).
International Search Report and Written Opinion for International Application No. PCT/US2020/033401 dated Aug. 28, 2020.
International Search Report and Written Opinion Form PCT/ISA/220, International Application No. PCT/US2017/025956, pp. 1-9, International filing Date Apr. 4, 2017, mailing date of search.
International Search Report and Written Opinion Form PCT/ISA/237, International Application No. PCT/US2017/025956, pp. 1-9, International Filing Date Apr. 4, 2017.
Lin et al., "Electroporation microchips for continuous gene transfection," Sensors and Actuators B, 79:137-143 (2001).
Supplementary European Search Report for European Applicaion No. 17779655; date of completion of search Oct. 31, 2019.
Wei et al., "A Laminar Flow Electroporation System for Efficient DNA and siRNA Delivery," Anal. Chem., vol. 83 (2011), pp. 5881-5887. (Year: 2011).
Stadtmauer et al., CRISPR-engineered T cells in patients with refractory cancer. Science (80- ). Feb. 28, 2020;367 (6481).
Stewart et al., Intracellular delivery by membrane disruption: Mechanisms, strategies, and concepts. Chem Rev. 2018;118(16):7409-531.
Sukharev et al., Electroporation and electrophoretic DNA transfer into cells. The effect of DNA interaction with electropores. Biophys J. 1992;63(5):1320-7.
Sun et al., Immunotherapy with CAR-Modified T Cells: Toxicities and Overcoming Strategies. J Immunol Res. 2018;2018:1-10.
Xu et al., NKT cells co-expressing a GD2-specific chimeric antigen receptor and IL-15 show enhanced in vivo persistence and antitumor activity against neuroblastoma Clin Cancer Res. Dec. 1, 2019; 25(23): 7126-7138. doi:10.1158/1078-0432.CCR-19-0421.
Teissie et al., Mechanisms of cell membrane electropermeabilization: A minireview of our present (lack of?) knowledge. Biochim Biophys Acta. 2005;1724:270-80.
Vormittag et al., Review: A guide to manufacturing CART cell therapies. Curr Opin Biotechnol 2018;53:164-81.
Weaver et al., Theory of electroporation: A review. Bioelectrochemistry Bioenerg. 1996;4 l: 135-60.
Wo,et al., Optimizing Electroporation Conditions for High-Efficiency mRNA Transfection of CD8 + T Cells with the Gene Pulser Xcell Electroporation System mRNA using the Gene Pulser Xcell Electroporation System and Gene Pulser Electroporation. 2020.
Aach et al. "CasFinder: Flexible algorithm for identifying specific Cas9 targets in genomes" BioRxiv (2014).
Bae et al. "Cas-OFFinder: a fast and versatile algorithm that searches for potential off-target sites of Cas9 RNA-guided endonucleases" Bioinformatics 30(10): 1473-1475 (2014).
Boissel 2015 Methods Mol Biol 1239: Assembly and Characterization of megaTALs for Hyperspecific Genome Engineering Applications; 171-196.
Boissel et al. megaTALs: a rare-cleaving nuclease architecture for therapeutic genome engineering 2014 Nucleic Acids Research 42(4):2591-2601.
Bozza et al., A nonviral, nonintegrating DNA nanovector platform for the safe, rapid, and persistent manufacture of recombinant T cells. Sci Adv. 2021;7(16):1-14.
Brody et al., Biotechnology at Low Reynolds Numbers, Center for Bioengineering, University of Washington, Seattle, Washington 98195-2141, and Department of Physics, Princeton University, Princeton, New Jersey 08544 USABiophysical Journal vol. 71 Dec. 1996 3430-3441.
Buzhor, et al. Cell-based therapy approaches: the hope for incurable diseases. Regen Med. 2014;9(5): 14-35.
Cerrano et al., The Advent of CART-Cell Therapy for Lymphoproliferative Neoplasms: Integrating Research Into Clinical Practice. Front Immunol. 2020; 11:1-25.
Certo et al. Coupling endonucleases with DNA end-processing enzymes to drive gene disruption Nature Methods (2012) 9:073-975.
Depil et al., Off-the-shelf allogeneic CAR T cells: development and challenges. vol. 19, Nature Reviews Drug Discovery. Nature Research; 2020. p. 185-99.
Eyquem et al., Targeting a CAR to the TRAC locus with CRISPR/Cas9 enhances tumour rejection. Nature 2017;543 (7643):113-7.
Gaj et al., Enhancing the Specificity of Recombinase-Mediated Genome Engineering through Dimer Interface Redesign, Journal of the American Chemical Society, vol. 136, Issue 13, Mar. 10, 2014.
Grupp et al. Chimeric Antigen Receptor-Modified T Cells for Acute Lymphoid Leukemia. N Engl J Med. 2013;368:1509-18.
Harris et al., Optimization of electroporation and other non-viral gene delivery strategies for T cells. Biotechnol Prog. 2021;37(1).
Heigwer et al. "E-CRISP: fast CRISPR target site identification" Nat. Methods 11: 122-123 (2014).
Hyder et al., WA Systematic optimization of square-wave electroporation conditions for bovine primary fibroblasts. BMC Mol Cell Biol. 2020;21: 1-8.
Hirabayashi et al., Dual Targeting CAR-T Cells with Optimal Costimulation and Metabolic Fitness enhance Antitumor Activity and Prevent Escape in Solid Tumors. Nature Cancer, 2: 904-9:18, Sep. 2021.

(56) References Cited

OTHER PUBLICATIONS

Jin et al., The hyperactive Sleeping Beauty transposase SB100X improves the genetic modification of T cells to express a chimeric antigen receptor. Gene Ther. Sep. 18, 2011:849-56.
Kanduser et al.,Mechanisms involved in gene electrotransfer using high- and low-voltage pulses—An in vitro study. Bioelectrochemistry. 2009;74(2):265-71.
Klinchinsky et al. Human chimric antigen receipt macrophage for cancer immunotherapy, Nat Biotechnol Aug. 2020;38(8): 947-953. doi: 10.1038/s41587-020-0462-y.
Kotnik et al., Role of pulse shape in cell membrane electropermeabilization. Biochim Biophys Acta—Biomembr.2003;1614(2): 193-200.
Kotowski et., CRISPR-Based Editing Techniques for Genetic Manipulation of Primary T Cells. methods Protoc. 2020;3(79).
Qi et al., Repurposing CRISPR as an RNA-Guided Platform for Sequence-Specific Control of Gene Expression.
LeCong et al., Multiplex Genome Engineering Using CRISPR/Cas Systems, Science. Feb. 15, 2013; 339(6121):819-823. doi:l0.1126/science.1231143.
Lee et al., A Microscale electroporation: challenges and perspectives for clinical applications. Integr Biol. 2009; 1(3):242-51.
Lee et al., Nonendocytic delivery of functional engineered nanoparticles into the cytoplasm of live cells using a novel, high-throughput microfluidic device. Nano Lett. 2012;12(12):6322-7.
Lesueur et al., Overcoming the Specific Toxicity of Large Plasmids: Electrotransfer in Primary Cells in Vitro. Mol Ther—Nucleic Acids [Internet]. 2016;5(Dec. 2015):e291.
Levine et al., Global Manufacturing of CART Cell Therapy. Mol Tuer—Methods Clin Dev. Mar. 4, 2017:92-101.
Li et al., Highly efficient, large volume flow electroporation. Technol Cancer Res Treat. 2002;1(5):341-9.
Lissandrello et al., High-throughput continuous-flow microfluidic electroporation of mRNA into primary human T cells for applications in cellular therapy manufacturing. Sci Rep. 2020; 10: 1-16.
Liu et al., Novel T cells with improved in vivo anti-tumor activity generated by RNA electroporation. Protein Cell. 2017;8(7):514-26.
Loo et al., Microfluidic transfection of mRNA into human primary lymphocytes and hematopoietic stem and progenitor cells using ultra-fast physical deformations. Sci Rep [Internet]. 2021;1 l(l): 1-11.
Maus et al., Adoptive Immunotherapy for Cancer or Viruses. Annu Rev Immunol. 2014;32: 189-225.
Morita et al., Enhanced Expression of Anti-CD19 Chimeric Antigen Receptor in piggyBac Transposon-Engineered T Cells. Mol Ther—Methods Clin Dev [Internet]. 2018;8: 131-40.
Mount, et al., Cell-based therapy technology classifications and translational challenges. Philos Trans B. 2015;370.
Naito et al., CRISPRdirect: software for designing CRISPR/ Cas guide RNA with reduced off-target sites, Bioinformatics, 31(71, 2015, 1120-1123 doi: 10.1093/bioinformatics/btu743, Advance Access Publication Date: Nov. 20, 2014.
Osborn et al., Evaluation ofTCR gene editing achieved by TALENs, CRISPR/Cas9, and megaTAL nucleases. Mol Tuer 2016;24(3):570-81.
Porro et al., Promoterless gene targeting without nucleases rescues lethality of a Crigler-Najjar syndrome mouse model, EMBO Molecular Medicine, (2017).
Porter et al., Chimeric Antigen Receptor-Modified T Cells in Chronic Lymphoid Leukemia. N Engl J Med. 2011;365:725-33.
Prommersberger et al., Caramba: a first-in-human clinical trial with SLAMF7 Car-T cells prepared by virus-free Sleeping Beauty gene transfer to treat multiple myeloma. Gene Tuer. 2021 ;28(9):560-71.
Rafiq et al., RJ. Engineering strategies to overcome the current roadblocks in CART cell therapy. Nat Rev Clin Oncol Mar. 17, 2020: 147-67.
Ran et al., Double Nicking by RNA-Guided CRISPR Cas9 for Enhanced Genome Editing Specificity, Cell 154, 1380-1389, Sep. 12, 2013.
Razeghian et al., A deep insight into CRISPR/Cas9 application in CAR-T cell-based tumor immunotherapies. Stem Cell Res Ther. 2021;12(1): 1-17.
Roth, et al. Reprogramming human T cell function and specificity with non-viral genome targeting. Nature 2018;559:405-9.
Sather et al., Efficient modification of CCR5 in primary human hematopoietic cells using a megaTAL nuclease and AAV donor template, Science TranslationalMedicine.org Sep. 30, 2015 vol. 7 Issue 307 307ra156.
Schober et al., Orthotopic replacement of T-cell receptor a- and b-chains with preservation of near-physiological T-cell function. Nat Biomed Eng 2019;3:974-84.
Sharei et al., A vector-free microfluidic platform for intracellular delivery. Proc Natl Acad Sci US A 2013;110(6):2082-7.
Sido et al., Electro-mechanical transfection for non-viral primary immune cell engineering. bioRxiv. 2021;2021.10.26.465897.
Somerville et al. ,Clinical scale rapid expansion of lymphocytes for adoptive cell transfer therapy in the WA VE bioreactor. J Transl Med. 2012;10(1):69.
Spiegel et al., Car T cells with dual targeting of CD19 and CD22 in adult patients with recurrent or refractory B cell malignancies: a phase 1 trial, Nature Medicine, vol. 27, Aug. 2021, 1419-1431.

* cited by examiner

Fig. 1A
Side View Schematic
Inlet
Electrode
Electrode
Outlet
Channel height: 50 – 100 μm
Fig. 1B
Top View Schematic
Flow direction
Inlet
Electrodes
Outlet
Channel width: 1 – 100 mm
Fig. 1C
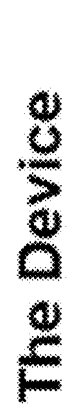
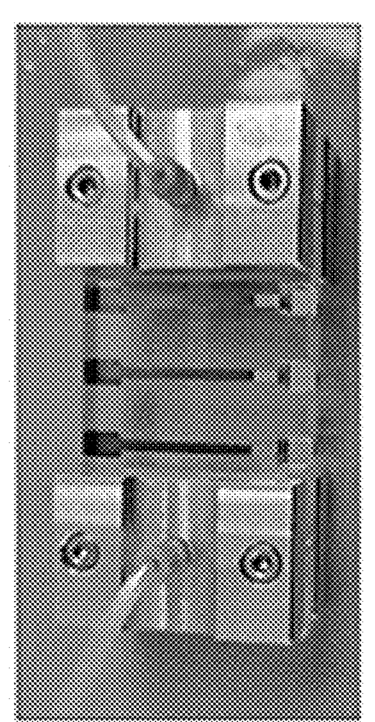
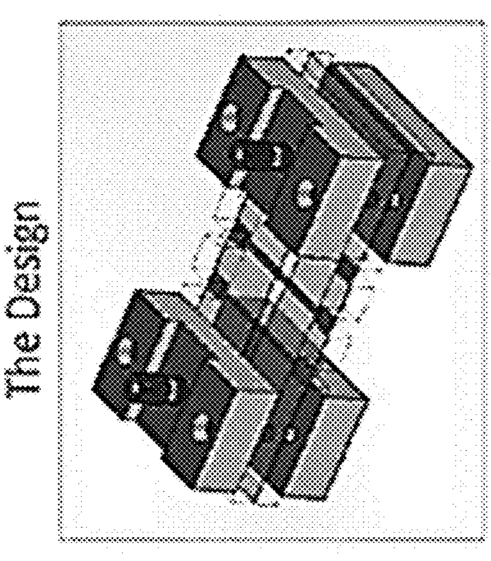

Fig. 1D

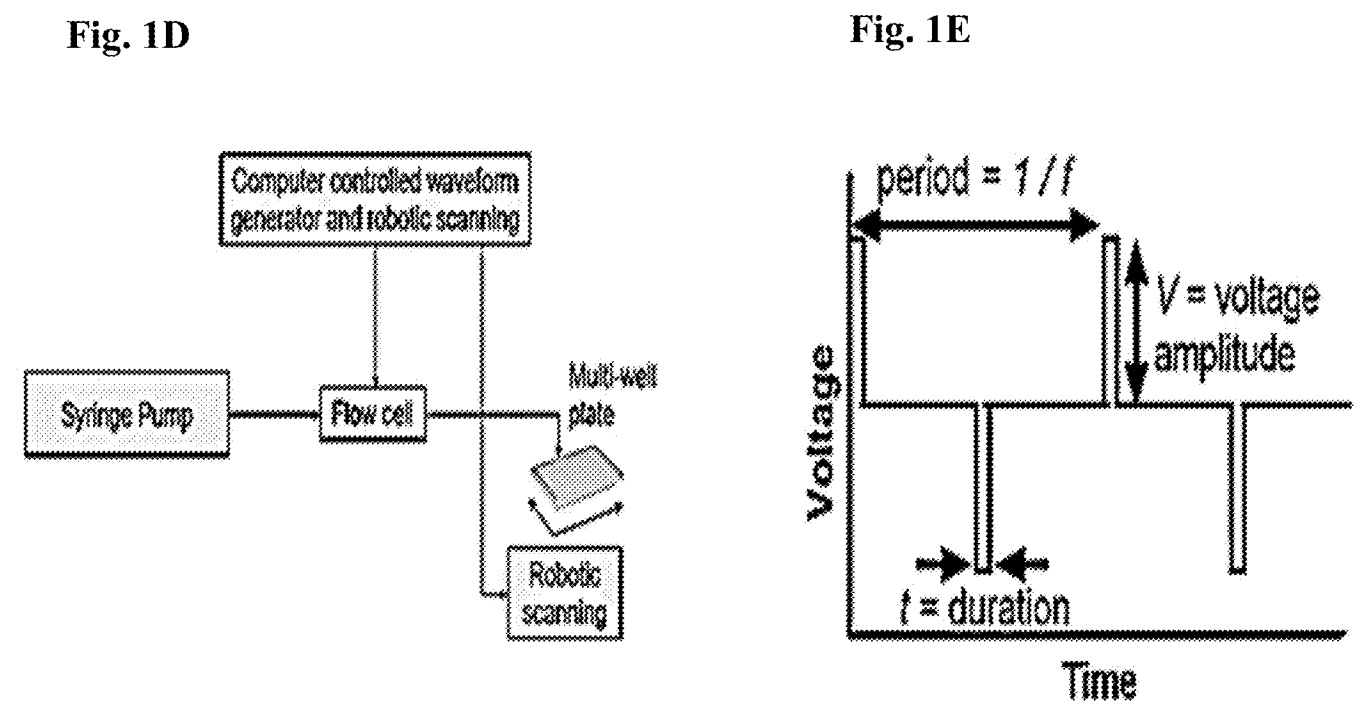

Computer controlled waveform generator and robotic scanning
Flow cell
Syringe Pump
Multi-well plate
Robotic scanning

Fig. 1E period = 1 / f
V = voltage amplitude
t = duration
Time
Voltage

Jurkat control cells

Cell morphology

Viability

GFP

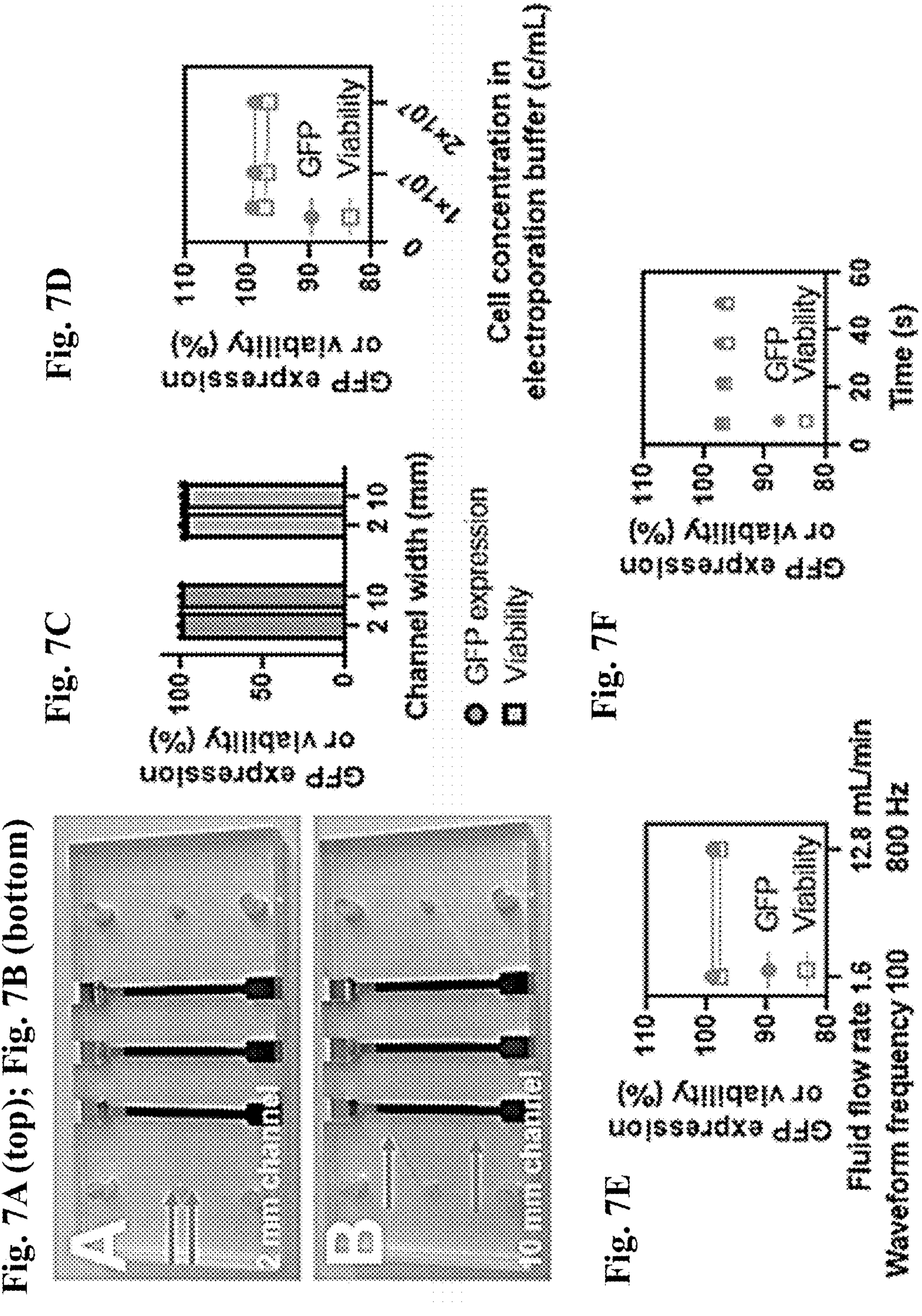

Fig. 7A (top); Fig. 7B (bottom)
A
2 mm channel
B
10 mm channel
Fig. 7C
GFP expression or viability (%)
100
50
0
2 10
2 10
Channel width (mm)
GFP expression
Viability
Fig. 7D
GFP expression or viability (%)
110
100
90
80
0
1×10⁷
2×10⁷
GFP
Viability
Cell concentration in electroporation buffer (c/mL)
Fig. 7E
GFP expression or viability (%)
110
100
90
80
GFP
Viability
Fluid flow rate 1.6
12.8 mL/min
Waveform frequency 100
800 Hz
Fig. 7F
GFP expression or viability (%)
110
100
90
80
0
20
40
60
GFP
Viability
Time (s)

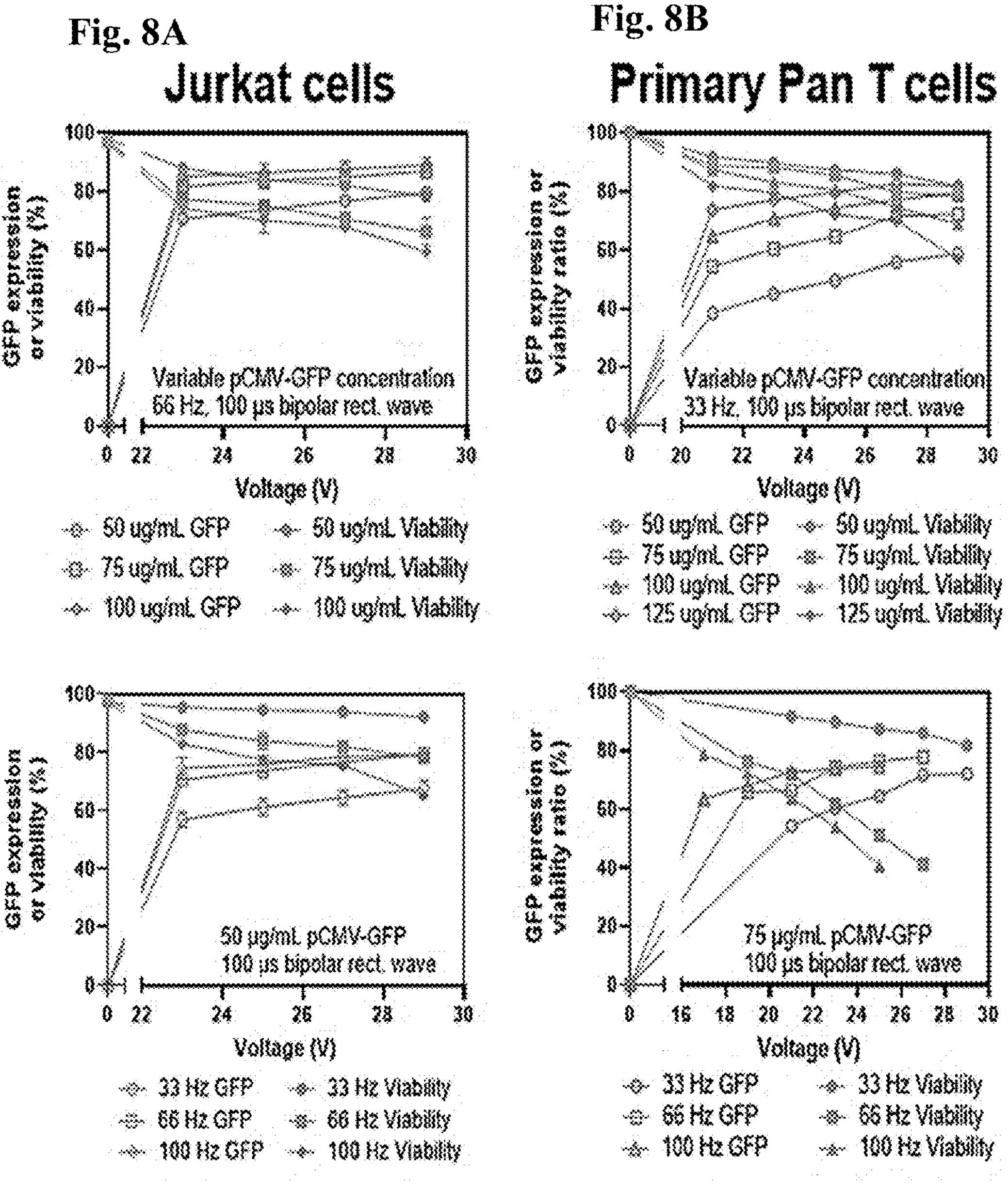
Fig. 8A
Jurkat cells
GFP expression or viability (%)
Variable pCMV-GFP concentration
66 Hz, 100 µs bipolar rect. wave
Voltage (V)
50 ug/mL GFP
75 ug/mL GFP
100 ug/mL GFP
50 ug/mL Viability
75 ug/mL Viability
100 ug/mL Viability
Fig. 8B
Primary Pan T cells
GFP expression or viability ratio (%)
Variable pCMV-GFP concentration
33 Hz, 100 µs bipolar rect. wave
Voltage (V)
50 ug/mL GFP
75 ug/mL GFP
100 ug/mL GFP
125 ug/mL GFP
50 ug/mL Viability
75 ug/mL Viability
100 ug/mL Viability
125 ug/mL Viability
GFP expression or viability (%)
50 µg/mL pCMV-GFP
100 µs bipolar rect. wave
Voltage (V)
33 Hz GFP
66 Hz GFP
100 Hz GFP
33 Hz Viability
66 Hz Viability
100 Hz Viability
GFP expression or viability ratio (%)
75 µg/mL pCMV-GFP
100 µs bipolar rect. wave
Voltage (V)
33 Hz GFP
66 Hz GFP
100 Hz GFP
33 Hz Viability
66 Hz Viability
100 Hz Viability
Fig. 8C
Fig. 8D

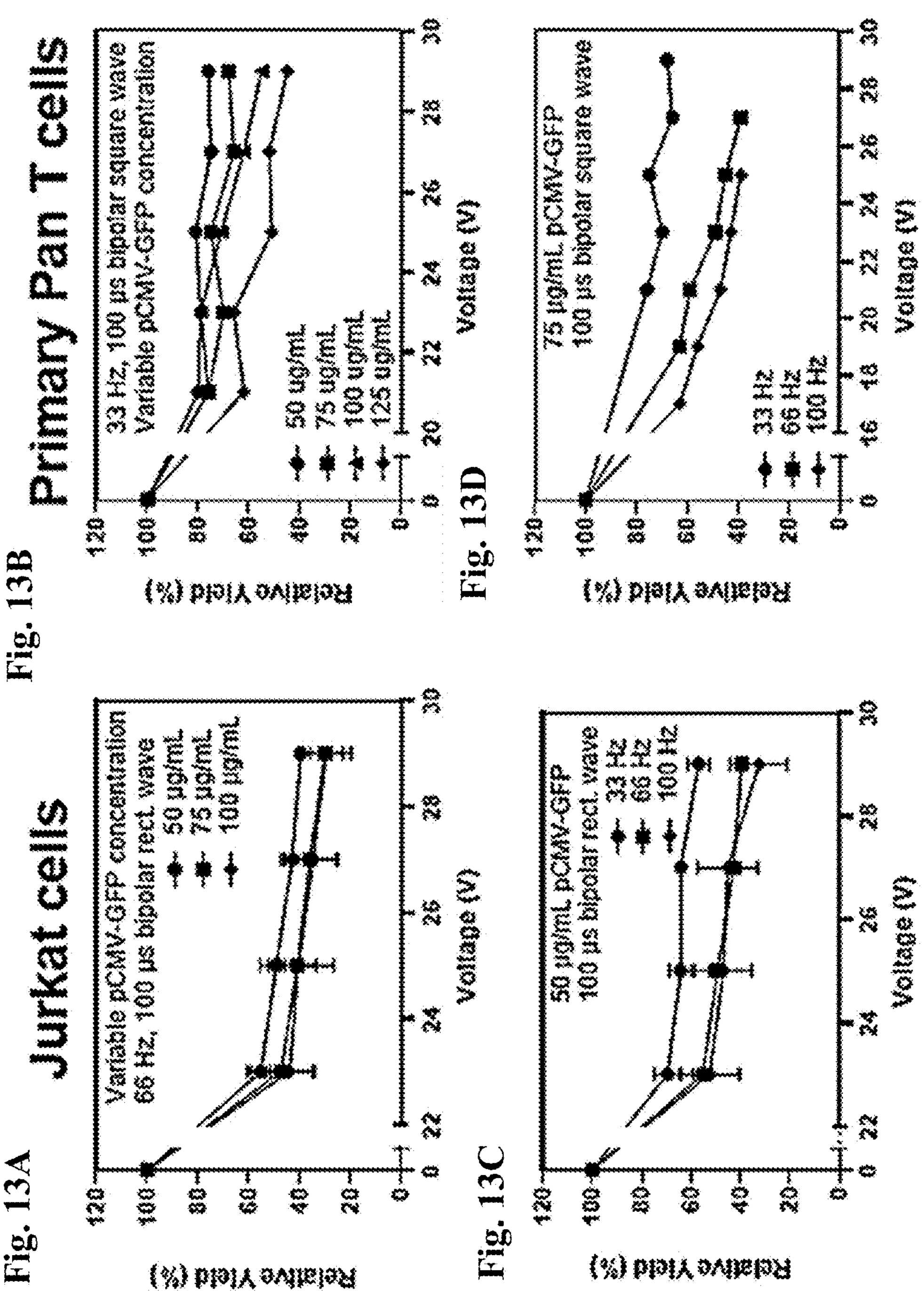
Fig. 13A
Jurkat cells
Variable pCMV-GFP concentration
66 Hz, 100 µs bipolar rect. wave
50 µg/mL
75 µg/mL
100 µg/mL
Relative Yield (%)
Voltage (V)
Fig. 13B
Primary Pan T cells
33 Hz, 100 µs bipolar square wave
Variable pCMV-GFP concentration
50 ug/mL
75 ug/mL
100 ug/mL
125 ug/mL
Relative Yield (%)
Voltage (V)
Fig. 13C
50 µg/mL pCMV-GFP
100 µs bipolar rect. wave
33 Hz
66 Hz
100 Hz
Relative Yield (%)
Voltage (V)
Fig. 13D
75 µg/mL pCMV-GFP
100 µs bipolar square wave
33 Hz
66 Hz
100 Hz
Relative Yield (%)
Voltage (V)

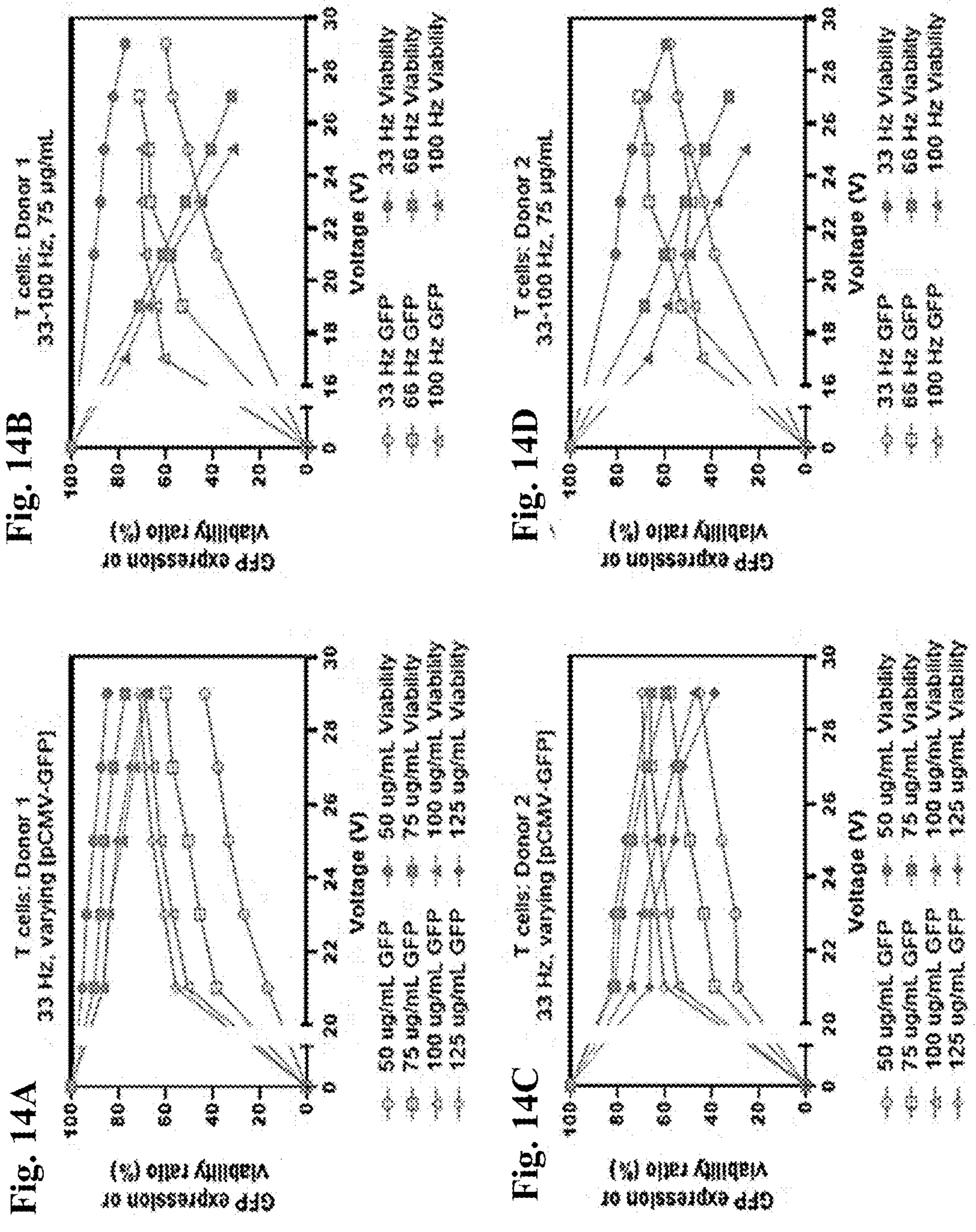
Fig. 14A
T cells: Donor 1
33 Hz, varying [pCMV-GFP]
GFP expression or viability ratio (%)
Voltage (V)
50 ug/mL GFP
75 ug/mL GFP
100 ug/mL GFP
125 ug/mL GFP
50 ug/mL Viability
75 ug/mL Viability
100 ug/mL Viability
125 ug/mL Viability
Fig. 14B
T cells: Donor 1
33-100 Hz, 75 μg/mL
GFP expression or viability ratio (%)
Voltage (V)
33 Hz GFP
66 Hz GFP
100 Hz GFP
33 Hz Viability
66 Hz Viability
100 Hz Viability
Fig. 14C
T cells: Donor 2
33 Hz, varying [pCMV-GFP]
GFP expression or viability ratio (%)
Voltage (V)
50 ug/mL GFP
75 ug/mL GFP
100 ug/mL GFP
125 ug/mL GFP
50 ug/mL Viability
75 ug/mL Viability
100 ug/mL Viability
125 ug/mL Viability
Fig. 14D
T cells: Donor 2
33-100 Hz, 75 μg/mL
GFP expression or viability ratio (%)
Voltage (V)
33 Hz GFP
66 Hz GFP
100 Hz GFP
33 Hz Viability
66 Hz Viability
100 Hz Viability T cells: Donor 3
33 Hz, varying [pCMV-GFP]
GFP expression or viability ratio (%)
Voltage (V)
50 ug/mL GFP
75 ug/mL GFP
100 ug/mL GFP
125 ug/mL GFP
50 ug/mL Viability
75 ug/mL Viability
100 ug/mL Viability
125 ug/mL Viability T cells: Donor 3
33-100 Hz, 75 µg/mL
GFP expression or viability ratio (%)
Voltage (V)
33 Hz GFP
66 Hz GFP
100 Hz GFP
33 Hz Viability
66 Hz Viability
100 Hz Viability Relative Yield (%)
Voltage (V)
50 ug/mL
75 ug/mL
100 ug/mL
125 ug/mL
Variable pCMV-GFP concentration
33 Hz, 100 µs bipolar rect. wave Relative Yield (%)
Voltage (V)
33 Hz
66 Hz
100 Hz
75 µg/mL pCMV-GFP
100 µs bipolar rect. wave

DEVICES AND METHODS FOR INCREASING THROUGHPUT OF FLOW-BASED ELECTROPORATION SYSTEMS

CROSS-REFERENCE TO RELATED APPLICATIONS

This application claims the benefit of priority to U.S. Provisional Application No. 63/255,294, filed on Oct. 13, 2021; and U.S. Provisional Application No. 63/399,024, filed on Aug. 18, 2022; the entire contents of each of said applications are incorporated herein by reference.

BACKGROUND

Cellular therapies have generated enthusiasm for their potential to treat a variety of inherited and acquired diseases. In particular, immunotherapies that utilize autologous T cells modified to express chimeric antigen receptors (CARs) have achieved remarkable rates of complete response with durable, long-lasting remissions for certain hematological cancers. Research is being directed toward treating other cancers such as solid tumors. However, the first generation of approved CAR-T cell therapies rely on viral vectors such as lentivirus or adeno-associated virus (AAV) for cellular reprogramming. Viral vectors have enabled high efficiency transduction of difficult-to-transfect primary human immune cells but have several drawbacks related to their complex and costly manufacturing processes, immunogenicity, and potential for insertional mutagenesis. Furthermore, the field is trending towards more complex reprogramming methods, such as multiple gene edits via CRISPR/Cas9 technology and gene insertion by transposon elements, that are not compatible with typical packaging limits associated with viral approaches.

To circumvent these limitations, non-viral transfection methods have been explored to replace viral delivery. For example, electroporation is a well-studied approach commonly used to deliver DNA, RNA and proteins into cells that is recognized as a leading contender for the replacement of viral vectors. For example, electroporation was used to generate recombinant T cells using nonintegrating DNA nanovectors that bypass many of the drawbacks associated with viral approaches. Similarly, electroporation was recently used to generate CAR-T cells through the use of Sleeping Beauty transposon system for the first clinical trial with virus-free CAR-T cells in Europe as well as with the piggyBac system.

In the standard, static electroporation method that has been used for many years, an electric field is created by applying high-voltage electrical pulses to cell suspensions within a cuvette. The applied high-voltage pulses create transient pores in the cell membrane that allow molecules to diffuse into the cells. However, excessive electric field strength can produce irreversible cell membrane disruption and cell death. In the standard process, the pulse voltage, number of pulses, and pulse duration are among the parameters empirically varied to optimize the efficiency of molecular insertion and cell survival. The empirical optimization can be tedious and there can be variability in the process due to, among other things, the random location of the cells with respect to the electrodes. Furthermore, standard cuvette-style electroporation methods have limited throughput incompatible with large-scale or automated cell manufacturing. As such, limitations on the efficiency of the molecular transfer, cell viability, process variability, and limited throughput have limited the widespread application of this method, even though the potential advantages over the use of viral vectors is understood.

Accordingly, determining the optimal parameters for electroporation of a particular cell type and molecular cargo can require significant time, effort and can consume expensive reagents and sample material. In a flow-based system, numerous parameters must be varied to determine the conditions that most efficiently transfect cells without excessive cell damage.

For example, parameters that may need to be optimized include the flow rates and/or composition of one or more fluids, the voltage temporal waveform, and the voltage amplitude used for electroporation. It is desirable to perform optimization experiments using small sample volumes to reduce cost and to maximize the number experimental parameters that can be explored.

Once optimal parameters for electroporation have been determined, it is desirable to reproduce these conditions with larger sample volumes for clinical applications, such as cell manufacturing for cellular therapies. However, increasing the sample volume often changes the set up so that the conditions found optimal for small sample volumes fail to reproduce the desired transfection efficiency, cell viability, or both.

Thus, there is a great need in the art for devices and methods that can scale electroporation for cellular therapy manufacturing.

SUMMARY

This invention relates, in some aspects, to devices and methods for increasing the throughput of electroporation, for example by retaining some parameters found optimal for small sample volumes and changing certain other parameters in specified ways for larger sample volumes to achieve desired electroporation results, such as transfection efficiency and cell viability.

Accordingly, provided herein are novel microfluidic electroporation devices capable of rapid and reproducible electroporation that can seamlessly scale delivery from the research to clinical scale for applications in cellular therapy. The approach of the present disclosure incorporates a planar flow cell with a thin slab geometry that ensures each cell is subject to the same electric field for reproducible electroporation. Notably, the width of the device in the horizontal direction perpendicular to the flow can be fabricated with selected dimensions to match the desired experimental throughput without changing the electric field experienced by the cells. Using such devices, it is demonstrated herein exemplary delivery of plasmid DNA and mRNA to primary T cells at high efficiency with minimal impact on cell viability. By scaling the width of our device and other parameters such as flow rate, it is demonstrated herein how transfection parameters identified using small-volume, multiplexed optimization can easily be implemented in large-scale transfections required for cell manufacturing. The devices of the present disclosure is used to perform an exemplary therapeutic modification of primary T cells: delivery of CRISPR/Cas9 ribonucleoprotein (RNP) complexes targeted against T cell receptor alpha (TCR-α). Thus, the data presented herein demonstrates the ability of the system to address unmet needs for efficient, non-viral engineering of cells for cell manufacturing.

In some aspects, flow devices for electroporation include a channel having a channel length, a channel height, and a channel width, wherein the ratio of said height to said width is less than about 0.1; an inlet to allow a flow in the channel in a flow direction across the channel length; an outlet to allow said flow from the inlet toward the outlet; and a pair of electrodes disposed across the channel height.

In some embodiments, the flow devices have more than one inlet, more than one outlet, more than two electrodes (e.g., 3, 4, 5, 6, 7, 8, 9, 10, or more electrodes), or a combination thereof. In preferred embodiments, the device of the present disclosure comprises electrodes in pairs (e.g., at least 1, 2, 3, 4, 5, 6, 7, 8, 9, 10, or more pairs of electrodes). Multiple pairs of electrodes may be used to apply electric fields to cells at different times and different locations during their passage through the device.

In some embodiments, the channel is a planar channel. In some embodiments, the height is about 100 micrometers. In some embodiments, the width is at least about 1 millimeter.

In some embodiments, said channel width is the width of the channel along the pair of electrodes. In some embodiments, the dimension of the channel that is perpendicular to both said length and said height is uniform across the channel and is equal to said channel width. In some embodiments, the dimension of the channel that is perpendicular to both said length and said height is non-uniform across the channel. In some embodiments, the dimension of the channel that is perpendicular to both said length and said height is narrower near the inlet and the outlet as compared to said width. In some embodiments, said channel height and said channel length are uniform along their respective dimensions.

In some aspects, a series or a kit of flow devices includes at least two flow devices of any of these embodiments, which differ in said width.

In some aspects, methods of increasing throughput of electroporation include selecting a first parameter subset and a second parameter subset that provide a level of transfection efficiency and a level of cell viability in a first flow-based electroporation setting, and running in a second flow-based electroporation setting an electroporation process using the same first parameter subset but a different second parameter subset, which provides the same level of transfection efficiency and the same level of cell viability at an increased throughput of electroporation. In these methods, the first parameter subset comprises a voltage temporal waveform and a sample composition, and the second parameter subset comprises a flow rate and a channel width. In these methods, when running the electroporation process, the flow rate and the channel width are scaled-up proportionally to each other.

In some embodiments, for these methods, the first flow-based electroporation setting and the second flow-based electroporation setting comprise any of the disclosed flow devices, differing from each other in said channel width. In some embodiments, the first flow-based electroporation setting and the second flow-based electroporation setting comprise any of the disclosed series of flow devices.

In some embodiments, the method comprises proportionally increasing or decreasing the channel width and flow rate, thereby maintaining the same average linear flow velocity of the cells through the channel. In some embodiments, both the channel width and flow rate are proportionally increased. In some such embodiments, increasing the channel width proportionally increases the electrode length such that the electrodes cover the entire width of the channel, thereby allowing all cells flowing in the channel to pass between the electrodes and become exposed to the electrical current. In some embodiments, said flow rate is a volumetric flow rate (i.e., has units of volume per time). In some embodiments of these methods, the word "same," for example when modifying a level or a parameter, means that the two levels or parameters differ from each other by at most 10%. Similarly, scaling up proportionally, when describing these methods, includes increasing the two parameters by the same factor, here again the modifier "same" allowing an error of at most 10%.

In some embodiments, said running is used for manufacturing cells for cellular therapies. In some embodiments, said voltage temporal waveform is a bipolar square wave. In some embodiments, said scale up is by a factor of at least 2, 3, 4, 5, 6, 7, 8, 9, or 10. In some embodiments, said scale up is by a factor of 2, 3, 4, 5, 6, 7, 8, 9, or 10. In some embodiments, said electroporation is used to transfect a nucleic acid into a cell. In some embodiments, said cell is a lymphocyte. In some embodiments, said nucleic acid is an mRNA.

In additional aspects, the same methods can also be used to decrease the throughput of electroporation, for example, by scaling down the flow rate and the channel width proportionally to each other. This may be useful for decreasing reagent consumption.

BRIEF DESCRIPTION OF FIGURES

FIG. 1A-FIG. 1E. Example geometry of a flow device showing opposing pairs of electrodes across the channel. This system indicates a single fluid input but there can be one or more inputs to the device. There can also be one pair of electrodes or more electrodes than the one pair on each chip (e.g., 3, 4, 5, 6, 7, 8, 9, or 10 electrodes or more, which need not all be in pairs). (FIG. 1A) Side and (FIG. 1B) top view schematic of the electroporation flow cell. (FIG. 1C) A photograph of an experimental flow cell with attached manifolds, tubing, and three sets of independently addressable electrodes (left panel). A schematic diagram of an exemplary device (right panel). (FIG. 1D) Block diagram depicting components that comprise the electroporation platform/device. (FIG. 1E) Plot depicting a bipolar rectangular waveform with frequency f, duration t, and voltage amplitude, V.

FIG. 3A shows a fluid channel geometry with constant width and 3 pairs of electrodes. This is similar to the device shown in FIG. 4A. FIG. 3B shows a device with 2 electrode pairs and a different width at the fluid inlet compared to the width at the electrode region. This resembles the scaled channel geometry of the devices used in Example 2 and shown in FIG. 4B. Each electrode region shown here represents a pair of opposing electrodes similar to the geometry described in U.S. patent application Ser. Nos. 15/478,924 and 16/876,718, each of which is incorporated herein by reference.

(FIG. 4A) Photograph of 2-mm and (FIG. 4B) 10-mm width flow chips. (FIG. 4C) Waveform used to electroporate primary T cells in both channel widths. (FIG. 4D) Representative flow cytometry graphs depicting measurement of cell count, viability (7-AAD), and transfection efficiency (GFP). (FIG. 4E) Plot depicting results from 2-mm and (FIG. 4F) 10-mm channel width transfections. Transfection efficiency and viability are roughly identical between the 2- and 10-mm channel widths. Cell proliferation is identical between control and electroporated cells in both channel widths. EP: Electroporated cells. Cntrl: Control cells.

(FIG. 6A) Representative flow cytometry plots from zero voltage-control or (FIG. 6B) electroporated Jurkat cells depicting cell morphology, viability, and GFP expression. (FIG. 6C) Impact of varying waveform voltage amplitude on delivery using 20 or 40 μg/mL mRNA to Jurkat cells (N=3, n=3). (FIG. 6D) High efficiency delivery using 40 μg/mL mRNA for primary T cells from four healthy donors (N=4; n=4). Data shown as mean±standard deviation.

FIG. 7A-FIG. 7F: Increasing cell processing throughput for clinical-scale volumes. (FIG. 7A) Photograph of a 2 mm and (FIG. 7B) 10 mm electroporation flow cell. Red arrows highlight the channel width. (FIG. 7C) Plot of GFP expression and viability values from Jurkat cells transfected with mRNA encoding GFP in either the 2- or 10-mm channels (N=3, n=3). (FIG. 7D) Plot of GFP expression and viability values from Jurkat cells transfected with mRNA encoding GFP in the 2-mm channel at varying cell concentrations (N=3, n=3). (FIG. 7E) Plot of GFP expression and viability values from Jurkat cells transfected with mRNA encoding GFP in the 10-mm channel at varying flow rates and voltage temporal waveform (N=3; n=3). (FIG. 7F) Plot of GFP expression and viability over time from an experiment that transfected ~240 million cells. Data shown as mean±standard deviation (FIG. 7C, FIG. 7D, FIG. 7E).

FIG. 8A-FIG. 8D: Results for various transfection parameters for delivering plasmid DNA to Jurkat and primary T cells. (FIG. 8A) Impact of varying plasmid concentration for delivering plasmid DNA to Jurkat and (FIG. 8B) primary T cells. (FIG. 8C) Impact of varying voltage temporal waveform and voltage amplitudes for delivering plasmid DNA to Jurkat and (FIG. 8D) primary T cells. Data shown as mean±standard deviation from N=3 independent experiments (FIG. 8A, FIG. 8C). Data shown as values from a representative donor (FIG. 8B, FIG. 8D).

FIG. 9A-FIG. 9C: Delivery of an arbitrary electrical waveform. (FIG. 9A) Plot depicting a bipolar, dual voltage waveform characterized by a short-duration, high-amplitude segment ($V_1$, $t_1$) followed by a long-duration, low-amplitude segment ($V_2$, $t_2$) (FIG. 9B) Impact of varying $V_2$ while $t_2$=250 μs. (FIG. 9C) Impact of varying $t_2$ while $V_2$=4V. In both (FIG. 9B) and (FIG. 9C), we fix f=66 Hz, $V_1$=21 V, and $t_1$=75 μs.

(FIG. 12A) Plot of relative yield from Jurkat cells transfected with mRNA encoding GFP in either the 2- or 10-mm channels (N=3, n=3). (FIG. 12B) Plot of relative yield from Jurkat cells transfected with mRNA encoding GFP in the 2-mm channel at varying cell concentrations (N=3, n=3). (FIG. 12C) Plot of relative yield from Jurkat cells transfected with mRNA encoding GFP in the 10-mm channel at varying flow rates and voltage temporal waveforms (N=3; n=3). Data shown as mean±standard deviation.

FIG. 13A-FIG. 13D: Relative yield data for various transfection parameters for delivering plasmid DNA to Jurkat and primary T cells. (FIG. 13A) Impact of varying plasmid concentration on relative yield for delivering plasmid DNA to Jurkat and (FIG. 13B) primary T cells. (FIG. 13C) Impact of varying voltage temporal waveform on relative yield for delivering plasmid DNA to Jurkat and (FIG. 13D) primary T cells. Data shown as mean±standard deviation from N=3 independent experiments (FIG. 13A, FIG. 13C). Data shown as values from a representative donor (FIG. 13B, FIG. 13D).

FIG. 14A-FIG. 14F: Results for various transfection parameters for delivering plasmid DNA to primary T cells from additional donors. (FIG. 14A) Impact of varying plasmid concentration and (FIG. 14B) voltage temporal waveform for primary T cell donor 2. (FIG. 14C) Impact of varying plasmid concentration and (FIG. 14D) voltage temporal waveform for primary T cell donor 3. (FIG. 14E) Impact of varying plasmid concentration and (FIG. 14F) voltage temporal waveform for primary T cell donor 4.

(FIG. 15A) Impact of varying plasmid concentration on relative yield for delivering plasmid DNA to primary T cells. (FIG. 15B) Impact of varying voltage temporal waveform on relative yield for delivering plasmid DNA to primary T cells. Data shown as mean±standard deviation from N=4 independent experiments and four healthy donors.

(FIG. 16A) Impact of varying $V_2$ while $t_2$=250 μs. (FIG. 16B) Impact of varying $t_2$ while $V_2$=4V. In both (FIG. 16A) and (FIG. 16B), we fix f=66 Hz, $V_1$=21 V, and $t_1$=75 μs.

DETAILED DESCRIPTION

Figure 2A:
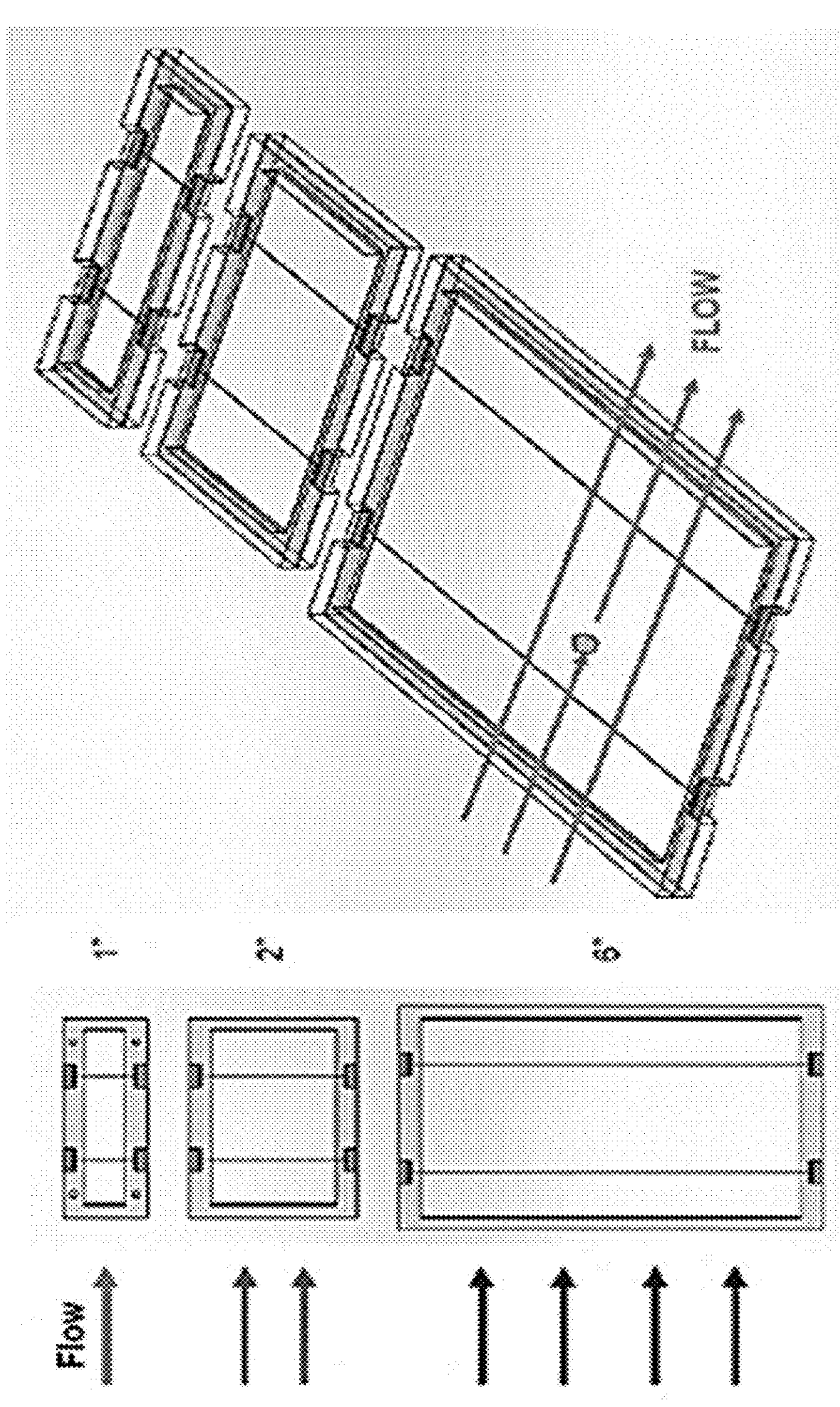
FIG. 2A. (Left) Top-down schematic view of a series of planar microfluidic flow devices with the width of the device channel increasing from one inch at the top, to two inches in the middle, and six inches at the bottom. The width is the dimension perpendicular to the flow direction and in the plane of the page. The flow devices are depicted as each containing two electrodes, though this number is easily varied in the manufacturing process. (Right) Angled schematic view of the same series of flow devices.
Figure 2B:
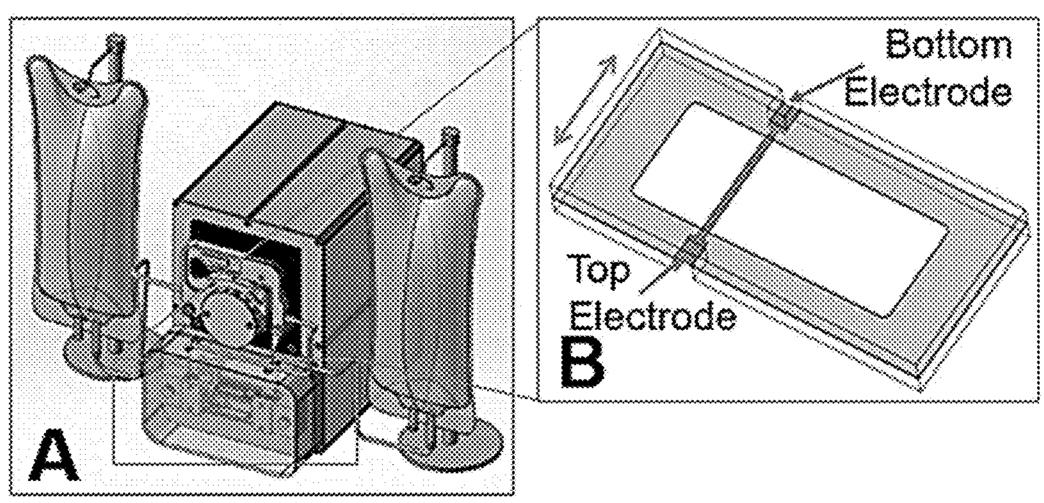
FIG. 2B. Panel A shows an exemplary high volume electroporation system having a "closed design" where large volume fluid bags are connected via Luer style fittings allowing for aseptic connections to be made with the fluidic device. This high volume system is characterized by its good manufacturing practice (GMP)-compatible closed system, a peristaltic pump, a wider chip with a wider channel, a larger diameter tubing, a larger inlet/outlet ports, longer electrodes, and higher flow rates, all of which provide the capability to produce the electroporated cells at a clinical scale. Panel B shows a fluidic device having an increased width dimension allowing for processing of large liquid volumes in short time frames.
Figure 2C:
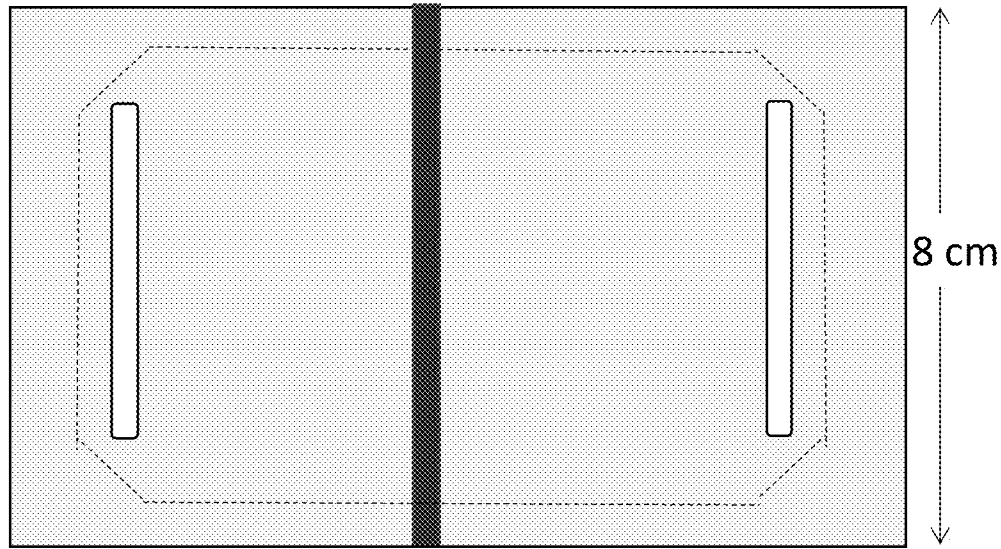
FIG. 2C shows an exemplary large volume electroporation device having the width of 8 cm. The dotted line represents the outline of the channel. The black bar in the middle represents a pair of electrodes that supply electrical current to the cells as they pass between the electrodes.
Figure 2D:
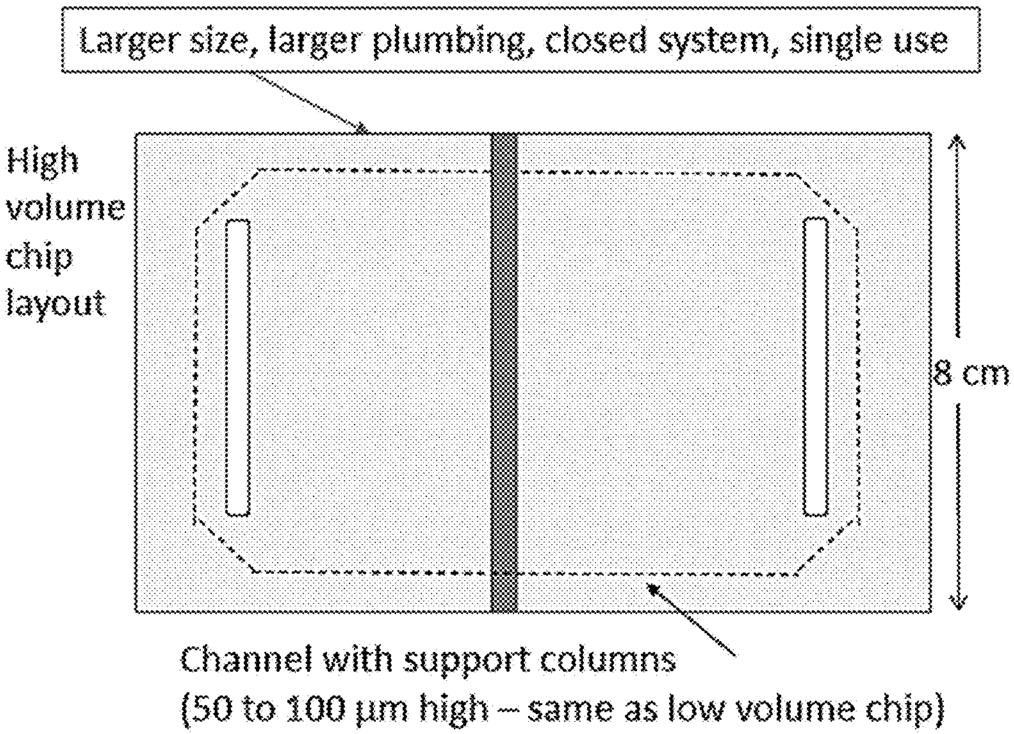
FIG. 2D shows a comparison of an exemplary smaller chip (top) for electroporation of a small volume of cells to determine the optimal parameters for electroporation; and an exemplary larger chip (bottom) for use in a scale-up for electroporation of cells in a clinically significant scale (e.g., for CAR therapy).

Presented herein are novel electroporation devices capable of rapid and reproducible electroporation that can efficiently transfect small volumes of cells for research and process optimization and scale to volumes required for applications in cellular therapy. For example, using the electroporation devices of the present disclosure, plasmid DNA and mRNA have been delivered to primary human T cells with high efficiency and viability, such as >95% transfection efficiency for mRNA delivery with <2% loss of cell viability compared to control cells.

Further presented herein are methods for scaling delivery that achieve a manufacturing level. For example, demonstrated herein is an experimental throughput of 256 million cells/min.

Finally, also demonstrated herein is a therapeutically relevant modification of primary T cells using CRISPR/Cas9 to knockdown T cell receptor alpha (TCR-α) expression. This study displays the capabilities of the electroporation devices to address unmet needs for efficient, non-viral engineering of T cells for cell manufacturing.

Definitions

The articles "a" and "an" are used herein to refer to one or to more than one (i.e. to at least one) of the grammatical object of the article. By way of example, "an element" means one element or more than one element.

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

All numerical ranges provided herein are understood to be shorthand for all of the decimal and fractional values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9 and all intervening fractional values between the aforementioned integers such as, for example, ½, ⅓, ¼, ⅕, ⅙, ⅛, and ⅑, and all multiples of the aforementioned values. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the term "chip" is used interchangeably with the term "device."

As used herein, the term "voltage waveform" (or related terms, e.g., "time-dependent voltage waveform," "temporal voltage wave form") refers to the voltage that varies in time as supplied to the electrodes by the voltage controller or other source of voltage. This may be described by a periodically repeated time varying function, but it can also vary arbitrarily in time and not be repeated.

The present disclosure relates to devices and methods for modifying (e.g., increasing or decreasing) electroporation throughput, or a method for obtaining a desired throughput of electroporation using a microfluidic device. The devices and methods allow maintaining electroporation outputs, such as cell viability and transfection efficiency. In some aspects, once optimal conditions are known for a small sample volume, the methods include increasing the volumetric flow rate and the channel width along the electrodes in proportion to each other (e.g., each by about a factor of 2, 4, 6, 8, 10, 20, 30, 40, 50, 100, or more).

The devices and methods for modifying (e.g., increasing or decreasing) the throughput of a flow-based electroporation system while maintaining the cell modification conditions and results are further explained below and in the drawings, and are illustrated in the provided examples.

Determining the optimal parameters for electroporation of a particular cell type and molecular cargo can require significant time, effort and can consume expensive reagents and sample material. In a flow-based system, numerous parameters must be varied to determine the conditions that most efficiently transfect cells without excessive cell damage. For example, parameters that may need to be optimized include the flow rates and/or composition of one or more fluids, the voltage temporal waveform, and the voltage amplitude used for electroporation. It is desirable to perform optimization experiments using small sample volumes to reduce cost and maximize the number experimental parameters that can be explored. Once optimal parameters for electroporation have been determined, it is desirable to reproduce these conditions with larger sample volumes for clinical applications such as cell manufacturing for cellular therapies.

A planar type flow device is shown in FIG. 1A-FIG. 1D. It is thin in one dimension perpendicular to the flow and this dimension establishes the distance between the electrodes. The width dimension perpendicular to the thickness dimension can be varied as desired. The disclosed embodiments exploit this difference between thinness and width of the flow channel.

Herein, we disclose a method to increase the throughput of a thin planar microfluidic device by increasing the width of the flow channel and the flow rate in the same proportion (i.e., doubling the width and doubling the flow rate) so that the cells then experience the same electrical and mechanical forces and conditions. We refer to a microfluidic device similar to that discussed in U.S. Pat. No. 11,225,638 and U.S. Patent Publication No. 2020/0399578, each of which is incorporated herein in its entirety, with electrodes transverse to the direction of flow as shown in FIG. 2A. The separation of electrodes in a pair is about 80 microns to 100 microns in some embodiments and the channel width, perpendicular to the flow direction, is at least about 1 mm in some embodiments. The ratio of the narrow to the wide dimension of the flow channel, both transverse to the direction of the flow, is less than about 10%. FIG. 1A-FIG. 1E show the basic concept of increasing the throughput of the microfluidic electroporation device by scaling its width. This unique capability is not available in current commercial systems and represents an advance we have demonstrated with cell types typically used for cell therapy applications.

Increasing the volumetric flow rate is a method for increasing throughput. However, simply increasing the flow rate alone in the flowing system will decrease the time that each cell is subject to either the electric or mechanical force required to porate the cell. The transit time of the cells though the electrode region is inversely proportional to the fluid flow velocity. Decreasing the time duration of the applied electric field or force will change poratin with unpredictable results. One can attempt to overcome this by, for example, changing the strength of the applied electric field. However, this may not produce the same transfection efficiency or cell viability for all cell types. Additionally, if the voltage temporal waveform has a complex shape, it may not be intuitive how to change the time varying voltage to obtain similar conditions with varying flow velocity. In the case of a mechanical force, it is less obvious how to address variations in transfection efficiency due to the variable time that the force is applied at different flow rages.

The planar architecture of the flow chip, with the ratio of the narrow to wide dimension perpendicular to the flow being less than 10%, plays an important role in the ability to increase the width and flow rate without affecting the electrical environment of the cells. In a microfluidic device with a circular cross section, or one where the radio of the width to height is approximately 1, the fluid velocity has a parabolic shape across the channel with a maximum at its center. As is discussed in detail in Biotechnology at Low Reynolds Number by J. Brody et al, Biophysical Journal 71, December 1996, pg 3430-3441, which is incorporated herein by reference in its entirety, the velocity profile in a rectangular channel becomes ‘plug-shaped’ along the wide dimension when the ratio of the narrow to wide dimension is less than 10%. This plug-shaped profile is constant until it changes to zero velocity at the edges over a distance comparable to the height of the channel. This plug-shaped velocity profile is a well-known feature of so-called Hele-Shaw flow in rectangular flow cell with a small narrow to wide aspect ratio.

This implies that the time a cell is subject to an electric field in the flow cell we describe is essentially constant for any position along the width of the flow cell (except near the edges as detailed). If we increase the throughput of said device by proportionally increasing the width and the volumetric flow rate, this feature remains unchanged. Thus, the electroporation parameters optimized in a low sample device are unchanged in such a device with an increased width and flow rate. This is in contrast to cylindrical flow cells or those with roughly equal widths and heights, where the time a cell is subject to the electric field depends on its lateral position.

Further, we can negate the effect of the reduced velocity at the edges of flow chip by decreasing the electrode size along the direction of the flow in this region. As the flow approaches zero over a distance comparable to the height of the channel in this region, the cells will be moving more slowly on average than those in the plug-shaped region of the velocity profile. By reducing the dimension of the electrodes along the flow direction proportionally, we can cause the cells in this edge region to experience the electrical field for nearly the same time as those in the constant velocity region. This reduces variability in the transfection efficiency and viability.

Figures 3A, 3B:
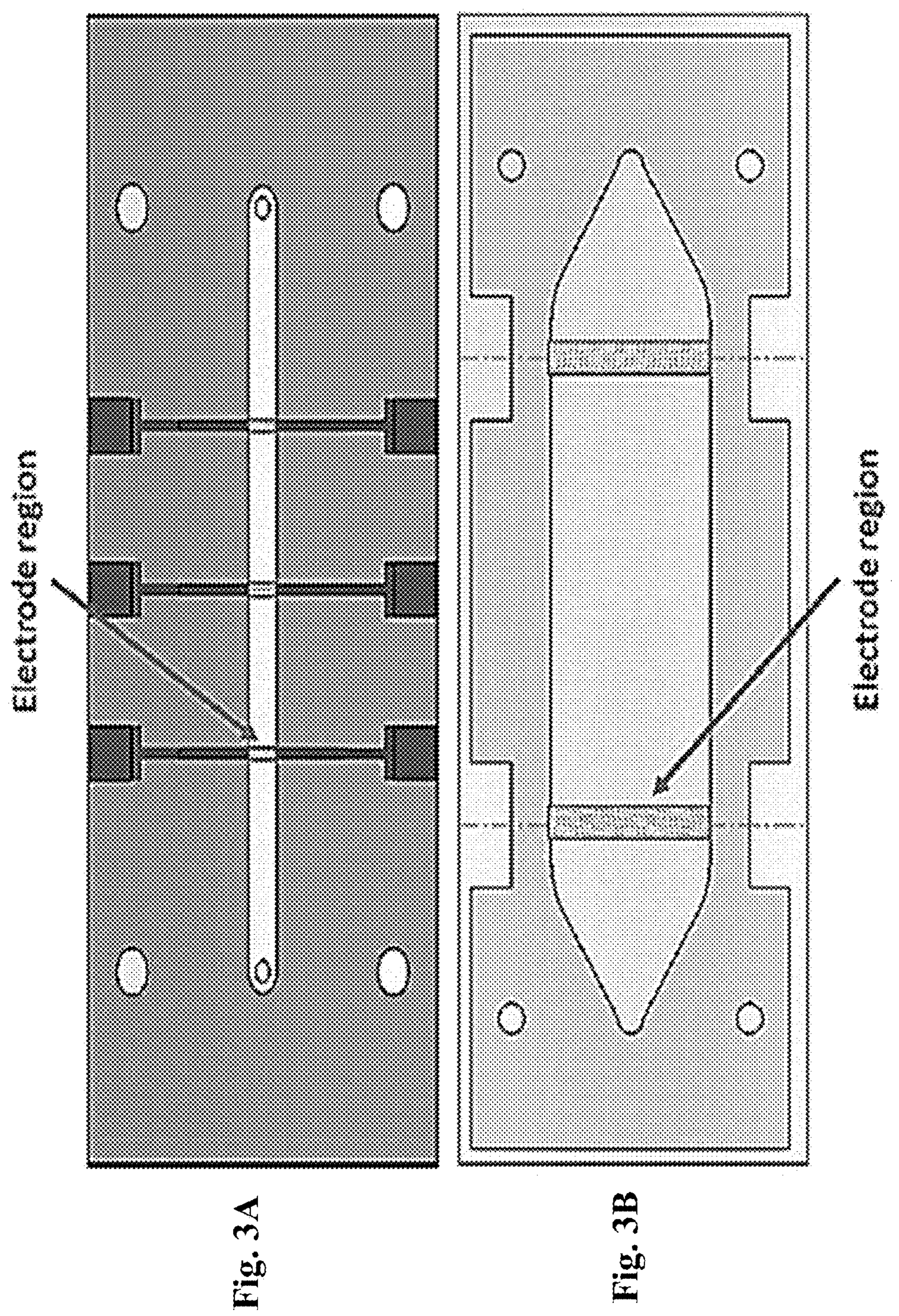
FIG. 3A-FIG. 3B. Channel geometry examples, as top-down view.

It is also important to note in this disclosure that by increasing the width, we are referring to the width in the region between the opposing electrodes. In one of our example flow-device geometries the flow channel flares out from the inlet to the full width as shown in FIG. 3B in order to maintain laminar flow. When we refer to increasing the throughput by increasing the width and the volumetric flow rate proportionally, it is the width in the region between the electrodes that is relevant (see, e.g., FIGS. 3A and 3B).

Figure 5:
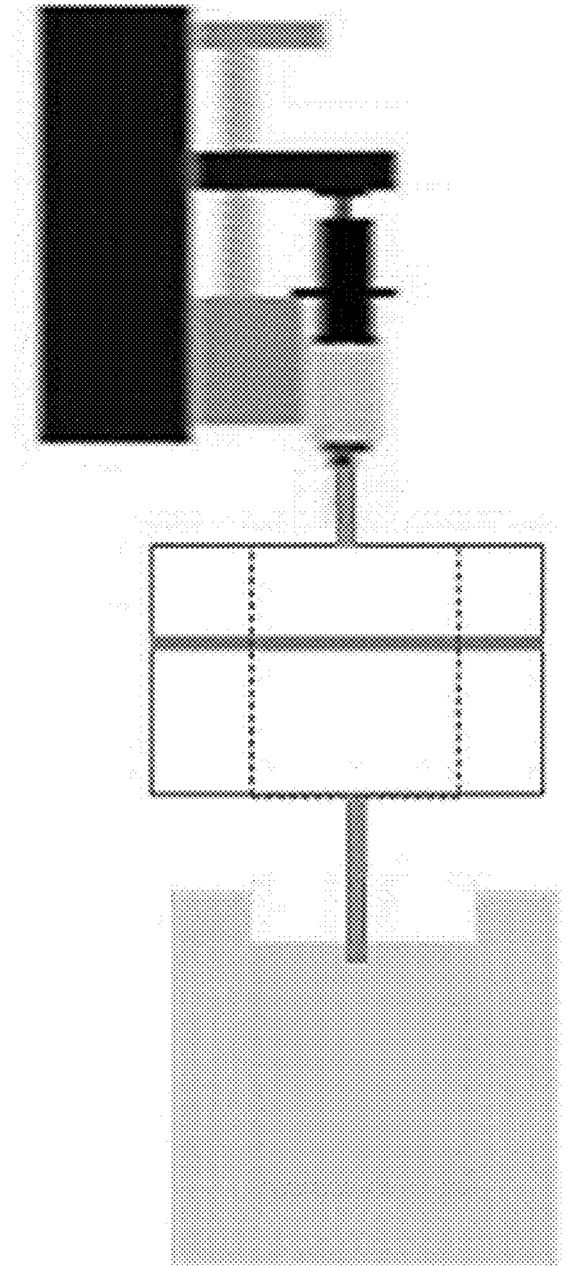
FIG. 5: A schematic for a version of a high volume electroporation system which incorporates a pump with a larger capacity, a flow device with the wider channel width, and larger liquid volume.

With the disclosed systems/devices we can readily scale the process simply by increasing the width of the flow channel and proportionally increasing the volumetric fluid flow rate, resulting with proportionally more processed sample in a given time. FIG. 5 depicts the general approach of widening the channel and proportionally increasing the volumetric flow rate.

Flow Devices for Electroporation

For increasing the electroporation throughput, disclosed are flow devices (also referred to as an electroporation device or platform) that have a selected (e.g., based on the desired electroporation throughput) channel width along the electrodes. Also provided are a set of at least two flow devices (e.g., one having a narrower channel width along the electrodes for selecting desired parameters, and one having a broader channel width along the electrodes for performing the scaled-up procedure). In some embodiments, the set comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 flow devices. Each of the flow devices in the set may comprise the same width or different widths.

Additionally disclosed are flow devices that have a predetermined channel width along the electrodes for directly performing the high-throughput electroporation process, for example when parameters for smaller sample volumes have already been determined (e.g., by the same team or a different team).

The disclosed flow devices for electroporation include a channel, at least one inlet (e.g., at least 1, at least 2, at least 3, at least 4, at least 5, at least 6, at least 7, at least 8, at least 9, or more inlets), at least one outlet (e.g., at least 1, at least 2, at least 3, at least 4, at least 5, at least 6, at least 7, at least 8, 9, or more outlets), and at least one pair of electrodes (e.g., at least 2, at least 3, at least 4, at least 5, at least 6, at least 7, at least 8, at least 9, or more individual electrodes).

The channel, as a three-dimensional void within the device, has a length along the flow direction from the inlet to the outlet, a height between the pair of electrodes, and a width parallel to the electrodes and perpendicular to both the height and the length. The “width” in this disclosure is used to refer to the width that runs along the electrodes, which may be the same as or different from the respective dimension of the channel parallel to that width. In addition, the channel geometry is not necessarily a rectangular prism; it may be irregular; for example, it may be narrower along the width dimension near the outlet and the inlet. In some embodiments, the channels are planar.

In some embodiments, the channel width is at least about 0.1, 0.2, 0.3, 0.4, 0.5, 0.6, 0.7, 0.8, 0.9, 1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, or 2000 millimeters (mm). In some embodiments, the channel width is at least about 1 mm. In some embodiments, the channel width is at least about 2 mm. In some embodiments, the channel width is at least about 10 mm. In some embodiments, the channel width is at least about 20 mm. In some embodiments, the channel width is at least about 80 mm.

In some embodiments, the channel height is at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 millimeter (mm). The height, in some embodiments, is about 40, 50, 60, 70, 80, 90, 100, 110, 120, 130, 140, 150, 160, 170, 180, 190, or 200 micrometers (μm). In some embodiments, the height is 80 micrometers. In some embodiments, the height is 100 micrometers.

The ratio of the height to the width (i.e., height/width) is, in some embodiments, less than or equal to about 0.1 (e.g., at least about 0.1, at least about 0.09, at least about 0.08, at least about 0.07, at least about 0.06, at least about 0.05, at least about 0.04, at least about 0.03, at least about 0.02, at least about 0.01, or less). A wide range of widths can be employed guided by the height and ratio features. For example, the width, in some embodiments, is at least about 1 millimeter (e.g., at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20 millimeters or more).

Fluid Inputs and Streams

The fluid can flow through the channel at a rate of 0.1 cm/s, with a relevant range of flow rate between 0.001 cm/s and 10 cm/s. The volume of fluid flowing through the channel relates to the cross-sectional area of the flow channel. For example, for a channel 2 cm wide and 100 micrometers high, the volumetric flow rates would be in the range of from about 0.2 microliters/s to 2 milliliters/s.

The device permits the use of multiple inputs of fluid through slits in the channel device to provide flow with different layers of solution composition. The flow rate of two or more fluid streams into the channel can be controlled to create a sheath flow. Various streams of cells or molecules can enter the channel via these inputs, and these streams can have the same or different flow rates. If desired, streams with different flow rates adopt laminar flow through the channel. Thus, the streams flow in parallel through the channel and remain largely separated, mixing slowly only through diffusion. In this manner, individual cells in the stream of living cells can be isolated between the electrode pair by the laminar flow of the adjacent fluid streams.

The use of multiple inputs of fluid can prevent various types of fouling or contamination. For example, the molecules or nucleic acids to be inserted into the cells can exist in a separate solution from the cells. This can be useful because certain molecules, like RNA, may not be stable in the vicinity of living cells due to enzymes on the cell surface or cell culture media. Also, it is known that degradation of the electrodes can result in the release of contaminants that are toxic to cells. The separate fluid layers ensure that the cells remain free from contaminants from the electrodes. Further, the cells themselves are kept out of contact with both the surface of the support block and the electrodes preventing possible contamination.

In some embodiments, using separate fluid streams allows maintaining different components in media optimal to them for a longer time. For example, one fluid stream can contain the cells to be electroporated, and instead of keeping the cells in a medium that is best for electroporation efficiency, the cells can be kept in a medium that is optimal for them (e.g., for their survival) before electroporation, and then allowed to mix with an electroporation medium during the actual electroporation time window. After the electroporation is complete, the cells can be switched back into the medium that is optimal for them. This allows minimizing the time the cells are in a medium that is not the best for their well-being. The embodiments disclosed herein thus allow dynamically controlling the chemical environment of the cells and the reagents to be electroporated into the cells separately, for example as a function of time and/or position within the fluid channel.

Alternatively, some embodiments of the device can contain a single fluid input through which a homogenous solution of cells and biologically active molecules enter the channel. The stream may consist of a conductive buffer solution containing the biologically active molecules that are to be inserted into the living cells. Compared to the device having multiple inputs, this might be advantageous in that there is a greater opportunity for the cells and the biologically active molecules to come into contact with one another and could increase the efficiency of transformation.

Fluid streams may interface to the device via tubing, fittings, interconnects, a manifold, or discreet fluid path connections. One or more of these parts can be part of the fluid interface. The fluid interface serves to reformat the tubing or conduits into the receiving slit-port of the device. The fluid interface may have changes in surface area as well as varying geometries for delivering fluid to the device. The fluid interface may have features to enhance mixing or maintain laminar flow characteristics. This includes geometric changes that may aid in turbulent flow, diffusion rate changes, or residence time in the flow path. The fluid path may have geometries tailored to avoid the trapping gas (bubbles) or seeding to avoid gas bubble formation due to gas coming out of solution.

The fluid path components may be machined, molded (e.g., injection molding), casted, extruded, or the like. The fluid interface may be fabricated as part of the channel device (one-piece) or bonded (integrated) to the device via a permanent or non-permanent bond. Alternatively, the fluidic interface could be manufactured as part of the device as one integrated component, for example via injection molding where the device and fluid interface are both formed during the molding process. Sealing between the fluid interface and the device may be hermetic, compression-based, O-ring-based, gasket-based, adhesion-based, fused, luer locked (quick connect), flat bottom compression-based, tapered ferrule-based, frusto-conical compression-based, friction fit, barbed connection, or the like.

Fluid transfer lines may be soft, semi-hard, or hard where the leak tight seal between components are made with connections known to those in the art.

Tubing and fluid conduits may be manufactured via extrusion or molding.

For some manifold designs, portions of the system may not contain tubing and fluid will be routed via the manifold structure.

In some embodiments, the fluid interface to the device may be via a leak-tight seal to the planar device with a compressive material such as an O-ring or gasket.

The device can be interfaced to a fluid delivery system. A fluid delivery apparatus or pump is configured to displace fluid from a vessel to establish a fluid flow within the fluid path. The fluid vessel may contain a pure fluid or a solution. The fluid may contain cells, small molecules, or large molecules including chemical entities for the transfection process. The fluid displacement apparatus can provide positive and/or negative displacement of the fluid. This allows fluid to be pushed or pulled through the device and the fluid path components.

The delivery pump may include mechanisms comprising peristaltic, syringe, gear pump, diagram, gas pressure (positive or negative), centrifugal, piston, check-valve, or mechanical displacement, hydrostatic or gravity driven flow.

Preferably, the fluid is indirectly displaced by the pump without the liquid directly contacting any of the moving parts of the apparatus, such as, for example, a peristaltic pump acting upon a fluid filled tube. Alternatively, a positive pressure displacement mechanism may be used where a head pressure displaces liquid from a pressurized vessel, or a negative displacement where a vacuum is used to pull liquid into the electroporation device; vacuum via pressure regulator or a peristaltic pump. The use of negative displacement allows for limited system components to be implemented on the inlet side of the device.

When pulling liquid through the device using negative displacement, an intermediate vessel could be used to capture the cells and fluid exiting the device to avoid contact with the pump's negative displacement equipment (for example syringe, peristatic pump tube, flow sensor, or the like).

Conversely, fluid may be directly displaced by an apparatus, when the fluid is displaced by directly contacting any of the moving parts of the apparatus, such as, for example, the plunger of a syringe pump. Alternatively, the syringe pump could pull liquid through the device with the target fluids not traveling to the point of reaching the syringe barrel. The syringe may be re-usable or disposable. The syringe may be integrated in the fluid path or connected at the time of use.

Fluid control may be open-loop or may have closed-loop feedback control.

Pumping systems established to date have several weaknesses for controlling flow rate accuracy and precision, and may have performance limitations around controlling stable non-pulsing flows. Controlling of fluid pulsing for the electroporation device is most preferably controlled on the time frame of less than 30 seconds, more preferably less than 10 seconds, and most preferable faster than 1 second. Pulsing control is better than that of 20% for the given time period mentioned in the latter.

For the electroporation device, some preferred embodiments may comprise the peristaltic pump mechanism and or a gas pressure pump-based mechanism. Both types may operate to pull or push liquid.

Traditional peristaltic pumps suffer from high pulsing delivery because the fix rate of mechanical contact on the pump tube via rollers (or linear compression mechanisms) which continuously alter the cross-section area by compressing the tube resulting in tube ID change. Pulsing results from the cross-sectional change of the tube ID. Additionally, peristaltic pumps suffer from accuracy issues that result from tubing compliance changes and tube wear characteristic changes over time and use. This wear is difficult to be compensated or adjusted for without direct measurement of the fluid flow rate or measuring the output with a balance or volumetric measurement. Measuring liquid flow rate with a balance is not preferred, as then an additional instrument must be added that requires an adequate environment (e.g., temperature, humidity, vibration, and space). Also, the fluid path then becomes dependent on access to the relatively large footprint/space requirement of a balance.

Pressure pumps deliver relatively non-pulsatile flow but can suffer from accuracy issues because of fluid path dimensional tolerances, viscosity and temperature changes (fluid and ambient temperature), and liquid height changes as vessels are emptied and filled. Measuring liquid flow rate with a balance is not preferred as then an additional instrument must be added that requires an adequate environment (e.g., temperature, humidity, vibration, and space). Also, the fluid path then becomes dependent on access to the relatively large footprint/space requirement of a balance.

To counter these limitations a flow-sensor may be used to provide closed-loop feedback to the liquid displacement mechanism. Here is proposed the addition of a fluid flow rate sensor (in line with system components) to measure the flow rate in near-real-time with the ability to provide feedback to the fluid displacement mechanism. For example, a flow rate sensor with a peristaltic pump or a gas pressure control system acting on a fluid vessel. The flow rate sensor may control the fluid displacement continuously or intermittently. The sensor may also be used to measure the flow rate as a check in the case of open-loop operation.

Most preferably, in some embodiments, the sensor does not contact the fluid and is not in communication with the device, tubing, or conduit.

The sensor may be reusable where it is used in conjunction with a disposable fluid component(s). Or the sensor may be disposable.

Most preferably, the two types of sensor that may be used include, but are not limited to: (1) ultrasonic-based sensor that is in communication with the fluid path (non-contact), which sensor is in communication with a component the liquid is traveling through; and (2) thermal flow sensor that is in communication with the fluid path (non-contact), which sensor is in communication with a component the liquid is traveling through.

The sensors may be re-used where they temporarily interfaced with a fluid path component that is to be changed, or the sensor may be part of the path and be disposable in nature. In some embodiments, the disposable sensor is integrated in the fluid path.

Interfacing of the liquid entering the device may occur via one or more components, such as a tube or conduit, and/or a fluid interface. The fluid component may comprise one or more features that allow for distributing or altering the flow profile and path of the fluid. This component may a wetted path where the cross-section area and shape may be varying from that of the fluid component exiting cross sectional area or shape. The fluid path change may be part of an assembly or may be molded as part of the electroporation device.

This may include geometric shape(s) that redistribute or format the liquid flow from the tube conduit to a format that is compatible with the device inlet. This architecture of the fluid path depends on the incoming fluid source tubing, fitting, or fluid interface as well as the device fluid inlet shape.

The fluid interface component may be composed of one or more fluid paths and is not limited to the location or number of inlet or outlet features.

A fluidic interface may serve to allow for various formats and types fluid components to make a fluid seal to the microfluidic device inlet. The device inlet may be a circular shape or may have a non-cylindrical geometry or shape. A fluidic interface component may for example allow for one or more incoming fluid lines or conduits to connect to the fluidic interface inlet where the fluid may then traverse a changed cross-section or geometric shape, followed by the fluid exiting the fluidic interface in a cross-section or shape that matches the device fluid inlet geometry. The fluid device inlet geometry would correspond to the fluid interface component output geometry. For example, the fluidic interface may serve to allow for a traditional tube to then supply fluid to a split on the device. Interfacing the fluid can be accomplished in many ways (e.g., different geometric shapes for different types of conduits/tubes), which are available to a person of ordinary skill in the art.

Cells can be manipulated post electroporation. In some embodiments, after electroporation, cells are transferred from the PA to a sterile, multi-well dish or T-flask and allowed to recover for 30-40 minutes at 37° C. The cells are suspended in standard cell medium and either cultured for immediate use or cryopreserved.

In some embodiments, the electroporation device is interfaced to a receiving station that serves the purpose of making one or more connections, providing a leak tight fluidic connection. Such an interface station may also service to make electrical connections.

The receiving station may (1) include ability to make one or more fluidic leak tight connections; (2) include ability to make one or more electrical connections; (3) contain regions allowing for optics or a path for allowing external optics access to the device; (4) have all wetted components that are disposable in nature and compatible with a means of sterilization; (5) have fluid that is isolated via various fluid regions inline valves or more preferably via a non-contact mechanism such as a pinch valve, or the pump may include a way to isolate flow, for example when use of a peristaltic mechanism is utilized (e.g., the wheel may be positioned to pinch a tube or pump tube closed); (6) have conduits, tubing and fluid components that link via barbed or compression fittings; and/or (7) encompass using welding and part melting for manufacturing fluid assemblies.

Cells and the bioactive materials may be presented to the device via several approaches. They may be injected via a robotic fluid handling platform or injection system or connected via biocompatible containers. Bioprocess containers include polymer bags, T-flasks, conical tubes, media bottles, well plates, or the like. These vessels may be one time use or reusable when proper sterilization is performed. Connections to the fluid delivery path may be achieved by compression seals, threaded connections, clamping compression, luer lock mechanisms, O-ring seals, friction seals, gaskets seals, clamping, or similar connections. In the case of pneumatic displacement, the container itself may be pressurized or be contained inside a pressurized vessel.

In some embodiments, the cells may be presented to the device by custom cartridges that interface to the pumping or fluid manipulation system.

Fluid Output

After electroporation, a mixture of all the fluid streams can leave the device via a fluid outlet. The solution may be transferred to sterile polymer bags, T-flasks, conical tubes, media bottles, well plates, or the like and allowed to recover at 37° C. The cells may then be re-suspended in standard tissue culture medium and plated for immediate use in cellular assays, cryopreserved for future use, or used as desired.

Electrodes with Temporal and Spatial Control of Electric Fields

The separation between electrodes located across the thickness of the fluidic device is small, therefore requiring an applied voltage of only a few volts to perform the electroporation. This contrasts with the need for voltages up to several thousand volts that are normally required for standard electroporation. For example, it is known in the literature that a transmembrane electric field of less than 1 kV/cm is required to porate the cell membrane (Weaver and Chizmadzhev, 1996). For a distance between the electrode pairs of 100 micrometers, this requires approximately a 5 V potential difference to porate an average mammalian cell in accord with the present device. Suitable voltage differences across a living mammalian cell include the following range: 0.1 V to 10 V. For example, for a distance between the electrodes of 100 micrometers this range corresponds to an electric field of 10 V/cm to 1000 V/cm.

The flow channel can have one or several electrically independent electrode pairs. For example, it can have four sets of electrode pairs. Connections to the electrodes are made by using clips or conduction adhesive to connect these to a variable-voltage power supply, function generator, computer via a data acquisition card or amplifier, or batteries with a voltage divider. An ammeter can be used to monitor the current flowing between any pair of electrodes for monitoring and controlling the process.

The electrodes can be configured to apply either a constant, pulsating, or continuously time varying voltage perpendicular to the direction of flow or along the direction of flow. If a pulsating voltage is desired, a pulse duration from about 0.01 millisecond to about 100 milliseconds is suitable. The plurality of electrode pairs can be patterned to create spatially and temporally varying electric fields. The electrodes may be patterned using a photomask in the photolithographic process or by a shadow mask in the sputtering or deposition process. Patterning allows for the fabrication of electrodes with varying geometric shape. The variation of the shape combined with the fluid flow characteristics provides for controlling the time that cells are subject to the electric field.

The invention provides for the ability to pattern electrodes at different locations on the surface of the flow channel that can be individually connected to various electrical sources, where the electrical sources can have different voltage and current characteristics. The disclosed planar fluid systems consisting of electrically insulating material(s) enable the patterning of various electrode structures.

In various embodiments, any one or more of the following can be done: (1) one or more pairs of electrodes can be activated with time-dependent voltage characteristics to open pores in the cells; (2) another pair or more of electrodes can be activated to drive charged molecules into cells; (3) yet another pair or more of electrodes can be used to measure the electrical properties of the cell-containing fluid; (4) another pair or more of electrodes can be used to concentrate nucleic acids or other molecules at the interface between fluid layers of varying conductivity; (5) another pair or more of electrodes can be activated to move the cells actively, or passively by a creating flow in the fluid, to a prescribed location in the flow channel for cell sorting or other purposes; and (6) another pair or more of electrodes can be activated to rotate the cells to increase the surface area exposed for electroporation.

Importantly, disclosed embodiments permit the application of an arbitrary time-varying voltage to different electrodes. The voltage signals can be formed by computer generation of the desired time varying waveform, which is converted to an applied voltage by digital to analog conversion and amplification to the desired voltage range.

A simple waveform could be a sinusoidal voltage of prescribed frequency. The amplitude of the waveform needs to be sufficient to permeabilize the cells. This, in some embodiments, is achieved with a voltage drop of approximately 1 V over the typical 10 micrometers size of a mammalian cell within the fluidic device. The voltage waveform could be about 5 V, with a range extending from 0.1 V to 100 V depending on the depth of the fluidic device (e.g., chip) and the ionic composition of the fluid layers. The frequency of the pulse depends on the impedance characteristics of the circuit, specifically on the capacitive aspects of the so-called double layer that is known to form at the surface of the electrode due to the presence of free moving ions in the aqueous solution as well as the resistance of the fluid, or fluid layers of varying conductivity. The impedance of the capacitive double layer depends inversely on the frequency. Consequently, the frequency is preferably around 10 kHz so that the impedance of the fluid layers dominates, leading to most of the voltage change occurring within the fluid layer and not at the electrode-electrolyte interface. The frequency may range from 100 Hz to 1 MHz depending on the fluidic device dimensions and the ionic composition of the fluid layers. The impedance of the circuit may depend on the ionic conductivity of the fluid layers. The resistance of the fluid scales inversely with the ionic concentration, while the double layer capacitance is proportional to the ionic concentration raised to some power. The circuit at the electrolyte-electrode interface is often approximated as a capacitor due to the double layer in parallel with a frequency dependent impedance that is in series with a resistance due to charge transferred across the electrode (referred to as the Randles equivalent circuit model). The ability to control the time variation of the voltage means that the current charging the double layer and the current due to charge transferred across the electrodes may be modulated according to the optimum configuration for electroporating the cells. The voltage waveform may also be composed of the sum of a sinusoidal wave in addition to a constant DC voltage offset, resulting in a net flow of current.

Another periodic waveform, according to some embodiments, has a short duration voltage to open pores followed by a lower voltage of longer duration to move charged molecules into proximity to the cells. The movement of the charged molecule can be due to an electrophoretic force, or due to electrophoresis from a net fluid motion induced by the electrodes, or due to a dielectrophoretic force on the charged molecule or cell.

The continuous repeating nature of the waveform is useful for the continuous flow systems. The applied voltage can vary from positive to negative or remain at zero or another constant voltage for portions of the waveform.

A waveform of arbitrary shape can be created by adding together any number of sinusoidal waveforms each with their own frequency and amplitude, in addition to a constant voltage offset.

The net time-average voltage can be chosen to be positive, negative, or zero, providing the ability to control the net direction of charge flow. This would be of utility for controlling surface electrochemistry on electrodes and for directing charged molecules in a chosen direction.

The waveform may also be chosen to open pores in the cells or cell nucleus, and allow time for diffusion of neutral molecules into the cells before another pore-opening voltage application.

In some embodiments, the spatial arrangement of sets of counterpart electrodes across the surfaces of the fluid channel allows creating an electric field within the fluid channel that varies as a function of time and position without a need for a user to create discrete electrical pulses (e.g., via multiple electrical control module providing a waveform to each set of counterpart electrodes, which can be a sinusoidal waveform for any set, and which can be different between the different sets).

Electrodes can be patterned by a variety of methods, including ink jet printing, silk screening, lithographic patterning, vapor deposition through a shadow mask and other methods for patterning electrical conducting material on a variety of substrates including plastics.

Manufacturing the Device

A person of ordinary skill in the art would understand that there are many ways of fabricating the device or parts thereof using various materials known in the art. Exemplary methods of fabricating the device are presented herein.

Some embodiments of the device are constructed from a three-layer stack of polymer substrates or plastics. All three layers may be laser cut with a small beam spot, high resolution $CO_2$ laser. The layers on which the electrodes are fixed may be cut from 1 mm thick acrylic slabs, creating opposite surfaces of the channel. A middle layer defines the distance between the electrode pairs. In some embodiments, the three dimensions of the layers are the same. In preferred embodiments, the central layer that defines the channel height is thinner than the outer two layers on which the electrodes are deposited and which provide the mechanical stability of the device. Although it is most practical for the layers to be the same in dimensions in the plane that the stream flows, these dimensions can be different from one another. One way to manufacture these layers is to use a laser to cut acrylic pieces similar in dimension to a microscope slide 25×75 mm, add fluid inlet slits or ports and add alignment holes to facilitate assembly. A thin film electrode (50 nm) of a gold (Au) is deposited by physical vapor deposition through a shadow mask on the inside surface of each acrylic piece. The middle layer polymer film with medical adhesive on each side is cut to shape and receives the corresponding alignment holes via the laser cutting process. After laser cutting, the three pieces are placed on a jig containing alignment pins corresponding to the alignment holes in each layer. The sandwich assembly is then compression-bonded in a press. This two-step process of laser cutting and compression assembly is amenable to mass production and allows for a cost-effective consumable to be created. The process can be used to manufacture hundreds of thousands of devices per year. This contrasts with many other types of standard non-electroporation microfluidic devices that typically require expensive capital equipment and a large number of chemical processing steps.

Alignment of the device layers may be conducted by optical positioning or a physical means such as alignment pins or structures. The device layers may have receiving features for use with a jig alignment piece or system. Alternatively, the alignment features may reside in the device layers as so no jig or peripheral alignment system is necessary. These may include pin-like structures or features that snap together.

The flow cell could also be produced by an injection molding process to form one or more of the three layers, where the volume can scale to millions of single-use devices per year, using one injection molding press with a multi-cavity mold.

This disclosure allows for architectures for manufacturing the device that are readily amenable to injection molding. In this device, all the layers may be formed via injection molding. The fluidic channel may be formed in one layer at full depth or, alternatively, the channel may span two or more layers, where the full depth is achieved upon assembly. Injection ports may be created via core pins. Alternatively, the fluid inlets may be added post molding as a secondary operation or structure. The layers may be molded from the planar surface or from the edges. Appropriate and efficient part release from the mold cavity is known in the art.

The molded layers may be assembled together through mechanical connection, adhesion, bonding, welding (including ultrasonic and laser), fusing, melting, or the like. Additionally, there may be another material between the layers for connection and sealing such as, but not limited to, a gasket, O-ring, washer, or the like. Alternatively, sealing can be achieved through press tight or bonding features.

Circular entrance ports can be connected with various fittings to conventional tubing such as that from an automated cell manufacturing platform. Low cost manufacturing methods are desirable because the flow cell and material that comes in contact with cell-containing media should typically be discarded after one use to prevent cross-contamination. There are many ways to injection mold including using one mold or more than one over molding technique. Multiple layers may also be bonded post molding using, but not limited to, such techniques as ultrasonic, laser, thermal heat compression, adhesion, or alike.

In some embodiments, the fluid channel may reside in one layer and the opposing sealing structure is a non-injected molded part such as a film, tape, or planar material containing necessary fluid inlets.

In some embodiments, the device may be created by three-dimensional printing or additive manufacturing processes. Other fabrication techniques include compression molding, casting, and embossing.

In some embodiments, devices are made from glass via lithography and wet or dry etching. Alternatively, the devices may be physically machine via computer numeric control (CNC) or ultrasonic machining.

In other embodiments, the devices can be made from various materials, such as, for example, where at least one layer is glass, where at least one layer is plastic, where one of the layers is optically transparent, or where the channel material is electrically insulating.

Manufacturing the Electrodes

The formation of patterned electrodes on the flow channel surface can be accomplished with a variety of readily available techniques and materials known in the art. Exemplary methods are presented herein.

One method is to use the process of sputtering for deposition of a metallic conducting layer such as gold, platinum, aluminum, palladium, other metals, or alloys of multiple metals. Gold-palladium is an example of a metallic alloy that can be used to compose the electrodes. The electrodes can be made of an optically transparent material to allow observation of the motion of the living cells in the fluid channel of the device. To generate transparent conducting layers, films of indium-tin oxide (ITO) are frequently used. After metal deposition, these conducting layers can be patterned by masking and etching to remove material where it is not wanted to form the desired patterned electrode shapes. Appropriate masks may be formed from photoresist using common photolithographic exposure processes.

One exemplary method for forming electrodes is to deposit electrically conducing films made of metals or other conducting layers such as ITO. By depositing them through a prepositioned mask, sometimes called a shadow mask, the masks are positioned in proximity to the surface to be coated so that the conducting layer reaches the surface only where previously opened regions have been formed in the mask. In addition, a related technique called "lift-off" can be used, in which a patterned photoresist layer can be used to shape the pattern of deposited conducing material. Another exemplary method for patterning deposited electrodes is ablation by laser or ion etching to remove metal to form the electrode pattern.

The deposition of layers of conducing ink can be performed by brushing or spraying, followed by heating to form patterned conducting films.

These thin film patterning processes are well known to those skilled in the art. In this case, the thickness of the films is desired to be in the range of from 5 nm to 5 micrometers, with a preferred range of from 10 nm to 100 nm.

In some embodiments of the device, electrodes can be formed by inlaying wires or metal bars in grooves formed in the support block instead of affixing the electrodes to the support blocks. In this embodiment, grooves are machined into the support block, for example a plastic support block, and the electrodes are metal. The wires bars van be formed of metals such as aluminum, nickel, copper, stainless steel, and may be gold plated. The wires or bars be glued into the groove or held by a tight compression fitting.

Some embodiments of a system include an electroporation device, fluid delivery system including a pump, temperature control and optical and electrical monitor of the cells to obtain real-time feedback on the cell modification process. Feedback can be obtained by monitoring the electrical current passing between the two electrodes to provide information about living cell modifications, imaging of the living cells to provide information about living cell modifications or monitoring fluorescence of the living cells to provide information about living cell modifications.

Some embodiments include a system for inserting a biologically active molecule into a living cell, which system includes an electroporation device capable of performing a cell modification process including inserting a biologically active molecule into a living cell contained in a fluid flow by flowing fluid including living cells and biologically active molecules through a channel between two electrodes, each electrode disposed on opposite sides of the channel; passing the cells through a space between the two electrodes in a single layer so a living cell in the fluid flow is maintained in a similar position as other living cells in the fluid flow as they pass between the two electrodes; and applying an electric voltage across the two electrodes while the living cell is passing between the two electrodes in a manner that prevents one living cell from shielding another living cell from the applied electric field, in which the strength of the electric field to which the living cell is exposed is sufficient to form pores within the membrane of the living cell through which the biologically active molecule can traverse the cell membrane, but not lyse the living cell; a fluid delivery system including a fluid source and a fluid pump in fluid communication with the electroporation device; an electrical current source in electrical communication with the pair of electrodes; a temperature control in thermal communication with in the fluid flow; and an optical and electrical monitor of the living cell capable of obtaining real-time feedback on the cell modification process.

One advantage to the electroporation device is the ability to optically and electrically monitor the cells to obtain real-time feedback on the cell modification process. In some embodiments of the device: a microfluidic electroporation system comprises an observation microscope. Accordingly, the fluid flow controller or voltage controller can be adjusted as required to optimize the process efficiency and cell viability. In some such embodiments, the microscope may be positioned so that it views a reservoir that contains biologically active material. For example, this could be nucleic acids. The fluid from input cell reservoir flows through the channel of the microfluidic electroporation device and across the field of view of the microscope, and into a cell collection reservoir, thus enabling the user make adjustments as necessary to improve the efficiency of transformation. As used herein, the cell collection reservoir refers to any vessels, bags, plates, dishes, or containers that are capable of collecting cells flowing out of the flow device.

Temperature control of the solutions or materials in contact with the fluids may be implemented at any instance(s) in the system, including heating and cooling. This may include static control or temperature cycling.

The device can be interfaced to a fluid delivery system. A fluid delivery system (e.g., a pump) operating with flow controller is configured to displace, preferably, indirectly displace, the fluid from the input cell reservoir to establish a fluid flow within the fluid path. The fluid displacement apparatus can provide positive and/or negative displacement of the fluid. The delivery pump includes mechanisms based on peristalsis, pneumatics (pressure displacement), hydraulics, pistons, vacuum, centrifugal force, manual or mechanic pressure from a syringe, and the like. Preferably, the fluid is indirectly displaced by the pump without the fluid directly contacting any of the moving parts of the apparatus, such as, for example, a peristaltic pump acting upon a fluid filled tube. Alternatively, a pneumatic displacement mechanism may be used where a head pressure displaces liquid from a pressurized vessel. Conversely, fluid may be directly displaced by an apparatus, when the fluid is displaced by directly contacting any of the moving parts of the apparatus, such as, for example, the plunger of a syringe pump.

In addition to common mechanical pumping mechanisms, such as syringe and peristaltic pumps, the fluid delivery means may include gravity driven or hydrostatic pressure driven liquid flow. Here the fluid containing vessel is positioned at a given height (relative to the device fluid outlet) to provide the desired flow rate. The fluid height is chosen based on the overall system fluid restriction circuit (e.g., cross-sectional area, internal diameters, and lengths of the fluid path). In addition to the device's internal flow path dimensions, external components, such as tubing internal diameters, may be chosen to obtain a desired restriction for controlling the flow rate.

The liquid containing vessel may accept application of controlled gas head-pressure to aid in the displacement of the liquid from the vessel to the device.

The fluid delivery system (e.g., pump) may include a flow sensor for monitoring the flow rate or the flow sensor may provide closed loop feedback to the pump control system. The closed loop feedback can ensure accuracy and reduce pulsing. The pump displaces fluid contained in flexible tubing to create a fluid stream. The system may operate with an inline flow sensor configured to directly measure the fluid flow rate as the fluid passes the sensor. The system, in some embodiments, includes a feedback control in communication with the fluid displacement apparatus and the inline flow sensor. The inline flow sensor measures the flow and communicates with a feedback control mechanism. Suitable types of flow sensor mechanisms include thermal pulse, ultrasonic wave, acoustic wave, mechanical, and the like. The inline sensor may be mechanical-based, electrical-based, motion-based, or microelectromechanical systems (MEMS)-based. The sensor mechanism may be thermal, ultrasonic or acoustic, electromagnetic, or differential pressure. One example of a sensor suitable for use in accord with the present disclosure is a thermal-type flow sensor where the sensor typically has a substrate that includes a heating element and a proximate heat-receiving element or two. When two sensing elements are used, they are preferably positioned at upstream and downstream sides of the heating element relative to the direction of the fluid (liquid or gas) flow to be measured. When fluid flows along the substrate, it is heated by the heating element at the upstream side and the heat is then transferred non-symmetrically to the heat-receiving elements on either side of the heating element. Because the level of non-symmetry depends on the rate of fluid flow and that non-symmetry can be sensed electronically, such a flow sensor can be used to determine the rate and the cumulative amount of the fluid flow. This mechanism allows the flow to be measured in either direction. In preferred embodiments, the temperature sensors and the heating element are in thermal contact with the exterior of the fluid transporting tube and as the fluid stream only contacts the internal surfaces of the tube, the fluid media avoids direct contact with the sensor and heating elements. This format type allows highly accurate and highly sensitive flow measurements to be performed.

Integration of Fluidic Cell Processing with the Electroporation Device

Figure 17:
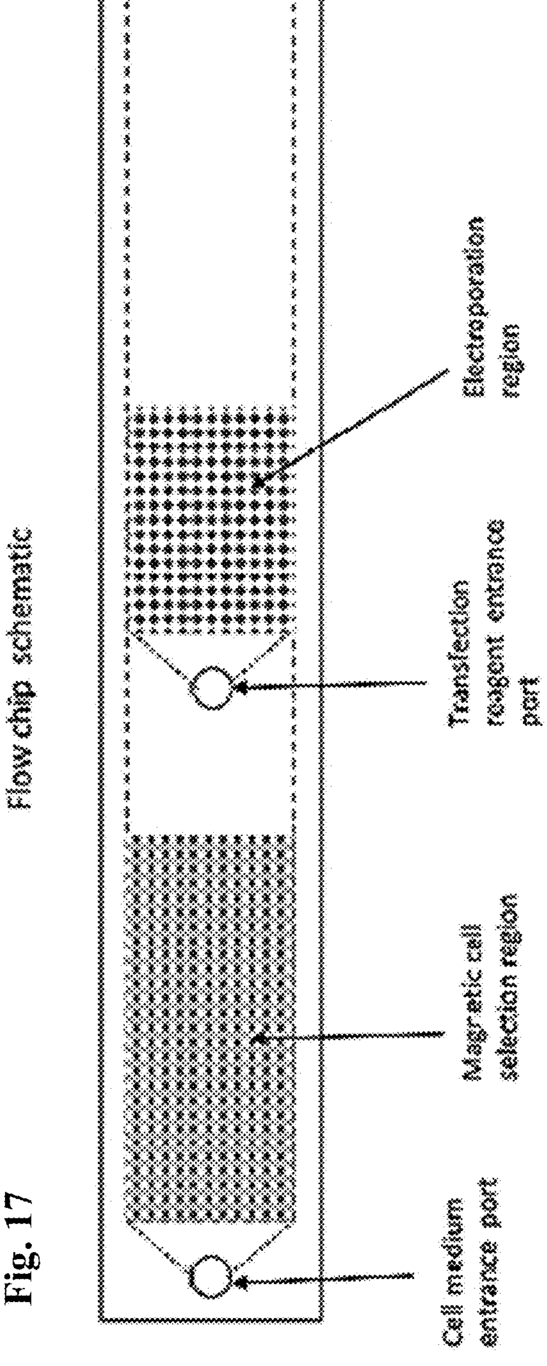
FIG. 17 shows a schematic of cell processing function that is integrated with a planar fluidic electroporation device (which, for example, can be a microfluidic chip or the like). The fluidic flow device schematic shows separate regions for magnetic cell selection and electroporation in a planar format.

Integration of fluidic cell processing with the electroporation device (e.g., chip) allows building greater function into a system. For example, the multi-channel flow device can incorporate the ability to utilize magnetic bead sorting approaches to select the cells to be processed by electroporation. As an example, FIG. 17 shows a fluidic flow device schematic depicting separate regions for magnetic cell selection and electroporation in a planar format.

Optical transparency of the flow device enables optical monitoring of the processes. Materials may include, but are not limited to, glass, quartz, polymer, metal films on substrate transparent substrates.

Selection of a variety of T-cells and B-cells can be achieved using magnetic beads conjugated with specific antibodies for the given cell type. There are several commercial manufacturers of superparamagnetic beads including Dynal and Seradyn of a variety of different sizes, typically between 2 and 5 microns. These beads can be used for the positive selection or depletion from flow of CD8+, CD3+, CD4+, and CD19+ cells, for example. The force (F) on a magnetic particle inside a magnetic field depends on the volume (V) of the particle, the difference in magnetic susceptibility between the particle and the surrounding fluid ($\Delta\chi$), and on the absolute strength and the gradient of the magnetic field (B): $F=V\cdot\Delta\chi(B\cdot\nabla)B$. By establishing a large magnetic field and a large magnetic field gradient within the fluidic device, cells that have bound magnetic beads conjugated with the appropriate antibody can be held stationary relative to the flow. In this case, the magnetic force must be stronger than the drag force on the bead from the flow and able to overcome the bead's random diffusive motion.

To establish the sufficient magnetic field within the fluidic device, small neodymium iron boron (NdFeB) magnets featuring magnetic flux densities of up to 500 mT at the pole surface can be placed in proximity to the planar surface. Commercially available versions of these magnets allow for the manipulation of magnetic particles or cells inside a microchannel even when the magnet is placed at several mm distance from the channel. Removing the magnet from proximity of the surface will release the cells. These magnets can be purchased in a variety of sizes ranging from 0.01 to 10 cm in diameter and different geometrical shapes including cylinders, cubes, rings, etc. Also, commercial electromagnets may be used to establish the necessary field and gradient though Joule heating from the relatively high current make these more problematic in small volume applications. It is also possible to fabricate an electrode on the planar surface by the deposition of a conducting metal like gold or platinum. Additionally, the magnetic field within the fluid can be enhanced in the presence of an external magnetic field by depositing and patterning magnetic metals (typically nickel or iron) within the fluid layer. Removing the magnet from proximity of the surface will release the cells. Alternatively, the device and or the magnetic source may be movable.

Measuring properties of cells upstream and downstream to measure the effectiveness of the electroporation. This requires flow and the ability to constantly monitor the electrical properties (e.g., resistance) of the cell-containing liquid. One could also monitor the change of resistance during the electroporating pulse, where the time-dependent I-V relationship would provide information on the effectiveness of the electroporation process. This is unlike other systems that may exist that do not monitor the effects during the continuous flowing process.

Post Electroporation Cell Manipulation: After electroporation, cells may be moved to an additional region in the device for secondary processing or transferred. The cells may be transferred from the device fluid outlet (or fluid interface component) to a sterile, multi-well dish or vessel and exposed to a secondary set of conditions. For example, to be exposed to for 30-40 minutes at 37° C. The cells are suspended in cell medium and either cultured for immediate use or cryopreserved.

The system may use magnetic bead or microfluidic pillar affinity separation to enrich selected cell types for electroporation and transfection. The input is white blood cells collected from the patient and the output is to a conventional cell culture bag for amplification.

Figure 18:
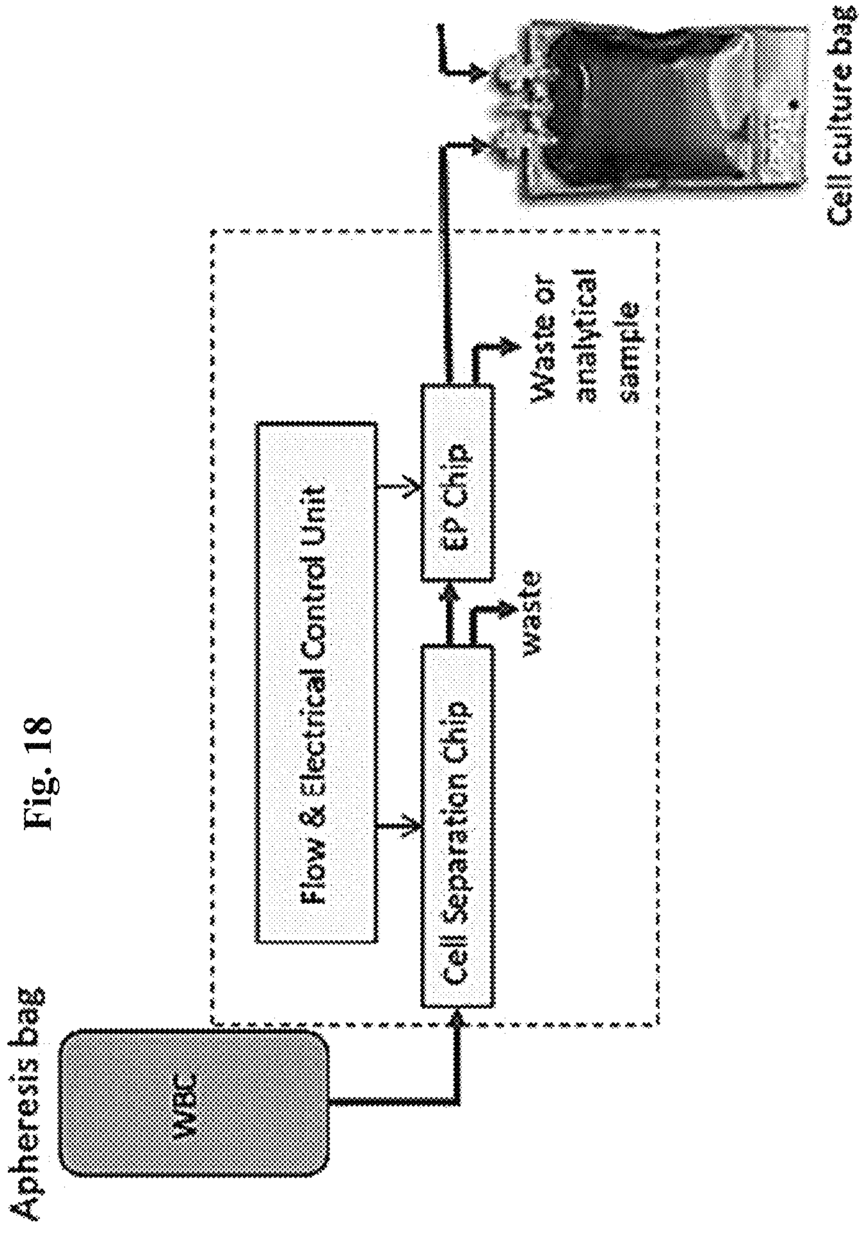
FIG. 18 shows a system of an independent microfluidic device and a planar electroporation device (e.g., an electroporation chip). In this figure, and in the rest of the disclosure, unless described otherwise in a particular context, the word "chip" is used interchangeably with the word "device" for facilitating the discussion of various aspects.
Figure 19:
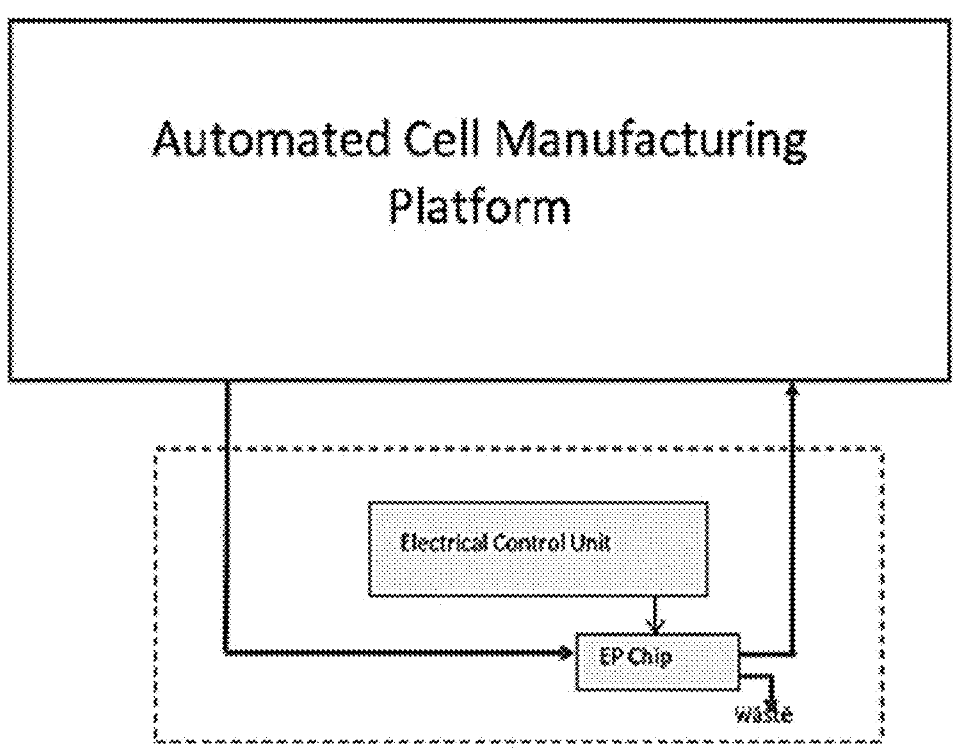
FIG. 19 shows an automated cell manufacturing platform that incorporates an electroporation system.

Example process and components are shown in FIG. 18. Additionally, the parts or portions of the process may be connected to other processing equipment or stages of a process. For example, in FIG. 19 the electroporation device and components may be implemented with more traditional cell processing hardware.

There is a need for improved methods for selecting the best receptor molecules with which to modify immune system cells for developing treatments for individualized and precisely targeted immunotherapies. Using a flow-based electroporation system it is possible to change the material that one provides to the inputs in time so that one can create many differing combinations of cells and inserted molecules for the purpose of creating libraries of candidate cell treatments for diseases such as cancer. By selection from this library doctors can select the best type of modified cell for treating a specific person's disease. In addition, our multi-input flow-bases electroporation system can be used to create or manufacture specifically designed combinations of cells with differing chemical modifications as prescribed for an individual patient. In this way, the disclosed methods can facilitate a highly individualized immunotherapy-based treatment of many differing types of cancer and disease.

Figure 20:
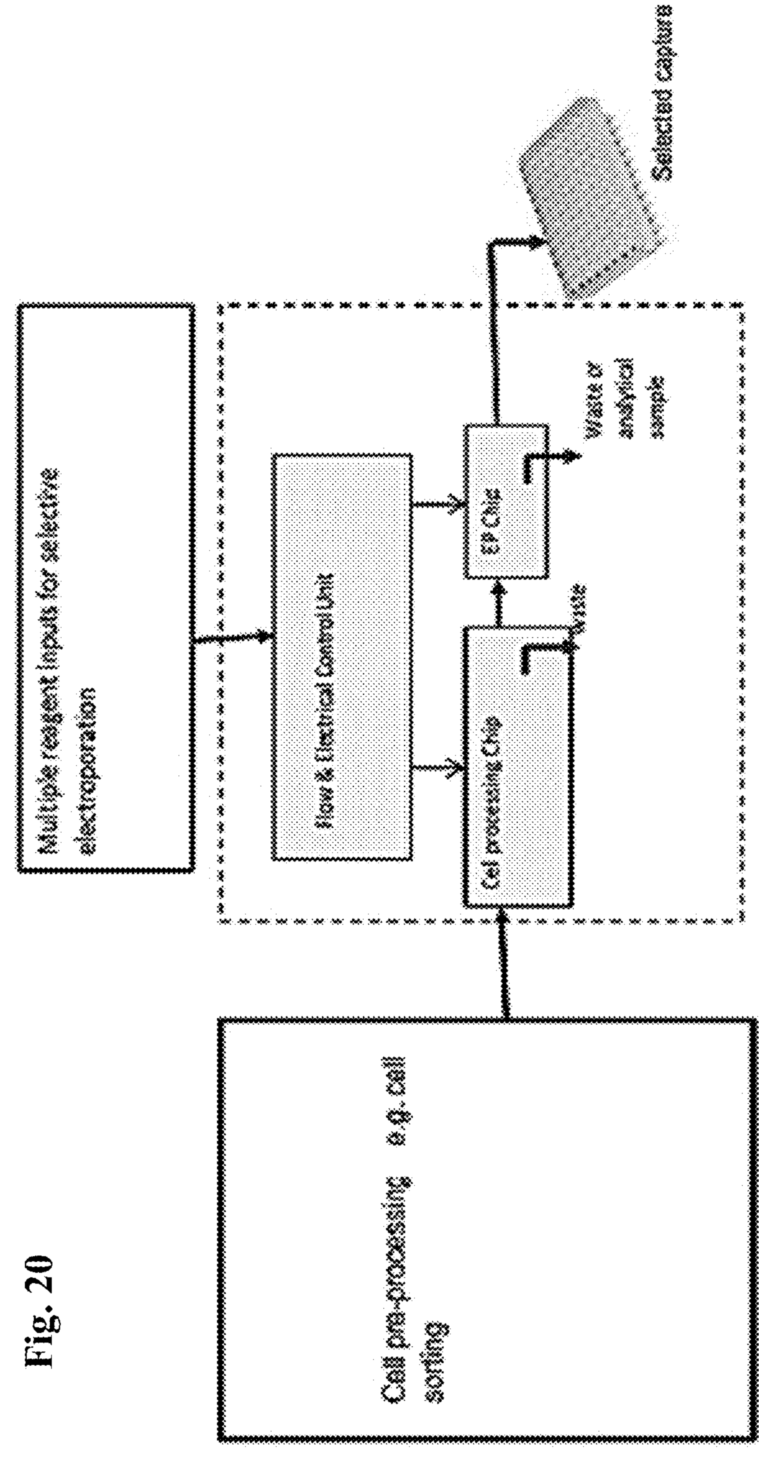
FIG. 20 shows a multi-flow device with dynamic control of processes to obtain optimum cell modification parameters.
Figure 21:
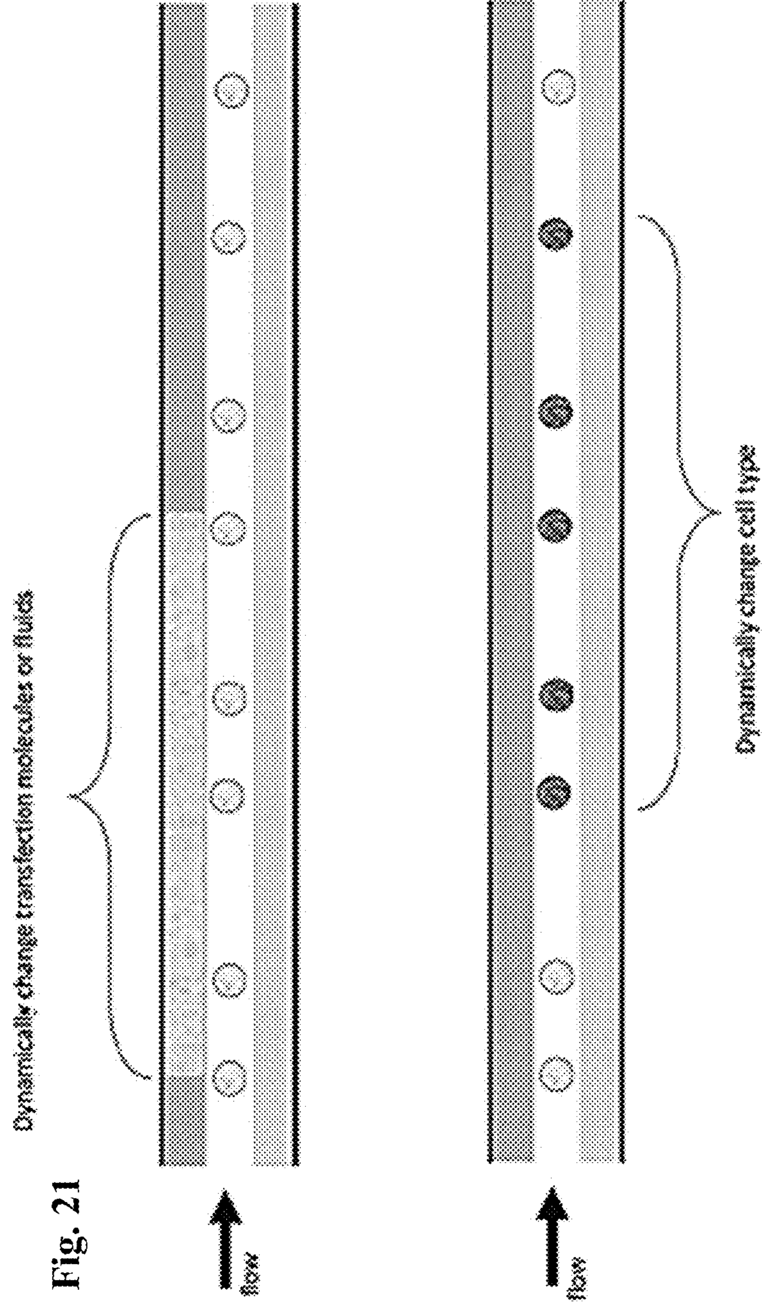
FIG. 21 shows a schematic of independently controlling and varying the chemical composition of three fluid streams for combinatorial processing.

Shown in FIG. 20 is a configuration of a versatile system for rapid controlled processing of cells in the electroporation device. There are numerous advantages that arise from the ability to control and vary the multiple fluid inputs during the electroporation process. By changing the composition of the various fluid streams as a function of time during the electroporation, and collecting the resulting material into different collection vessels, as shown in FIG. 20, it is possible to collect and evaluate a range of electroporation conditions to determine, for example, the best conditions for transfection of a particular cell type or to change the molecules in the stream to evaluate a range of biomolecules to determine which could be valuable for therapeutic use. Such a combinatorial process could greatly reduce the time required to test new compounds and develop cell-based therapies. FIG. 21 indicates that the chemical properties or contents of the fluid streams can be independently varied and controlled to controllably vary the electroporation conditions. Chemical compositions may include, but are not limited to buffers, salts, acids, bases, carbohydrates, peptides, proteins, lipids, and small drug molecules.

Another advantage of this capability is to enable handling small volumes of fluid or small samples of cells and reagents for research. This is particularly valuable in research where the cells may be rare, or the biomolecules may be rare or precious. Such volumes include picoliters, nanoliters, microliters, and milliliter volumes.

Independently controlling the composition of the fluid streams includes possible microfluidic integration of functions for pre and post processing. FIG. 17 shows fluid inputs at different positions along the flow channel. This enables, for example, different chemical conditions to be created before, during, and/or after electroporation. This can be done on the same device (e.g., chip) as show in FIG. 17 or on separate but connected chips as shown in FIG. 20. An important example of this capability includes treatment or selection of cells before electroporation.

Another important application is to maintain different chemical conditions for the cells before, during, or after electroporation. This is valuable, for example, because the conditions for effective electroporation and molecular transfer to the cell may be unhealthy or undesirable for the cells in the longer term. Therefore, changing the chemical composition of the fluid following electroporation enables changing the fluid conditions for the cells immediately after electroporation. This can be done, for example, by flowing in varying chemical-containing solutions such as a nutrient containing medium in which the cells can be maintained effectively for longer times. This nutrient medium can simply be introduced downstream of the electroporation region to dilute the fluid used during the electroporation and establish conditions in which the cells can remain viable or functional for a longer time.

There are numerous other capabilities for enhancing the value of electroporated samples by efficiently processing the material or maintaining different chemical conditions before or after the electroporation process in such integrated systems.

Shown in FIG. 21 is a diagram illustrating two possibilities for changing of input material in the flow streams to create selected and varying combinations of cells and reagents, to be combined to create modified cells.

Methods for Modifying or Determining Throughput of Electroporation

The time-dependent electric field and the chemical conditions to which the cells are subjected determine the fundamental electroporation conditions. According to the methods presented herein, such electrical conditions and chemical conditions can be identified efficiently for a flow-based microfluidic system and/or device. With this information, the methods of the present disclosure further allow reproduction of these fundamental conditions in a completely different system (different pumps and other hardware) or in a flow device with different electrode and/or channel dimensions that operates with different fluid flow rates and time dependent voltage applied.

This reproduces the fundamental conditions to which the cells are exposed but with selected higher or lower throughput or number of cells processed, keeping the composition of the fluids unchanged. This is possible because the flow devices with different dimensions can be readily fabricated and the fluid flow rates be easily modified, which is difficult to do with other approaches known in the art.

We can alternatively change, not reproduce, the fundamental electroporation conditions to increase throughput. These methods and parameters are also described below and in the working Examples presented herein. Such methods include varying, e.g., a cell concentration, chemical composition, and the time dependent electric field.

A Method of Modifying the Throughput of Electroporation

In some methods for increasing electroporation throughput, a parameter set is first determined by running a set of electroporation processes using small sample volumes. In some methods for increasing electroporation throughput, a parameter set is instead selected based on either previously or separately determined parameters or based on otherwise known parameters. These methods allow increasing the electroporation throughput while also allowing maintaining the same electroporation results, such as transfection efficiency and cell viability.

The overall parameter set includes a subset that need not be changed, and a subset that is changed. The subset that need not be changed can include voltage temporal waveform, a voltage amplitude, and a sample composition. The subset that is changed includes the volumetric flow rate and a channel width along the electrode pair. These two parameters in this changed subset are changed proportionally to each other: each by about the same factor (e.g., 2, 3, 4, 5, 6, 7, 8, 9, 10, 11, 12, 13, 14, 15, 16, 17, 18, 19, or 20, and any integer or non-integer values in-between).

When referring to any two values, parameters, factors, or levels being the "same," some amount of error is permissible. Therefore, for this disclosure, if to any two values, parameters, factors, or levels differ by at most 10%, they are the "same." As an example, if the volumetric flow rate for a small sample volume was 1000 microliters per second and the volumetric flow rate for the scaled-up process was 950 microliters per second, they are considered the same since the second one differs by less than 10% from the first (i.e., reference) one. Similarly, if flow rate is increased by a factor of 10, and the channel width along the electrodes is increased by a factor of 9, then they have been increased by the same factor (i.e., proportionally).

In some embodiments, the permissible error is less than 10% (e.g., 9%, 8%, 7%, 6%, 5%, 4%, 3%, 2%, or 1%). Therefore, for any embodiments referring to any two values, parameters, factors, or levels being the "same" without a specified amount of maximum error, that amount of maximum error is 10%, and for all such embodiments, alternative embodiments include lesser amounts of permitted maximum error values that can be specified (e.g., 9%, 8%, 7%, 6%, 5%, 4%, 3%, 2%, 1%, or any integer or non-integer values in-between).

The same methods used for increasing the throughput can also be used to decrease the throughput with appropriate adjustments (e.g., scale down of the volumetric flow rate and channel width, as compared to a scale up).

Another Method of Modifying the Throughput of Electroporation

In certain aspect, further provided herein is a method of modifying the throughput of electroporation using a microfluidic device, comprising: (a) proportionally increasing or decreasing the channel width and flow rate; (b) increasing or decreasing the cell concentration used during electroporation; (c) adjusting the fluid flow rate and time dependence of the voltage temporal waveform such that the cells are exposed to the same time-dependent electric field during passage between the electrodes before and after the adjustment; or (d) any combination of two or more of (a)-(c).

In some embodiments, (c) comprises proportionally increasing or decreasing the fluid flow rate and average number of waveform cycles experienced by the cells.

In some embodiments, the method comprises proportionally increasing or decreasing the flow cell channel width and flow rate thereby maintaining the same average linear flow velocity of the cells through the channel.

In some embodiments, proportionally increasing or decreasing comprises increasing or decreasing by the same factor with an error of at least 10%.

In some embodiments, the method decreases the throughput of electroporation.

In other embodiments, the method increases the throughput of electroporation.

In some embodiments, the method comprises the use of the flow device of the present disclosure.

In some embodiments, the flow rate is a volumetric flow rate.

In some embodiments, the voltage temporal waveform is a bipolar square wave, a dual voltage waveform, periodic waveform, or an arbitrary electrical waveform.

In some embodiments, the throughput of electroporation is modified (e.g., increased or decreased) by a factor of at least about 2, 3, 4, 5, 6, 7, 8, 9, or 10.

A Method of Determining the Throughput of Electroporation

In certain aspects, provided herein is a method of obtaining a desired throughput of electroporation using a microfluidic device.

Here, the throughput (V/T) is defined as the volume (V) of liquid electroporated per time (T). A microfluidic device can be designed and fabricated with certain dimensions to give a desired throughput, within the operating limits of the voltage control system and the fluid control system, that reproduces optimum electroporation conditions obtained without regard to throughput or device dimensions.

In some embodiments, the method of obtaining a desired throughput of electroporation using a microfluidic device comprises:

(a) selecting the desired volume (V) of liquid medium comprising cells to be electroporated and the desired time (T) to perform the electroporation with resulting desired throughput V/T; and (b) selecting the time dependent electric field that is desired to optimally perform electroporation for a particular molecule and cell type (e.g., determined from optimization or test experiments with the chosen cell type and molecule to be transported into the cell, without consideration of the throughput), and (c) calculating the fluid flow speed, S, through the electrode region of the microfluidic device that allows the time duration of the cells necessary for delivering the time-dependent electric field, and/or (d) adjusting the electrode dimensions of the microfluidic device such that the flow speed calculated in (c) occurs at a convenient value for the available fluid control system, and (e) selecting the channel height (H) of the device in the region of the electrodes that allows the desired time-dependent electric field determined in (b) to obtained with a voltage temporal waveform with amplitude within the capability range of the voltage source, and (f) constructing a microfluidic device with channel height (H), and channel width (W), and electrode dimensions such that H×W×S=V/T.

Heterologous Objects

In certain aspects, the methods and devices described herein are used to introduce a heterologous object into a cell. The heterologous object can be any object that is small enough to be encompassed by a cell (e.g., small enough to pass through the temporary pore created by electroporation). Such an object can be a nucleic acid (e.g., DNA, RNA), a protein, a peptide, a peptidomimetic, a bead, a dye, a chemical compound, and/or any object that is known in the art to have been introduced into a cell.

In some embodiments, the heterologous object is a nucleic acid. In some embodiments, the nucleic acid is DNA. In other embodiments, the nucleic acid is RNA. In some embodiments, RNA may comprise e.g., mRNA, RNP, small RNA (e.g., siRNA, miRNA, piRNA), RNAi agent, CRISPR/Cas agent (e.g., gRNA).

In some embodiments, the heterologous object modulates gene expression or modulates/alters the genome of a cell (e.g., creates a double-strand break, introduces into the genome a deletion, a substitution, an addition, a mutation (or corrects a mutation present in the genome), or a combination thereof). Systems for altering the genome (e.g., genomic sequence) is well known in the art. Non-limiting examples are provided below.

CRISPR/CAS

It is art-recognized that CRISPR/Cas system is effective in altering the genome. CRISPR/Cas systems are found in 40% of bacteria and 90% of archaea and differ in the complexities of their systems. See, e.g., U.S. Pat. No. 8,697,359 (incorporated by reference). The CRISPR loci (clustered regularly interspaced short palindromic repeat) are regions within the organism's genome where short segments of foreign DNA are integrated between short repeat palindromic sequences. These loci are transcribed and the RNA transcripts ("pre-crRNA") are processed into short CRISPR RNAs (crRNAs). There are three types of CRISPR/Cas systems which all incorporate these RNAs and proteins known as "Cas" proteins (CRISPR associated). Types I and III both have Cas endonucleases that process the pre-crRNAs, that, when fully processed into crRNAs, assemble a multi-Cas protein complex that is capable of cleaving nucleic acids that are complementary to the crRNA.

In type II systems, crRNAs are produced using a different mechanism where a transactivating RNA (tracrRNA) complementary to repeat sequences in the pre-crRNA, triggers processing by a double strand-specific RNase III in the presence of the Cas9 protein or a variant thereof. Cas9 is then able to cleave a target DNA that is complementary to the mature crRNA however cleavage by Cas9 is dependent both upon base-pairing between the crRNA and the target DNA, and on the presence of a short motif in the crRNA referred to as the PAM sequence (protospacer adjacent motif) (see Qi et al (2013) Cell 152: 1173). In addition, the tracrRNA must also be present as it base pairs with the crRNA at its 3' end, and this association triggers Cas9 activity.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The variants of Cas9 are art-recognized, e.g., Cas9 nickase mutant that reduces off-target activity (see e.g., Ran et al. (2014) Cell 154(6): 1380-1389), nCas, Cas9-D10A.

The requirement of the crRNA-tracrRNA complex can be avoided by use of an engineered "single-guide RNA" (sgRNA) that comprises the hairpin normally formed by the annealing of the crRNA and the tracrRNA (see Jinek et al (2012) Science 337:816 and Cong et al (2013) Sciencexpress/10.1126/science.1231143). Thus, exogenously introduced CRISPR endonuclease (e.g., Cas9 or a variant thereof) and a guide RNA (e.g., sgRNA or gRNA) can induce a DNA break at a specific locus within the genome of a target cell. Non-limiting examples of single-guide RNA or guide RNA (sgRNA or gRNA) sequences suitable for targeting are shown in Table 1 in US Application Publication 2015/0056705, which is incorporated herein in its entirety by reference.

In some embodiments, the gene editing nucleic acid sequence encodes a gene editing nucleic acid molecule selected from the group consisting of: a sequence specific nuclease, one or more guide RNA (gRNA), CRISPR/Cas, a ribonucleoprotein (RNP) or any combination thereof. In some embodiments, the sequence-specific nuclease comprises: a TAL-nuclease, a zinc-finger nuclease (ZFN), a meganuclease, a megaTAL, or an RNA guide endonuclease of a CRISPR/Cas system (e.g., Cas proteins e.g. CAS 1-9, Csy, Cse, Cpfl, Cmr, Csx, Csf, cpfl, nCAS, or others). These gene editing systems are known to those of skill in the art, See for example, TALENS described in International Patent Publication No. WO 2013/163628, and U.S. Patent Publication No. 2017/0191078 which are incorporated by reference in their entirety. CRISPR cas9 systems are known in the art and described in U.S. Pat. No. 10,266,850 filed on March 2013, and U.S. Pat. Nos. 8,697,359, 8,771,945, 8,795,965, 8,865,406, 8,871,445 (all of which are incorporated by reference). The devices and methods described herein are also useful for introducing into a cell the deactivated nuclease systems, such as CRISPRi or CRISPRa dCas systems, nCas, or Cas13 systems.

Guide RNAS (gRNAS)

In general, a guide sequence is any polynucleotide sequence having sufficient complementarity with a target polynucleotide sequence to hybridize with the target sequence and direct sequence-specific targeting of an RNA-guided endonuclease complex to the selected genomic target sequence. In some embodiments, a guide RNA binds to a target sequence and e.g., a CRISPR associated protein that can form a ribonucleoprotein (RNP), for example, a CRISPR/Cas complex.

In some embodiments, the guide RNA (gRNA) sequence comprises a targeting sequence that directs the gRNA sequence to a desired site in the genome, is fused to a crRNA and/or tracrRNA sequence that permit association of the guide sequence with the RNA-guided endonuclease. In some embodiments, the degree of complementarity between a guide sequence and its corresponding target sequence, when optimally aligned using a suitable alignment algorithm, is at least 50%, 60%, 75%, 80%, 85%, 90%, 95%, 97.5%, 99%, or more. Optimal alignment can be determined with the use of any suitable algorithm for aligning sequences, such as the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP, and Maq.

A guide sequence can be selected to target any target sequence. In some embodiments, the guide RNA can be complementary to either strand of the targeted DNA sequence. It is appreciated by one of skill in the art that for the purposes of targeted cleavage by an RNA-guided endonuclease, target sequences that are unique in the genome are preferred over target sequences that occur more than once in the genome. Bioinformatics software can be used to predict and minimize off-target effects of a guide RNA (see e.g., Naito et al. "CRISPRdirect: software for designing CRISPR/Cas guide RNA with reduced off-target sites" Bioinformatics (2014), epub; Heigwer et al. "E-CRISP: fast CRISPR target site identification" Nat. Methods 11:122-123 (2014); Bae et al. "Cas-OFFinder: a fast and versatile algorithm that searches for potential off-target sites of Cas9 RNA-guided endonucleases" Bioinformatics 30(10): 1473-1475 (2014); Aach et al. "CasFinder: Flexible algorithm for identifying specific Cas9 targets in genomes" BioRxiv (2014)).

In general, a "crRNA/tracrRNA fusion sequence," as that term is used herein refers to a nucleic acid sequence that is fused to a unique targeting sequence and that functions to permit formation of a complex comprising the guide RNA and the RNA-guided endonuclease. Such sequences can be modeled after CRISPR RNA (crRNA) sequences in prokaryotes, which comprise (i) a variable sequence termed a "protospacer" that corresponds to the target sequence as described herein, and (ii) a CRISPR repeat. Similarly, the tracrRNA ("transactivating CRISPR RNA") portion of the fusion can be designed to comprise a secondary structure similar to the tracrRNA sequences in prokaryotes (e.g., a hairpin), to permit formation of the endonuclease complex. In some embodiments, the single transcript further includes a transcription termination sequence, such as a polyT sequence, for example six T nucleotides. In some embodiments, a guide RNA can comprise two RNA molecules and is referred to herein as a "dual guide RNA" or "dgRNA." In some embodiments, the dgRNA may comprise a first RNA molecule comprising a crRNA, and a second RNA molecule comprising a tracrRNA. The first and second RNA molecules may form a RNA duplex via the base pairing between the flagpole on the crRNA and the tracrRNA. When using a dgRNA, the flagpole need not have an upper limit with respect to length.

In other embodiments, a guide RNA can comprise a single RNA molecule and is referred to herein as a "single guide RNA" or "sgRNA." In some embodiments, the sgRNA can comprise a crRNA covalently linked to a tracrRNA. In some embodiments, the crRNA and tracrRNA can be covalently linked via a linker. In some embodiments, the sgRNA can comprise a stem-loop structure via the base-pairing between the flagpole on the crRNA and the tracrRNA. In some embodiments, a single-guide RNA is at least 50, at least 60, at least 70, at least 80, at least 90, at least 100, at least 110, at least 120 or more nucleotides in length (e.g., 75-120, 75-110, 75-100, 75-90, 75-80, 80-120, 80-110, 80-100, 80-90, 85-120, 85-110, 85-100, 85-90, 90-120, 90-110, 90-100, 100-120, 100-120 nucleotides in length). In some embodiments, a nucleic acid or a composition thereof comprises a nucleic acid that encodes at least 1 gRNA. For example, the second polynucleotide sequence may encode between 1 gRNA and 50 gRNAs, or any integer from 1-50. Each of the polynucleotide sequences encoding the different gRNAs can be operably linked to a promoter. In some embodiments, the promoters that are operably linked to the different gRNAs may be the same promoter. The promoters that are operably linked to the different gRNAs may be different promoters. The promoter may be a constitutive promoter, an inducible promoter, a repressible promoter, or a regulatable promoter.

In some embodiments, a nucleic acid for integration into an endogenous locus is introduced in conjunction with another nucleic acid that encodes a Cas nickase (nCas; e.g., Cas9 nickase or Cas9-D10A). It is contemplated herein that such an nCas enzyme is used in conjunction with a guide RNA that comprises homology to an endogenous locus and can be used, for example, to release physically constrained sequences or to provide torsional release. Releasing physically constrained sequences can, for example, "unwind" the nucleic acid such that a homology directed repair (HDR) template homology arm(s) are exposed for interaction with the genomic sequence.

In some embodiments, zinc finger nuclease is used to induce a DNA break that facilitates integration of the desired nucleic acid. "Zinc finger nuclease" or "ZFN" as used interchangeably herein refers to a chimeric protein molecule comprising at least one zinc finger DNA binding domain effectively linked to at least one nuclease or part of a nuclease capable of cleaving DNA when fully assembled. "Zinc finger" as used herein refers to a protein structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

In some embodiments, a nucleic acid for integration described herein is integrated into a target genome in a nuclease-free homology-dependent repair systems, e.g., as described in Porro et al., Promoterless gene targeting without nucleases rescues lethality of a Crigler-Najjar syndrome mouse model, EMBO Molecular Medicine, (2017). In some embodiments, the in vivo gene targeting approaches are suitable for the insertion of a donor sequence, without the use of nucleases. In some embodiments, the donor sequence may be promoterless.

In some embodiments, the nuclease located between the restriction sites can be a RNA-guided endonuclease. As used herein, the term "RNA-guided endonuclease" refers to an endonuclease that forms a complex with an RNA molecule that comprises a region complementary to a selected target DNA sequence, such that the RNA molecule binds to the selected sequence to direct endonuclease activity to a selected target DNA sequence.

CRISPR/CAS9 and Variants

As art-recognized and described above, a CRISPR-CAS9 system includes a combination of protein and ribonucleic acid ("RNA") that can alter the genetic sequence of an organism (see, e.g., US publication 2014/0170753). CRISPR-Cas9 provides a set of tools for Cas9-mediated genome editing via nonhomologous end joining (NHEJ) or homologous recombination in mammalian cells. One of ordinary skill in the art may select between a number of known CRISPR systems such as Type I, Type II, and Type III. In some embodiments, a nucleic acid can be designed to include the sequences encoding one or more components of these systems such as the guide RNA, tracrRNA, or Cas (e.g., Cas9 or a variant thereof). In certain embodiments, a single promoter drives expression of a guide sequence and tracrRNA, and a separate promoter drives Cas (e.g., Cas9 or a variant thereof) expression. One of skill in the art will appreciate that certain Cas nucleases require the presence of a protospacer adjacent motif (PAM) adjacent to a target nucleic acid sequence.

RNA-guided nucleases including Cas (e.g., Cas9 or a variant thereof) are suitable for initiating and/or facilitating the integration of a nucleic acid delivered using the devices and methods described herein. The guide RNAs can be directed to the same strand of DNA or the complementary strand.

In some embodiments, the methods and compositions described herein can comprise and/or be used to deliver CRISPRi (CRISPR interference) and/or CRISPRa (CRISPR activation) systems to a host cell. CRISPRi and CRISPRa systems comprise a deactivated RNA-guided endonuclease (e.g., Cas9 or a variant thereof) that cannot generate a double strand break (DSB). This permits the endonuclease, in combination with the guide RNAs, to bind specifically to a target sequence in the genome and provide RNA-directed reversible transcriptional control.

Accordingly, in some embodiments, the nucleic acid compositions can comprise a deactivated endonuclease, e.g., RNA-guided endonuclease and/or Cas9 or a variant thereof, wherein the deactivated endonuclease lacks endonuclease activity, but retains the ability to bind DNA in a site-specific manner, e.g., in combination with one or more guide RNAs and/or sgRNAs. In some embodiments, the nucleic acid can further comprise one or more tracrRNAs, guide RNAs, or sgRNAs. In some embodiments, the de-activated endonuclease can further comprise a transcriptional activation domain.

In some embodiments, the nucleic acid compositions for integration of a nucleic acid of interest into an endogenous locus can comprise a hybrid recombinase. For example, Hybrid recombinases based on activated catalytic domains derived from the resolvase/invertase family of serine recombinases fused to Cys2-His2 zinc-finger or TAL effector DNA-binding domains are a class of reagents capable improved targeting specificity in mammalian cells and achieve excellent rates of site-specific integration. Suitable hybrid recombinases include those described in Gaj et al. Enhancing the Specificity of Recombinase-Mediated Genome Engineering through Dimer Interface Redesign, Journal of the American Chemical Society, (2014).

The nucleases described herein can be altered, e.g., engineered to design sequence specific nuclease (see, e.g., U.S. Pat. No. 8,021,867; incorporated by reference). Nucleases can be designed using the methods described in e.g., Certo et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; and 8,163,514, the contents of each are incorporated herein by reference in their entirety. Alternatively, nuclease with site specific cutting characteristics can be obtained using commercially available technologies e.g., Precision BioSciences' Directed Nuclease Editor™ genome editing technology.

MegaTALs

In some embodiments, the nuclease described herein can be a megaTAL. MegaTALs are engineered fusion proteins which comprise a transcription activator-like (TAL) effector domain and a meganuclease domain. MegaTALs retain the ease of target specificity engineering of TALs while reducing off-target effects and overall enzyme size and increasing activity. MegaTAL construction and use is described in more detail in, e.g., Boissel et al. 2014 Nucleic Acids Research 42(4):2591-601 and Boissel 2015 Methods Mol Biol 1239: 171-196. Protocols for megaTAL-mediated gene knockout and gene editing are known in the art, see, e.g., Sather et al. Science Translational Medicine 2015 7(307):ra156 and Boissel et al. 2014 Nucleic Acids Research 42(4):2591-601. MegaTALs can be used as an alternative endonuclease in any of the methods and compositions described herein.

CAR Molecules and CAR Therapy

The devices and methods of the present disclosure provide a particular utility for introducing a heterologous object into a cell for a CAR therapy. Chimeric antigen receptors (CARs) are transmembrane proteins that have been engineered to give the cells (e.g., T cells, macrophages, NK cells) the new ability to target/bind a specific protein. The receptors are chimeric because they combine both antigen-binding and certain cellular functions (e.g., T cell activating function) into a single receptor. For example, the receptor can comprise an extracellular antigen-binding domain (e.g., scFv) that binds to a specific antigen (e.g., those highly and specifically expressed on the surface of cancer cells) fused to a transmembrane domain and an intracellular costimulatory domain/activation domain.

CAR T Therapy

Chimeric antigen receptor T cells (CAR T cells) are T cells that are engineered to express the CAR proteins for cancer therapy. CARs enable T cells to recognize tumor-associated antigens (TAAs) in a major histocompatibility complex (MHC)-independent manner. CAR T therapy can use T cells that are autologous or allogeneic to the patient. After CAR T cells are infused into a patient, they act as a "living drug" against cancer cells. When they come in contact with their targeted antigen on a cell, CAR T cells bind to it and become activated, then proceed to proliferate and become cytotoxic. CAR T cells destroy cells through several mechanisms, including extensive stimulated cell proliferation, increasing the degree to which they are toxic to other living cells (cytotoxicity) and by causing the increased secretion of factors that can affect other cells such as cytokines, interleukins and growth factors. The first CAR T cell therapies were FDA-approved in 2017, and there are now 6 approved CART therapies.

There are several variations/generations of CAR designs. The first reports of tumor-targeting CARs demonstrated that an scFv recognizing antigens such as human epidermal growth factor receptor 2 (HER2) fused to the CD3 signaling domain can elicit tumor-specific cytotoxicity, but T cells expressing these "first-generation" CARs that included only the CD3 chain for T-cell signaling generally failed to elicit potent antitumor effects. In the following years, second- and third-generation CARs emerged that included one or two costimulatory domains, respectively, drawing from the biological understanding that the endogenous TCR requires association with other costimulatory or accessory molecules for robust signaling. Most commonly derived from CD28 or 4-1BB, these costimulatory domains conferred more potent antitumor cytotoxicity, increased cytokine production, and improved proliferation and persistence of CAR-T cells. The choice of costimulatory domain has an impact on a wide range of properties, including metabolic pathways, T-cell memory development, and antigen-independent tonic signaling, prompting further research into other costimulatory domains. For example, a third-generation CAR with OX40 and CD28 costimulatory domains repressed CD28-induced secretion of interleukin (IL)-10, an anti-inflammatory cytokine that compromises T-cell activity. In addition, the inducible T cell costimulator (ICOS) costimulatory domain in combination with either CD28 or 4-1BB costimulation increased in vivo persistence, and MyD88/CD40 costimulation improved in vivo proliferation of CAR-T cells. More recently, fourth-generation CARs that incorporate additional stimulatory domains, commonly referred to as "armored" CARs, have been reported. In one example, the engineered armored CAR-T cells termed "T cells redirected for universal cytokine-mediated killing" (TRUCK) have been engineered to secrete the proinflammatory cytokine IL-12 to stimulate innate immune cells against the tumor and resist inhibitory elements of the TME, including regulatory T (Treg) cells and myeloid-derived suppressor cells (MDSCs). The secretion of other soluble factors has been studied, including IL-15 or IL-18 to enhance T cell proliferation, as well as the combination of CCL19 and IL-7 to recruit endogenous immune cells and establish a memory response against tumors.

The devices and methods of the present disclosure can be used in introducing a nucleic acid to a T cell for generations of the CAR T cells for use as e.g., a cancer therapy.

Dual CAR Therapy

CAR T cells with ability to target two antigens on a cancer cell surface have been proven to be effective clinically. For example, CART cells with dual targeting of CD19 and CD22 in adult patients with recurrent or refractory B cell malignancies showed improved efficacy (Spiegel et al. (2021) *Nature Medicine,* 27:1419-1431).

In addition, dual CAR T demonstrated effectiveness in targeting tumor cells with heterogeneous antigen expression. For example, CAR-T cells targeting simultaneously two tumor-associated antigens with trans-acting CD28 and 4-1BB co-stimulation caused rapid antitumor effects in in vivo stress conditions, protection from tumor re-challenge and prevention of tumor escape due to low antigen density. Molecular and signaling studies indicated that T cells engineered with the dual CAR design demonstrated sustained phosphorylation of T-cell-receptor-associated signaling molecules and a molecular signature supporting CAR-T-cell proliferation and long-term survival. Furthermore, metabolic profiling of CAR-T cells displayed induction of glycolysis that sustains rapid effector T-cell function, but also preservation of oxidative functions, which are critical for T-cell long-term persistence (Hirabayashi et al. (2021) *Nature Cancer,* 2:904-918).

CAR-M Therapy

Programming CARs into cell types other than T cells can further expand the versatility of the therapy by realizing new functions unachievable by CAR T cells. It was recently demonstrated that primary macrophages can be engineered with CARS via adenoviral transduction (Klinchinsky et al. (2020) *Nat Biotechnol*). The resulting CAR M cells exhibited tumor-specific phagocytosis, inflammatory cytokine production, polarization of bystander macrophages to the immunostimulatory M1 phenotype, and cross-presentation of the tumor associated antigen (TAA) to bystander T cells.

CAR-NK Therapy

CD19-targeting CAR-NK cells have achieved robust clinical efficacy without inducing cytokine release syndrome (CRS), neurotoxicity, or graft-versus-host syndrome (GvHD) in patients with B-cell lymphoid tumors. CAR NK cells have been shown to exert potent and specific cytotoxicity toward a variety of tumor models, including leukemia, multiple myeloma, ovarian cancer, and glioblastoma, as well as toward immunosuppressive cell types such as myeloid-derived suppressor cells (MDSCs) and follicular helper T cells (TFH). Lastly, natural killer T (NKT) cells possess antitumor and tumor-homing capabilities, and GD2-targeting CAR NKT cells that harness these inherent advantages exhibited effective localization to and lysis of neuroblastoma cells without significant toxicity (Xu et al., (2019) Clin Cancer Res 25:7126-7138).

Exemplary Embodiments

1. A flow device for electroporation, comprising
   - a channel having a channel length, a channel height, and a channel width, wherein the ratio of said height to said width is less than about 0.1;
   - at least one inlet to allow a flow in the channel in a flow direction across the channel length;
   - at least one outlet to allow said flow from the inlet toward the outlet; and
   - at least one pair of electrodes disposed across the channel height.
2. The flow device of 1, wherein
   - (a) the channel is a planar channel;
   - (b) the device comprises at least 2 or at least 3 inlets;
   - (c) the device comprises at least 2 or at least 3 outlets; and/or
   - (d) the device comprises at least 2 or at least 3 pairs of electrodes, optionally wherein each pair of electrodes operate independently from each other.
3. The flow device of 1 or 2, wherein the channel height is at least about 50, 60, 70, 80, 90, or 100 micrometers, optionally wherein the channel height is about 100 micrometers.
4. The flow device of any one of 1-3, wherein the channel width is at least about 1, 10, 20, 30, 40, 50, 60, 70, 80, 90, or 100 millimeters, optionally wherein the channel width is about 10, 20, or 80 millimeters.
5. The flow device of any one of 1-4, wherein the channel width is the width of the channel along the pair of electrodes.

6. The flow device of any one of 1-5, wherein the channel width is uniform along the length of the channel.
7. The flow device of any one of 1-5, wherein the channel width is non-uniform along the length of the channel.
8. The flow device of 7, wherein the channel width is narrower near the inlet and the outlet as compared to the electrode length (e.g., FIG. 3B).
9. The flow device of any one of 1-8, wherein the channel height and the channel length are uniform along their respective dimensions.
10. The flow device of any one of 1-9, wherein the device comprises at least two inlets and at least one outlet, wherein the channel allows fluid to flow continuously in at least two fluid streams toward the at least one outlet, wherein the channel allows modulating the flow rate, chemical composition, or both the flow rate and chemical composition in the at least two fluid streams as a predetermined function of time, position, or both time and position.
11. A series of flow devices, comprising at least two flow devices of any one of 1-10, optionally which differ in the channel width.
12. The flow device of any one of 1-11, further comprising:
    (a) at least one fluid delivery system coupled to the flow device;
    (b) a flow sensor;
    (c) a flow-rate control module;
    (d) a temperature control module;
    (e) a fluid interface that couples the fluid delivery system to the flow device;
    (f) at least one voltage supplier;
    (g) at least one voltage control module;
    (h) a cell processing module;
    (i) a cell collection reservoir;
    (j) an electrical or optical monitoring module coupled to the flow device; or
    (k) any combination of two or more of (a)-(j).
13. The flow device of 12, wherein the at least one voltage supplier provides a voltage that has a bipolar square wave, a dual voltage waveform, periodic waveform, or a periodic arbitrary time-varying voltage.
14. The flow device of 13, wherein the at least one voltage supplier provides a voltage that has a period waveform.
15. The flow device of 14, wherein:
    (a) the periodic waveform is a sinusoidal function of time, wherein the sinusoidal function has an absolute amplitude from zero that is at most 200 Volts, a frequency that is at least 10 Hz and at most 100 kHz, and a phase that is at least 0 and at most 2n;
    (b) the periodic waveform has a first frequency and a second frequency different from the first frequency;
    (c) the periodic waveform is a Fourier series; and/or
    (d) the periodic waveform is a square waveform or a rectangular waveform having a voltage amplitude of at least 0.1 V and at most 100 V, and a frequency of at least 100 Hz and at most 1 THz.
16. The flow device of 15, wherein:
    (a) the square waveform or a rectangular waveform is bipolar; and/or
    (b) the square waveform or a rectangular waveform further comprises a direct current component of at most ±10 V.
17. The flow device of any one of 12-16, wherein the at least one voltage supplier
    (a) is connected to the at least one pair of electrodes independently from any other pair of electrodes; and/or
    (b) allows forming an electric field as a function of time and/or position within the fluid channel.
18. The flow device of any one of 12-17, wherein the flow device comprises at least two inlets and at least two fluid delivery systems, wherein each fluid delivery system is connected to a different inlet.
19. The flow device of 18, wherein the fluid delivery system allows modulating the flow rate and chemical composition in one of the at least two streams as a predetermined function of time, position, or both time and position independently from any other fluid stream within the channel.
20. The flow device of any one of 12-19, wherein the cell processing module is upstream from the flow device.
21. The flow device of any one of 12-20, wherein the cell processing module allows cell sorting, selection, labeling, analysis, or a combination thereof.
22. The flow device of any one of 12-21, wherein the cell processing module comprises a fluorescence-activated cell sorting component.
23. The flow device of any one of 12-22, wherein the cell processing module comprises a magnetic field source that allows magnetic bead separation.
24. The flow device of any one of 12-23, wherein the cell processing module is built in the device (e.g., FIG. 17) or built in another microfluidic device (e.g., FIG. 18).
25. The flow device of any one of 12-24, further comprising an apheresis bag upstream of the cell processing module.
26. A method of electroporating a cell, comprising flowing the cell through the flow device of any one of 1-25, and applying voltage to the electrodes.
27. A method of modifying the throughput of electroporation using a microfluidic device, comprising
    (a) proportionally increasing or decreasing the channel width and flow rate;
    (b) increasing or decreasing the cell concentration used during electroporation;
    (c) adjusting the fluid flow rate and time dependence of the voltage temporal waveform such that the cells are exposed to the same time-dependent electric field during passage between the electrodes before and after the adjustment; or
    (d) any combination of two or more of (a)-(c).
28. The method of 27, wherein (c) comprises proportionally increasing or decreasing the fluid flow rate and average number of waveform cycles experienced by the cells.
29. The method of 27, wherein the method comprises proportionally increasing or decreasing the flow cell channel width and flow rate thereby maintaining the same average linear flow velocity of the cells through the channel.
30. The method of any one of 27-29, wherein proportionally increasing or decreasing comprises increasing or decreasing by the same factor with an error of at least 10%.
31. The method of any one of 27-30, wherein the method decreases the throughput of electroporation.
32. The method of any one of 27-30, wherein the method increases the throughput of electroporation.
33. The method of any one of 27-32, wherein the method comprises the flow device of any one of 1-25.

34. The method of any one of 27-33, wherein the flow rate is a volumetric flow rate.
35. The method of any one of 27-34, wherein said voltage temporal waveform is a bipolar square wave, a dual voltage waveform, periodic waveform, or an arbitrary electrical waveform.
36. The method of any one of 27-35, wherein the throughput of electroporation is modified (e.g., increased or decreased) by a factor of at least about 2, 3, 4, 5, 6, 7, 8, 9, or 10.
37. A method of obtaining a desired throughput of electroporation using a microfluidic device, the method comprising:
   (a) selecting the desired volume (V) of liquid medium comprising cells to be electroporated and the desired time (T) to perform the electroporation with resulting desired throughput V/T; and
   (b) selecting the time dependent electric field that is desired to optimally perform electroporation for a particular molecule and cell type (e.g., determined from test experiments with the chosen cell type and molecule to be transported into the cell, without consideration of the throughput), and
   (c) calculating the fluid flow speed (S) through the electrode region of the microfluidic device that allows the time duration of the cells necessary for delivering the time-dependent electric field, and/or
   (d) adjusting the electrode dimensions of the microfluidic device such that the flow speed calculated in (c) occurs at an acceptable value for the available fluid control system, and
   (e) selecting the channel height (H) of the device in the region of the electrodes that allows the desired time-dependent electric field determined in (b) to obtained with a voltage temporal waveform with amplitude within the capability range of the voltage source, and
   (f) constructing a microfluidic device with channel height (H), and channel width (W), and electrode dimensions such that H×W×S=V/T.
38. The method of any one of 27-37, wherein the electroporation is used for manufacturing cells for cellular therapies.
39. The method of 38, wherein the cellular therapies comprise a CAR therapy.
40. The method of any one of 26-39, wherein the electroporation is used to transfect a heterologous object into a cell, optionally a mammalian cell.
41. The method of 40, wherein the cell is a human cell.
42. The method of 40 or 41, wherein the cell is a lymphocyte.
43. The method of any one of 40-42, wherein the cell is a T cell, optionally a primary T cell.
44. The method of any one of 40-43, wherein the heterologous object comprises a nucleic acid.
45. The method of any one of 40-44, wherein the heterologous object comprises an mRNA.
46. The method of any one of 40-45, wherein the heterologous object comprises a CRISPR/Cas9 RNP.
47. The method of any one of 26-46, wherein the method modifies a genome of the cell.

EXAMPLES

The disclosure will be further illustrated with reference to the following specific examples. These examples are given by way of illustration and are not meant to limit the disclosure or the claims that follow.

Example 1: Materials & Methods

Fabrication of Electroporation Flow Chips

Electroporation flow chips were constructed from a three-layer stack of polymer substrates. All three layers were laser cut with a small beam spot, high resolution $CO_2$ laser. The top and bottom layers, cut from 1 mm thick acrylic slabs (McMaster Carr, Robbinsville, NJ, USA), create the floor and sealing channel surfaces. The middle layer was a spacer that defines the channel depth and width and composed of a thin (typically 80 μm) polymer film with medical adhesive on each side (Adhesives Research, Glen Rock, PA, USA). To fabricate the chip, the bottom and top acrylic layers were laser-cut into 1"×2" pieces. The pieces were then laser-cut to add fluid inlet/outlet ports and alignment holes for use during the assembly process. Afterwards, a thin film electrode of gold was deposited by physical vapor deposition using a CVC SC4500 electron-gun evaporation system on the inside surface of each acrylic piece at the Cornell NanoScale Facility (CNF) using a shadow mask. The middle layer was cut to shape and also received the corresponding alignment holes via the laser cutting process. The three-piece (acrylic, polymer film, acrylic) sandwich assembly was then compression bonded in a press.

Cell Culture and Reagents

Primary T cells were purchased from StemCell Technologies and cultured in animal-product free ImmunoCult media supplemented with 100 μg/mL recombinant human IL-2 (StemCell, Vancouver, BC, Canada). Primary T cells were thawed, permitted to rest overnight in media, and subsequently activated with CD3/CD28 antibodies (StemCell) per manufacturer's instructions. Two-days post-activation, cells were harvested for transfection. Jurkat cells were purchased from Millipore Sigma (Millipore Sigma, Burlington, MA, USA) and cultured in RPMI 1640 medium supplemented with 10% fetal bovine serum (R&D Systems, Minneapolis, MN, USA). All cells were maintained at 37° C. and 5% $CO_2$.

DNA, mRNA, and CRISPR/Cas9 Constructs pCMV-GFP (plasmid DNA; 3705 bp) was purchased from Altogen Biosystems (Las Vegas, NV, USA). Dasher GFP mRNA (1 kb) was purchased from Aldevron. SpCas9 and sgRNA targeting the TRAC locus (AGAGUCUCUCAGCUGGUACA) were purchased from Synthego (Synthego, Pasadena, CA, USA). Ribonucleoprotein (RNP) complexes were formed by mixing equimolar quantities of SpCas9 and sgRNA and incubating for 10 minutes at room temperature before addition to cell suspensions in electroporation buffer.

Electroporation Procedure

For electroporation experiments, cells were harvested, counted, and washed two times in BTXpress Cytoporation low-conductivity electroporation buffer (Holliston, MA, USA). After the second wash, cells were resuspended in the same electroporation buffer at a density of $5\times10^6$ cells/mL unless otherwise noted. The cargo to be delivered was subsequently added at the indicated concentrations for each experiment. Aqueous solutions containing cells and cargo were then loaded into a syringe, which was then loaded into a syringe pump (Chemyx, Stafford, TX, USA). Cell suspensions were flowed continuously into the flow cell at 320 μL/min (2-mm channel width) or 1600 μL/min (10-mm channel width) unless otherwise noted. As cells transit under the electrode, they were subjected to the indicated arbitrary voltage waveform generated by a function generator (Siglent SDG 1032X; Siglent, Technologies, Solon, OH, USA) and amplified by a RF amplifier (TS250; Accel Instruments, Irvine, CA, USA). As cells exit the outlet, they are dispensed into wells containing pre-warmed cell media by a custom-built robotic fraction collector.

Throughout each experiment, the function generator and oscilloscope were controlled using a custom MATLAB program to deliver one to ten pre-programmed arbitrary voltage waveforms over the experiment's duration (v. 2021a, Mathworks, Natick, MA, USA). Waveform switching and the robotic autosampler were programmed to ensure that each well contained a pure population of cells that received one pre-programmed voltage waveform. Voltage waveforms and the voltage across a 1-ohm resistor in series with the flow chip were monitored by an oscilloscope (Siglent SDS1104X-E, Siglent Technologies). Transfection efficiency, cell viability, and relative yield were measured 24-h post-transfection (unless otherwise noted) by flow cytometry.

Flow Cytometry

Primary T or Jurkat cells were withdrawn 24-h (GFP expression) or 72-h (TCR-α) after transfection for flow cytometry analysis using a ZE5 Cell Analyzer (Bio-Rad, Hercules, CA, USA). TCR-α expression was measured by staining primary T cells using AlexaFluor 488 anti-human TCR-α antibody (BioLegend, San Diego, CA, USA). Viability was measured by staining cells with the viability dye 7-AAD and incubating for 5 minutes prior to flow analysis (Fisher Scientific, Hampton, NH, USA). During flow analysis, cells were first gated to exclude cell debris using forward scatter (FSC) area vs. side scatter (SSC) area plots. Single cells were subsequently gated using FSC-area and FSC-height plots. To measure viability, single cells were gated to measure the percentage of 7-AAD negative (live) and positive (dead) populations. To measure GFP or TCR-α expression, viable cells were gated to measure the percentage of cells with green fluorescence relative to zero-voltage controls.

Example 2: An Exemplary Device

An exemplary device incorporates a single use, continuous-flow microfluidic channel capable of efficient and reproducible electrotransfection of cells. The microfluidic channel consists of a planar flow chip with a thin slab geometry. Electrodes are patterned on the top and bottom flow surfaces in order to apply a uniform electric field perpendicular to the flow direction (FIG. 1A). The electric field is applied with a continuously cycling arbitrary voltage waveform. The thin channel height, ranging from 50-100 μm, ensures that each cell is subject to the same electric field and chemical environment to enable reproducible electroporation. The thin channel height also permits us to achieve the necessary electric field strength to transiently open pores in the plasma membrane using relatively low voltage amplitudes (5-30 V) compared to the high voltage of traditional commercial systems. The width (1-10 mm) of the devices used in these experiments is much larger than its depth to allow for rapid and continuous flow of the cells through the chip (FIG. 1B). Importantly, the width of the device can be greater than 10 mm and varied to match the desired experimental throughput without changing the electric field experienced by the cells. As such, our planar geometry enables optimal transfection parameters to be determined using small volumes and channel widths before scaling up to large volumes and channel widths for clinical-scale delivery.

The exemplary device is designed to integrate with automated cell processing approaches using a selectable, computer-controlled voltage waveform and robotic fraction collection. The device is capable of delivering any arbitrary electrical waveform. During typical operation, cells are driven into the channel by a syringe pump through a single fluid inlet and exit through a single fluid outlet (FIG. 1C). Cells are typically suspended in a low conductivity electroporation buffer containing the cargo to be delivered. To optimize electrotransfection, a custom MATLAB script controls a function generator containing pre-programmed electrical waveforms while a robotic autosampler is programmed to move the outlet tubing for dispensing in a multi-well plate (FIG. 1D). Electrical waveform selection and robotic autosampling are programmed such that each well contains a pure population of cells that received one pre-programmed voltage waveform. In this study, we focus on the use of bipolar rectangular waveforms that can be described by their frequency (f), duration (t), and voltage amplitude (V) (FIG. 1E). Overall, this robotic setup enables rapid sweeping of electrical parameters to select conditions desirable for transfection. Larger scale transfection is then performed with the selected electrical conditions.

Example 3: Electroporation of Mammalian Cells with a DNA Plasmid

This example describes an embodiment where the flow electroporation device is used to electroporate mammalian cells with a DNA plasmid. Chinese hamster ovary (CHO-K1) cells (ATCC) are electroporated with a plasmid that expresses green fluorescent protein using the flow-through electroporation device described. Cell viability can be determined based on the uptake of propidium iodide. The electroporation efficiency can be determined using fluorescent observation of the number of cells that express the green fluorescent protein relative to the total number of cells.

The cells are cultured in an incubator at 37° C. and 5% $CO_2$. The cells can be cultured in a synthetic medium, such as Dulbecco's modified Eagle's Minimum Essential Medium (DMEM, Sigma, St. Louis, MO) supplemented with 10% fetal bovine serum (Sigma) and 100 mg/mL streptomycin (Sigma). When the cell suspension density reaches a certain value, for example, $2\times10^6$ cells/mL, the cell suspension is diluted with additional culture medium. Prior to introduction into the device, a 10 mL sample of the suspension is centrifuged at 300 g for 5 min. The supernatant is discarded, and the cells are re-suspended in a low conductivity buffer (described below). The cell suspension density for electroporation is preferably $1\times10^8$ cells/mL with a range between $1\times10^7$ and $1\times10^9$ cells/mL.

The low conductivity buffer is composed of 0.8 mM $Na_2HPO_4$, 0.2 mM $KH_2PO_4$, 0.1 mM $MgSO_4 \cdot 7H_2O$, and 250 mM sucrose, at a pH of 7.4. This buffer is made by dissolving 0.1136 g of $Na_2HPO_4$, 0.0272 g of $KH_2PO_4$, 0.02465 g of $MgSO_4 \cdot 7H_2O$, and 85.575 g of sucrose in 1 liter of water, and subsequent adjustment of the pH. The sucrose is used to equalize the osmotic pressure of the buffer with that of the cells. The buffer is filtered with a 0.2-micron membrane and stored at 4° C. The concentrations of salts in the buffer as described result in a solution with electrical conductivity of approximately 0.014 S/m. The preferable range of the electrical conductivity of this buffer is between $1\times10^{-3}$ and 2.5 S/m.

The pAcGFP-C1 plasmid (4.7 Kb, Clontech, Mountain View, CA) encodes a green fluorescent protein (GFP) from *Aequorea coerulescens* and contains an SV40 origin for replication in mammalian cells. The GFP protein is excited at 475 nm and emits at 505 nm. The plasmid is amplified in *E. coli* and purified using the QIAfilter Plasmid Mega Kit (Qiagen, Valencia, CA) according to the manufacturer's instructions. The plasmid DNA is dissolved in Tris-EDTA buffer and stored at −20° C. until use. The plasmid DNA concentration is determined by ultraviolet (UV) absorbance at 260 nm. Prior to an electroporation experiment, the plasmid is precipitated with ethanol and resuspended in phosphate buffered saline (PBS, 137 mM NaCl, 2.7 mM KCl, 10 mM $Na_2HPO_4$, 1.8 mM $KH_2PO_4$) buffer with an electrical conductivity of approximately 1.5 S/m at a concentration of approximately 40 ug/mL. The range of the electrical conductivity of this buffer is between $1\times10^{-2}$ and 10 S/m. The range of the plasmid concentration is between 0.01 and 100 ug/mL.

The low electrical conductivity buffer used for the cell flow inlet used in combination with a higher electrical conductivity buffer (PBS) for the upper and lower sheath inlets and flow layers results in an electric field that is substantially larger across the cell flow layer for a given applied voltage. For a typical experiment, the pressure of each flow is adjusted so that the cell flow layer is approximately 50 microns deep and the upper and lower sheath flow layers are approximately 25 microns each in depth. The electrical conductivities of the low and high conductivity buffer are 0.014 S/m and 1.5 S/m, respectively. The electrical resistance of the sheath layer (for a voltage applied between the two support block surfaces) is approximately 99% of the total resistance. This means that if 5 V is applied between the electrodes on the two support blocks that the electric fields in the streams adjacent to the electrodes is approximately 9 V/cm while the stream sandwiched between those two streams is 991 V/cm.

It is known that a difference of approximately 1 V between the interior and exterior of a certain cell will result in the formation of pores that can allow for the passage of nucleic acid molecules. The potential difference U across a cell membrane at a point on the surface of a cell in an external electric field of strength E is given by $U=fER\cos\theta$, where R is the cell radius, θ is the angle between the electric field and the normal to the cell surface, and f is a geometric factor that is typically around 3/2. This implies that to form pores at the poles of the cell the electric field should be about 1 kV/cm for a cell with radius of 8 microns.

With this electroporation device, the application of a 5 V potential difference between the top and bottom plates results in an electric field within the cell flow layer of about 1 kV/cm given the electric field strengths and flow layer depths described. The preferable range of applied voltages is between 1 V and 100 V. If the patterned electrodes are 2.5 cm by 0.5 cm in size, then for a 5 V applied potential, a current of about 0.17 A is generated and a power of 0.87 J/s is dissipated. This amount of power would increase the temperature of pure water in a device with dimensions 5 cm by 2.5 cm by 0.01 cm by 1.7 degrees C./s, assuming that no heat is dissipated through the boundary. The source for the applied voltage can be from a battery with a fixed voltage or a battery used in conjunction with a resistive voltage divider to enable the voltage to be varied over the selected range. Commercial voltage supplies are also readily available to provide selected voltages in the range of 1 V to 100 V. An alternative electrode size example includes electrodes with dimensions of 2.5 cm by 0.05 cm in size, then for a 5 V applied potential, a current of about 0.017 A is generated and a power of 0.087 J/s is dissipated. This amount of power would increase the temperature of pure water in a device with dimensions 5 cm by 2.5 cm by 0.01 cm by 0.17 degrees C./s. In a typical experiment, cells at a density of $1.0\times10^7$/mL are flowed through the device (e.g., chip) at a volumetric rate of approximately 1.5 mL/min, with a preferable range between 0.01 and 100 mL/min. The nominal flow rate of 1.5 mL/min results in an average linear flow velocity of 1.0 cm/s. At this velocity, cells are subject to the electric field from an electrode that is 2.5 cm by 0.5 cm in width and length for 0.5 s. Assuming Hele-Shaw flow, the pressure difference across the input and output of the device (e.g., chip) is about 40 atm. It is important to note that during the approximately 0.5 s that cells are subject to the electric field, that the plasmid DNA is electrophoretically driven toward the cell flow layer, assuming that the plasmid is in the lower sheath flow and that the top electrode is held at a higher voltage than the bottom electrode. Assuming a DNA mobility of $4\times10^4$ $cm^2/Vs$, the average time that it takes a DNA molecule to move half-way through a distance of 25 microns (the typical depth of the sheath flow layer containing the plasmid) is 0.34 s. A DNA molecule that reaches the cell flow layer is driven across it in about 10 ms.

Another important timescale is the cell sedimentation time for falling a distance of one-half of the cell flow layer thickness. Again assuming a cell radius of 8 microns, a difference in density between a cell and the surrounding fluid of 0.07 $g/cm^3$, and that the hydrodynamic friction coefficient of a cell is $6\pi\eta R$, where η is the buffer viscosity (approximately 0.001 Pa, but may be higher with additive chemicals such as sucrose), the time to drop a distance of 25 microns is approximately 0.4 s. And the time for a typical salt ion, such as Na or K, to diffuse a distance of 25 microns is 0.6 s. This indicates that the flow layers remain laminar (and retain their respective conductivities) for the time it takes the cells to cross the electrode region when the patterned electrodes are about 2.5 cm by 0.5 cm in width and length.

Following the electroporation of a given volume of cells the electroporation efficiency and cell viability are determined by phase contrast and static fluorescent imaging, and sometimes by flow cytometry. After the cells are electroporated with the GFP-expressing plasmid in the flow device (e.g., chip), the cells are collected and transferred to a 96 or 24 well plate with appropriate cell medium, such as DMEM. The cells are cultured at 37° C. in an incubator with 5% $CO_2$ for 1, 6, 12, 24, or 48 hours. The cells are centrifuged at 300 g for 5 min and the aspirant is discarded. The cells are washed with PBS and this process is repeated. Following this, the cells are stained with propidium iodide (Invitrogen) at a concentration of approximately 1 microgram/mL. The cells are incubated in the dark for 15 min and then optically examined by phase contrast under fluorescent filters. A standard GFP filter set is used to determine the fraction of cells that have been electroporated with the plasmid. A filter set with excitation at 488 nm and emission at approximately 620 nm is used to determine the dead cells that have been permeated by propidium iodide. Several images can be acquired at different locations to improve the statistics of the electroporation efficiency and the cell viability. The cells may also be examined by flow cytometry to determine the fraction that has been electroporated as identified by a green fluorescent signal and the fraction that are dead as identified by uptake of propidium iodide and a red fluorescent signal.

Thus, the described device can reliably be used to electroporate a large number of mammalian or bacterial cells at high efficiency and with low cell death in a short amount of time. The cells can be transfected with plasmid DNA that can be transcribed into a protein that is therapeutic for a disease. The cells can be transfected with mRNA that is likewise transcribed into a protein that is necessary for improving the health of the cell or that can be harvested for other medical use, such as production of antibodies. The cells can also be transfected with purified Cas9 protein, or another DNA guided nuclease, and synthetic guide RNA molecules, termed ribonucleoproteins, to efficiently edit a genomic site that is deleterious.

Example 4: Electroporation of Different Types of Cells and Molecules

The method outlined in Example 3 can be used to electroporate a variety of different mammalian cell types including: CHO, Hela, T-cells, CD8+, CD4+, CD3+, PBMC, Huh-7, Renca, NIH 3T3, Primary Fibroblasts, hMSCs, K562, Vero, HEK 293, A549, B16, BHK-21, C2C12, C6, CaCo-2, CAP-T, COS-1, Cos-7, CV-1, DLD-1, H1299, Hep G2, HOS, Jurkat, L5278Y, LNCaP, MCF7, MDA-MB-231, MDCK, Mesenchymal Stem Cells, Min-6, Neuro2a, NIH3T3L1, NSO, Panc-1, PC12, PC-3, RBL, RLE, SF21, SF9, SH-SY5Y, SK-MES-1, SK-N-SH, SL3, SW403, THP-1, U205, and U937.

The method outlined in Example 3 can be used to electroporate a variety of different types of molecules to any mammalian cell including: DNA, RNA, mRNA, siRNA, miRNA, other nucleic acids, proteins, peptides, enzymes, metabolites, membrane impermeable drugs, cryoprotectants, exogenous organelles, molecular probes, nanoparticles, lipids, carbohydrates, small molecules, and complexes of proteins with nucleic acids (like CAS9-sgRNA). While the method outlined in Example 3 relies on an electric field to deliver charged nucleic acid molecules to electroporated cells, the method also suffices to electroporate neutral molecules where diffusive motion is sufficient for the delivery.

Example 5: Electroporation Using Time Varying Voltage Waveforms

The method outlined in Example 3 can be used to electroporate cells with a variety of different voltage waveforms applied. Cells can be electroporated when applying a rectangular waveform with a frequency of 10 kHz and a peak to peak voltage difference of approximately 10 V. The preferable range of the peak to peak voltage difference is between 0.1 and 100 V. The preferable range of the frequency is between 100 Hz and 1 THz. The square wave could be bipolar so that the time averaged current is zero. The square wave could also have an additional DC component of preferably less than plus or minus 10 V. The applied waveform could be sinusoidal, saw-tooth, rectangular, triangular, or be a sum of any number of sinusoidal shapes with different frequencies and amplitudes in time.

The method outlined in Example 3 can be used to improve the efficiency of cellular electroporation by the application of different voltage waveforms to different electrode pairs. A first electrode pair could be used to apply a square waveform with a frequency of 10 kHz and a peak to peak voltage difference of approximately 10 V to permeabilize the membranes of the cells passing in the fluid channel. A second or third or more pair of electrodes could be used to apply a DC or oscillating voltage that preferentially directs charged molecules, like nucleic acids, toward the permeabilized cells. The second or third or more pair of electrodes could be used to exert electric forces on the cells or molecules in solution, which creates a relative velocity between the cells and the fluid, the molecules and the fluid, or between the cells and charged or neutral molecules in solution. The preferred range of the voltage amplitude or offset applied by the second or more pair of electrodes is between 1 mV and 100 V. The second or more pair of electrodes could be used to apply electrical forces that are along the direction of flow in the device or perpendicular to the direction of flow. Pairs of electrodes that are used to exert electric forces may be on the same surface or opposite surfaces of the device, where each surface is in contact with the fluid. The second pair of electrodes may be used to permeabilize structures within the cell after the membrane has been porated. The second or more pair of electrodes may be used to apply electric fields that result in the concentration increase of nucleic acid or other molecules at the interface between fluid layers of varying conductivity. The second or more pair of electrodes may be used to apply electric fields that cause the rotation of the cell so more surface area is exposed to the nucleic acid or other molecules in solution.

Example 6: Buffer Exchange

In some instances it may be desirable for the cells to be transported into the device in one buffer, and then to exchange that buffer within the device for another buffer more suitable for electroporation. It may also be advantageous after the cells have been subject to an arbitrary voltage waveform in the electroporation buffer, to exchange the electroporation buffer for a third recovery buffer that enhances the ability of the cells to recover (increases their viability). The first buffer may be cell media or a high conductivity buffer of a suitable pH. The electroporation buffer may be lower conductivity and of a different chemical composition and pH. The third, recovery buffer, may be identical to the first buffer or may also contain additional chemicals that aid in cell recovery.

A method to exchange buffers within the fluidic device is to have another inlet and outlet somewhere downstream from the first inlet, most likely on opposite sides of the fluid channel from each other. The second inlet and outlet pair may be directly opposite each other or offset. A pump or fluid control module flows the electroporation buffer into the second inlet. Fluid is directed toward a waste container from the second outlet pair. The fluid in the device at this location is now a mixture of the first buffer and the electroporation buffer. The mixture depends on the input flow of the first buffer, the input flow rate of the electroporation buffer, and the output flow rate through the second outlet. It may be necessary to repeat this process with additional inlet and outlet pairs to continue to exchange the composition of the fluid from the first buffer to the electroporation buffer. It is possible that cells may also be lost to the outlet. It may be preferable to have the inlet on the floor side of the fluid channel and the outlet on the ceiling side with the outlet downstream of the inlet, so that the cells preferentially sediment by gravity toward the floor before encountering the outlet, such that this loss is minimized. In this case the distance between the inlets are set by the time for the cells to sediment a distance proportional to the channel height. It is possible that all of the inlets utilized for the buffer exchanged are connected to the same fluid control module. The same system described for exchanging buffer by inlet and outlet pairs could be used downstream of the region in which the cells are subject to an arbitrary voltage waveform to exchange the electroporation buffer for a recovery buffer. It is also conceivable that the molecules to be electroporated into the cells are contained in one of the secondary exchanged buffers.

Example 7: Seamless Scale-Up of Transfection of Primary Human T Cells

In one demonstration, we performed electroporation of human immune system cells, inserting into the cells an RNA molecule that transfected the cells in an identifiable way by causing them to express green fluorescent protein (GFP). In this demonstration, the low volume chip had a channel width of 2 mm while the large volume chip had a channel width of 10 mm. Increasing channel width and flow rate by a factor of 5 resulted in a 5-fold increase in throughput, nearly identical electroporation conditions, and nearly identical GFP expression and viability. This proves the scaling possibilities of our device, system, and approach. Scaling width and flow by a larger factor would proportionally increase the throughput.

Figures 4A, 4B, 4C:
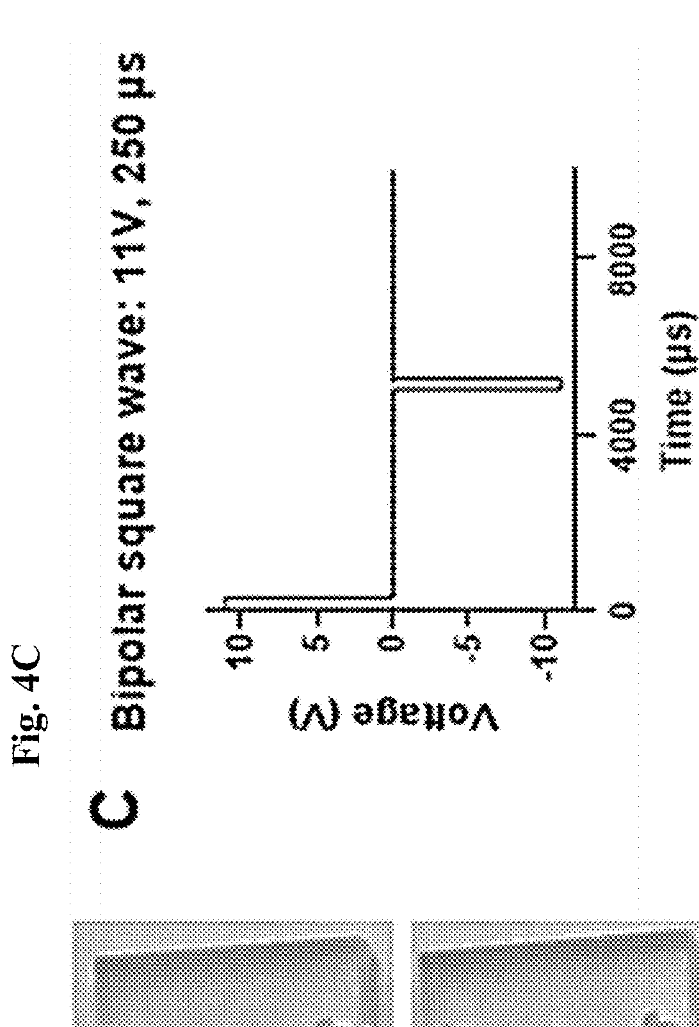
FIG. 4A-FIG. 4F: Seamless scaled-up delivery of mRNA to primary T cells.

To demonstrate our ability to scale up transfection within the CyteQuest system, we tested the electroporation of primary T cells (StemCell) with Dasher mRNA coding for GFP (Aldevron) in 2-mm and 10-mm wide channels (FIG. 4A-FIG. 4B). Primary T cells are cultured in an incubator at 37° C. and 5% $CO_2$ and cultured in animal-product free ImmunoCult media supplemented with 100 μg/mL recombinant human IL-2 (StemCell). Cells were thawed, permitted to rest overnight in media, and were subsequently activated with CD3/CD28 antibodies (StemCell). Cells were expanded eight-fold on day three post-activation and harvested for transfection on day five post-activation.

Harvested cells were withdrawn from the cell suspension, counted, and washed two times in a proprietary, low conductivity electroporation buffer. After the second wash, cells were resuspended in electroporation buffer at a density of $5\times10^6$ cells/mL. mRNA is subsequently added to bring the concentration to 40 μg/mL.

The aqueous solution containing cells and mRNA was loaded into a syringe which is then loaded into a syringe pump. Cells were flowed at 320 μL/min for the 2-mm channel width and 1600 μL/min for the 10-mm channel width (five-fold increase). Cells were collected into either 6-well plates (2-mm channels) or T75 flasks (10-mm channels) in 1-minute intervals. As a control, non-electroporated cells were collected first by keeping the electricity off. After collecting a control fraction, the electricity was switched on. Five electroporated fractions were collected over five minutes for both channel widths into separate wells/flasks with a seeding density of $5\times10^5$ cells/mL.

Figure 4D:
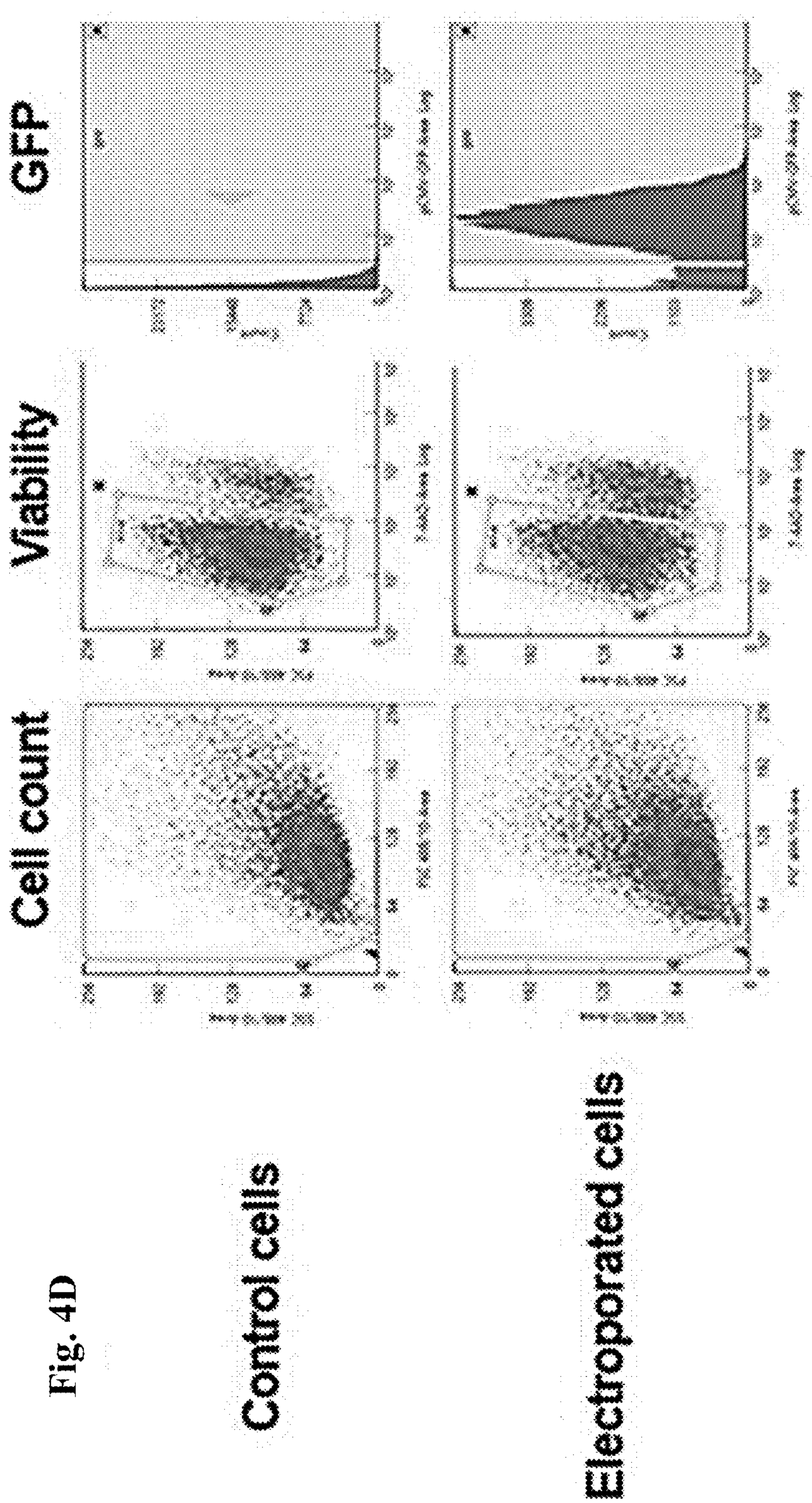

The experimental waveform for electroporation was identical in both channel widths and selected from previous optimization experiments. The waveform was a bipolar square wave with a positive and negative polarity pulse of equal duration (FIG. 4C). The waveform had an amplitude of 11V, pulse duration of 250 μs, period of 10 ms, and repeats at 100 Hz. With the given flow rate and waveform period, cells received on average 3 waveforms during their transit under the electrode. After electroporation, cells were immediately incubated at 37° C. and 5%. Cell count is measured by excluding debris through forward and side scattering signal via flow cytometry (FIG. 4D). Cell viability was measured by incubation with the 7-AAD viability dye and measurement of positive staining cells via flow cytometry (FIG. 4D). Transfection efficiency was measured by live-gated GFP positive cells via flow cytometry (FIG. 4D). Transfection efficiency and viability were measured at 6-, 24-, 48-, 72-, and 96-h post-transfection.

Figure 4F:
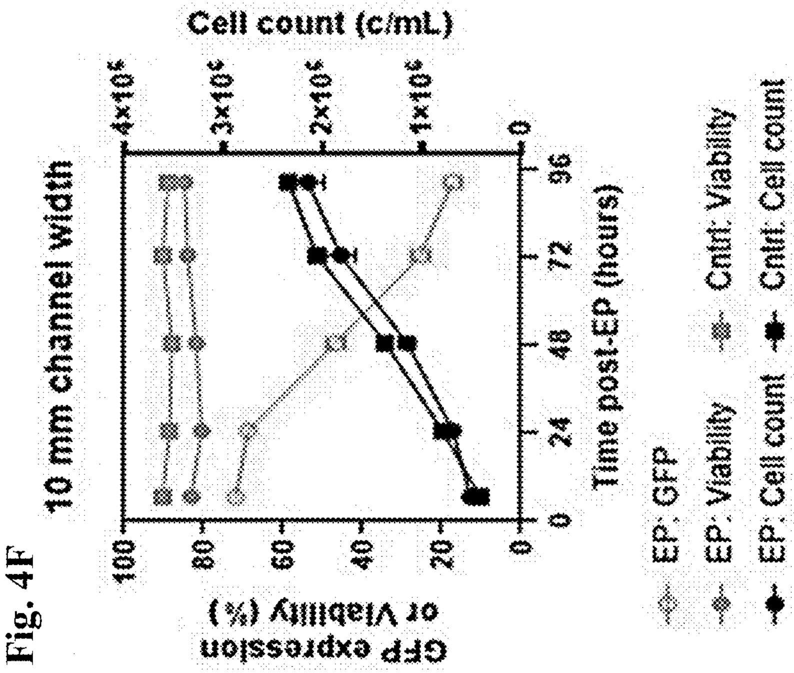
Figure 4E:
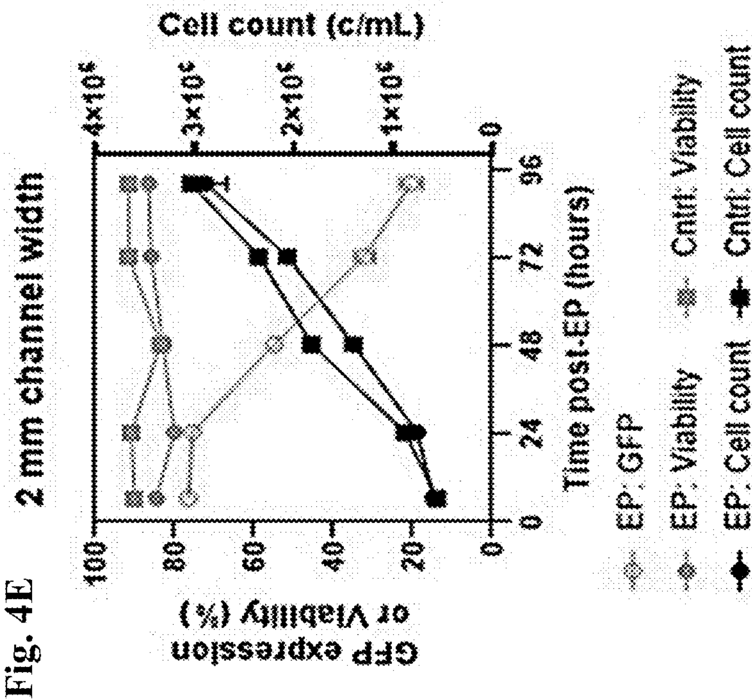

Measurements of both transfection efficiency and viability are roughly identical between the 2-mm and 10-mm channel widths (FIG. 4E). Cell proliferation, as measured by the change in cell count over time, was identical between electroporated and control cells in both channel widths (FIG. 4F).

Example 8: Delivery of mRNA to Jurkat and Primary Pan T Cells

To demonstrate the capability of our exemplary device to deliver mRNA, we transfected Jurkat and primary T cells with mRNA encoding GFP. Primary T cells from healthy donors were transfected four days after activation with CD3/CD28 antibodies. Both cell types were resuspended at a concentration of $5\times10^6$ cells/mL in low conductivity electroporation buffer containing GFP-encoding mRNA at either 20 μg/mL or 40 μg/mL, loaded into a syringe, and flowed into our electroporation flow cell as described in our methods. As cells transit under the electrode, the voltage temporal waveform was selected such that cells received three bipolar rectangular waveforms (FIG. 1E) on average during their transit time through the electric field (t=100 μs, f=100 Hz). This value was inferred from the average linear velocity, the volumetric flow rate, and the dimension of the electrode along the direction of flow. As a control, cells were collected at zero applied voltage.

Figures 6A, 6B:
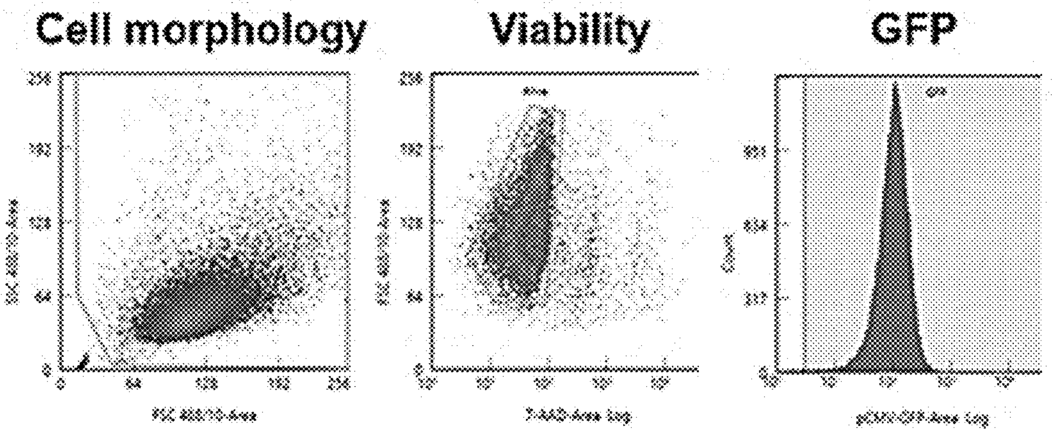
FIG. 6A-FIG. 6D: Delivery of mRNA encoding GFP to Jurkat and primary T cells.

To measure delivery performance, cells were analyzed 24-h post-transfection using flow cytometry (FIG. 6A-FIG. 6B). For each voltage condition, cell count, viability, and GFP expression were directly measured through successive gating as described in the methods. Viability for each voltage condition was calculated as the number of viable cells ($N_{viable}$), measured using a viability dye (7-AAD), divided by the number of total cells in that voltage condition, measured 24-h post-transfection ($N_{total}$) (Eqn. 1).

$$\text{Viability} = \frac{N_{viable}}{N_{total}} \qquad \text{Eqn. 1}$$

For primary T cells, a viability ratio was calculated because the initial viability of each T cell donor ranged from 83-92%, independent of electroporation. Viability ratio was calculated as the viability (calculated in Eqn. 1) divided by the viability of the zero-voltage control cells ($\text{Viability}_{zero\text{-}voltage\ control}$) (Eqn. 2). The viability of zero-voltage control cells is measured 24-h post-transfection from cells that flowed through the device without an applied electric field.

$$\text{Viability ratio} = \frac{\text{Viability}}{\text{Viability}_{zero-voltage\ control}} \qquad \text{Eqn. 2}$$

GFP expression was defined as the number of viable and expressing cells ($N_{expressing}$) divided by the number of viable cells (Eqn. 3).

$$GFP \text{ expression} = \frac{N_{expressing}}{N_{viable}} \qquad \text{Eqn. 3}$$

Since our measurement of viability does not account for cells that have been lost during electroporation (i.e. complete lysis), we also calculated relative yield as the total number of cells in each voltage condition ($N_{total}$) divided by the number of zero-voltage control cells ($N_{zero\text{-}voltage\ control}$) (Eqn. 4).

$$\text{Relative yield} = \frac{N_{total}}{N_{zero-voltage\ control}} \quad \text{Eqn. 4}$$

Since relative yield is measured from cell counts 24-h post-transfection, this measurement is influenced by variation in cell seeding, variation in proliferation rate, and cell lysis or loss during electroporation.

Figure 6C:
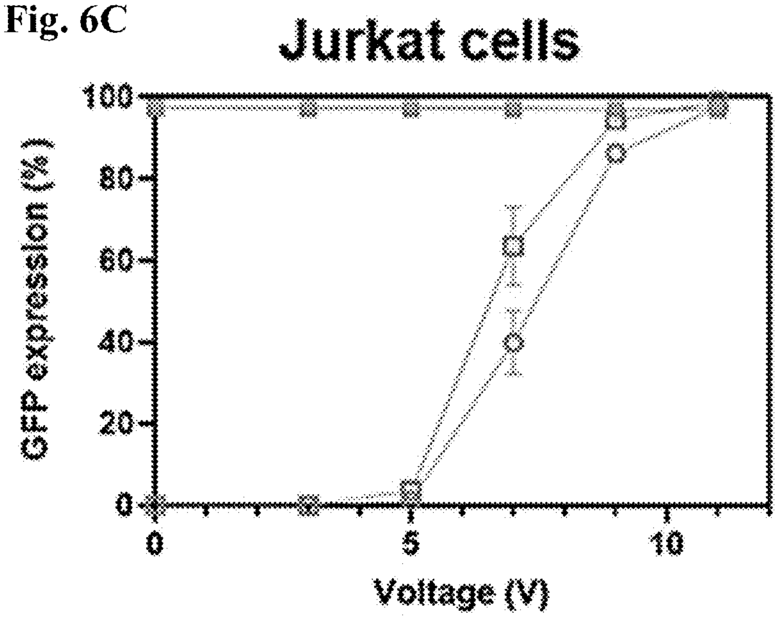
Figure 6D:
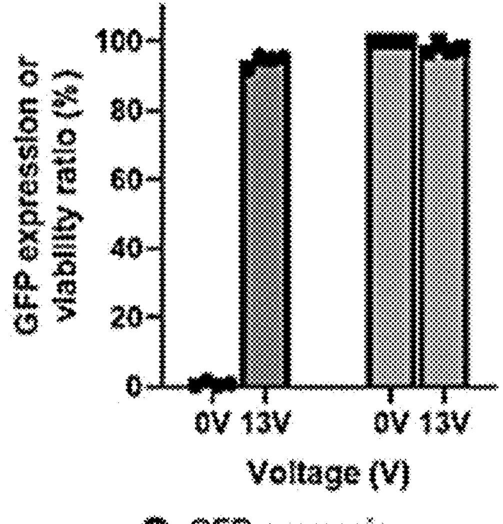
Figure 11B:
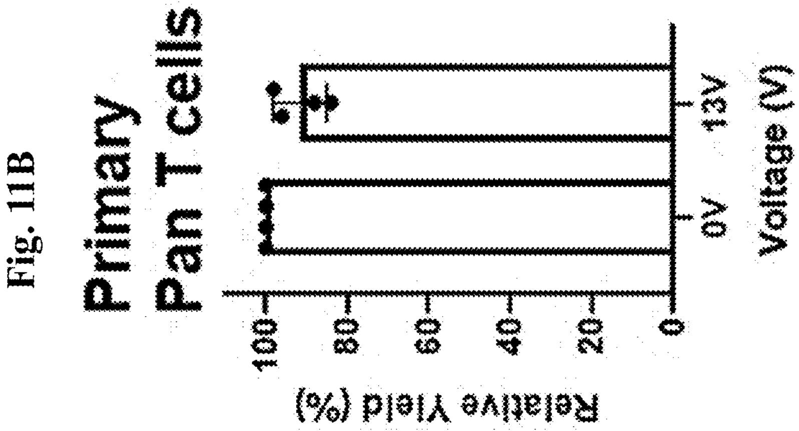
FIG. 11A-FIG. 11B: Delivery of mRNA encoding GFP to Jurkat and primary T cells (FIG. 11A) Impact of varying waveform voltage amplitude on relative yield during delivery of mRNA to Jurkat cells (N=3; n=3) or (FIG. 11B) primary T cells from four healthy donors (N=4; n=4). Data shown as mean±standard deviation.
Figure 11A:
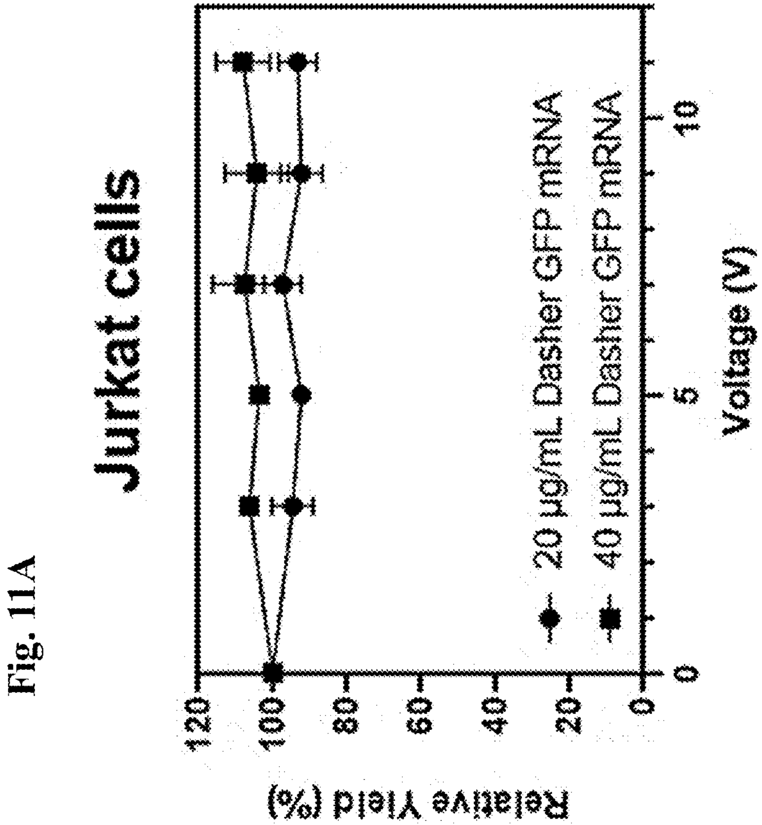

We tested delivery of mRNA to Jurkat cells using either 20 or 40 μg/mL of mRNA encoding GFP and waveform voltage amplitude ranging from 3V to 11V (FIG. 6C). As the waveform voltage amplitude increased, we observed a threshold effect in which GFP expression was absent below 5V, then increased until reaching a plateau value of ~97% at 11V. At all voltage amplitudes and mRNA concentrations tested, viability remained unchanged relative to zero-voltage controls while relative yield remained >90% (FIG. 6C, FIG. 11A). Notably, we observed 95%±1.8% GFP expression from primary T cells derived from four healthy donors, while the viability ratio and relative yield were 98%±1.4% and 92%±6.6%, respectively (FIG. 6D, FIG. 11B). As such, these data demonstrate the capability of our platform to deliver mRNA at high efficiency without impacting cell viability.

Example 9: Increasing Cell Processing Throughput for Clinical-Scale Volumes

Given that current autologous cell therapies require large volumes of engineered cells, we examined three methods easily available with our platform to increase cell processing throughput: 1) Proportionally increasing the flow channel's width and volumetric flow rate, 2) adjusting the time dependence of the voltage temporal waveform and fluid flow rate in a way such that the cells experience the same time-dependent electric field during passage between the electrodes in both cases, e.g., proportionally increasing the fluid flow rate and waveform frequency, and 3) increasing the cell concentration in the electroporation buffer.

Figures 12A, 12B, 12C:
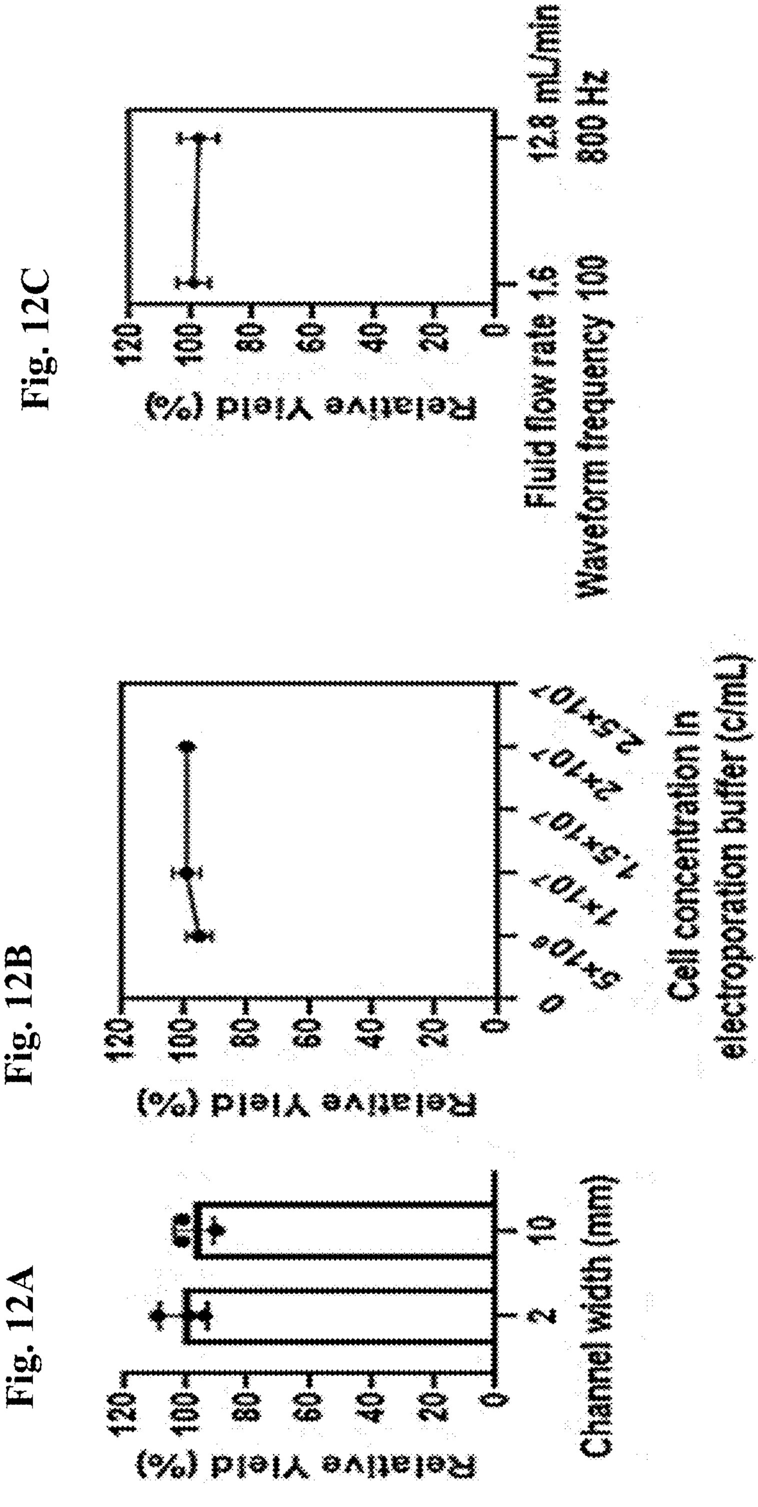
FIG. 12A-FIG. 12C: Increasing cell processing throughput for clinical-scale volumes.

Increasing the volumetric flow rate and channel width by the same factor leaves the average linear flow velocity of the cells under the electrode unchanged and thus does not impact the electrical or chemical environment of the cells. We increased the width of the channel from 2 mm, used in our optimization study, to 10 mm while proportionally increasing the volumetric flow rate from 320 μL/min to 1.6 mL/min (FIG. 7A-FIG. 7B). Jurkat cells were electroporated with mRNA encoding GFP (20 μg/mL) in both channels using a bipolar rectangular waveform (t=100 μs, f=100 Hz, V=13 V) at a concentration of $5\times10^6$ cells/mL as described previously. Notably, GFP expression, viability, and relative yield were roughly identical in the 2- and 10-mm channel while cell processing throughput increased by a factor of five from $1.6\times10^6$ cells/min to $8\times10^6$ cells/min (FIG. 7C, FIG. 12A). These results indicate that proportionally increasing the flow cell channel width and volumetric flow rate presents an easy method to seamlessly increase cell processing throughput.

We tested increasing the concentration of cells within the electroporation buffer as a method to increase cell processing throughput. Jurkat cells were electroporated with mRNA encoding GFP (20 μg/mL) using a bipolar rectangular waveform (t=100 μs, V=13 V, f=100 Hz) as described previously. We tested transfecting cells at a concentration of 5, 10, or $20\times10^6$ cells/mL and observed no differences in GFP expression, viability, or relative yield (FIG. 7D, FIG. 12B). As such, increasing the cell concentration during transfection offers another easy method to enhance cell processing throughput.

In addition to increasing the channel width or cell concentration, we also proportionally increased the volumetric flow rate and electrical waveform frequency to increase throughput. Jurkat cells were electroporated with mRNA encoding GFP (20 μg/mL) using a bipolar rectangular waveform (t=100 μs, V=13 V) at a concentration of $5\times10^6$ cells/mL as described previously. We tested increasing the waveform frequency from 100 Hz to 800 Hz with a proportional increase in volumetric flow rate from 1.6 mL/min to 12.8 mL/min. We observed no differences in GFP expression, viability, or relative yield (FIG. 7E, FIG. 12C). Importantly, proportionally increasing the waveform frequency and flow rate increased cell throughput from $8\times10^6$ cells/min to $64\times10^6$ cells/min. As such, this method can greatly increase cell processing throughput without changing the geometry of the flow channel.

Finally, we combined all of the aforementioned methods for increasing cell processing throughput in a single experiment to efficiently deliver mRNA encoding GFP to approximately 240 million Jurkat cells in a demonstration of a clinical-scale transfection. Jurkat cells were transfected with mRNA (20 μg/mL) using a bipolar rectangular waveform (t=100 μs, V=13 V, f=800 Hz) at a concentration of $20\times10^6$ cells/mL while flowing at 12.8 mL/min. At a processing speed of 256 million cells/min, delivery to 240 million cells took approximately 56 s. We sampled cells at various times during delivery and found GFP expression and viability to be consistent over time at 97%±0.12% and 96%±0.39%, respectively (FIG. 7F). Relative yield was more variable at 73%±5%. Overall, the variety of methods available to our device to increase cell processing throughput provide highly efficient delivery at the speeds required for clinical-scale delivery.

Example 10: Demonstration of High-Performance Plasmid DNA Delivery to Jurkat and Primary Pan T Cells To demonstrate delivery of plasmid DNA, we used bipolar rectangular waveforms with a fixed duration (t=100 μs) and tested the impact of varying three parameters with both Jurkat and primary pan T cells: waveform voltage amplitude (V), waveform frequency (f), and plasmid concentration.

Figures 14E, 14F:
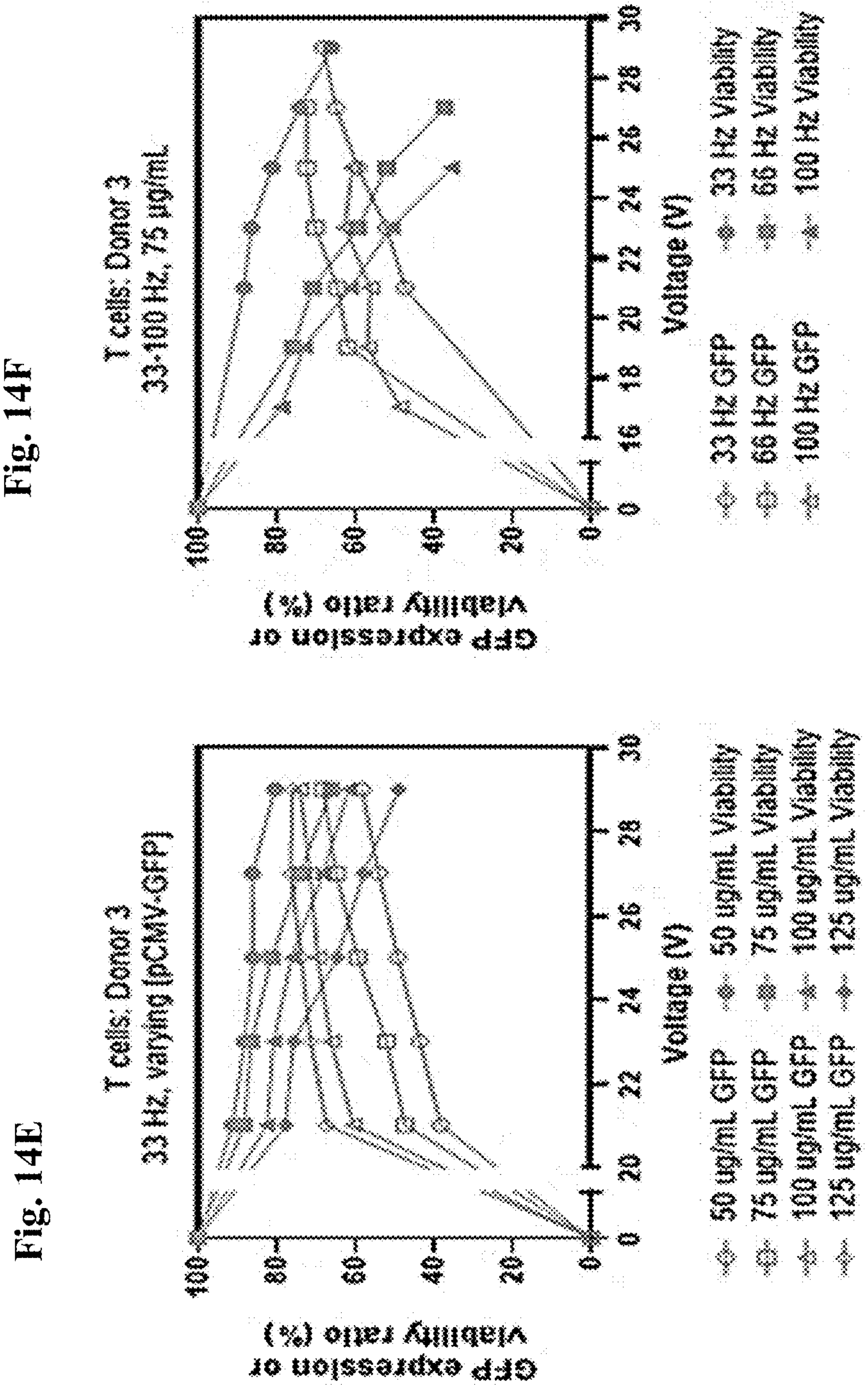
Figures 15A, 15B:
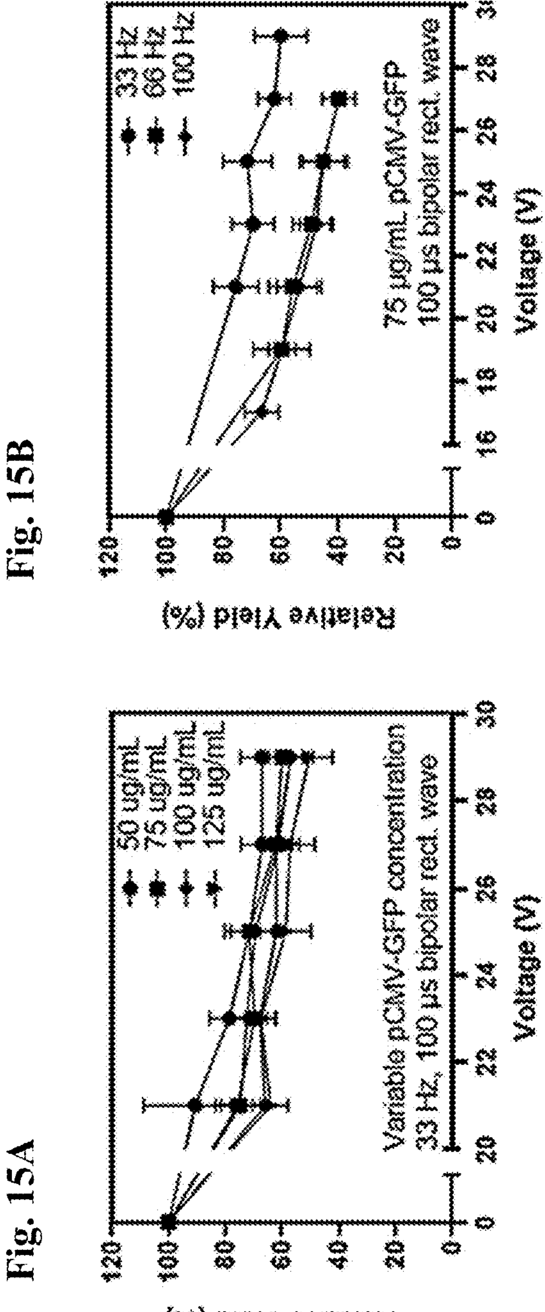
FIG. 15A-FIG. 15B: Relative yield data for delivering plasmid DNA primary T cells from four healthy donors.

Jurkat and primary pan T cells were prepared as described previously. For both Jurkat and primary T cells, increasing the concentration of GFP-encoding plasmid DNA resulted in increased GFP expression, decreased viability, and decreased relative yield (FIG. 8A-FIG. 8B, FIG. 13A-FIG. 13B). Interestingly, increasing the plasmid concentration had diminishing returns with smaller gains in GFP expression as plasmid concentration increased. Similarly, increasing the waveform frequency also increased GFP expression with significant diminishing returns while decreasing viability and relative yield (FIG. 8C-FIG. 8D, FIG. 13C-FIG. 13D). We tested three waveform frequency values that correspond to cells receiving on average 1 (33 Hz), 2 (66 Hz), or 3 (100 Hz) waveforms per transit time under the electrode. The volumetric flow rate was kept constant in all cases. In general, there was a large increase in GFP expression from 33 Hz to 66 Hz with almost no further increase from 66 Hz to 100 Hz. Jurkat cells exhibited reproducible performance over three independent experiments with standard deviation values ranging from 1-4% for GFP expression and 1-5% for viability. Primary T cells exhibited significant donor to donor variation (FIG. 14 and FIG. 15). Overall, by varying three parameters, we could tune plasmid expression and viability within a broad range of values for both cell types.

Example 11: Delivery of an Arbitrary Electrical Waveform

Figures 9A, 9B, 9C:
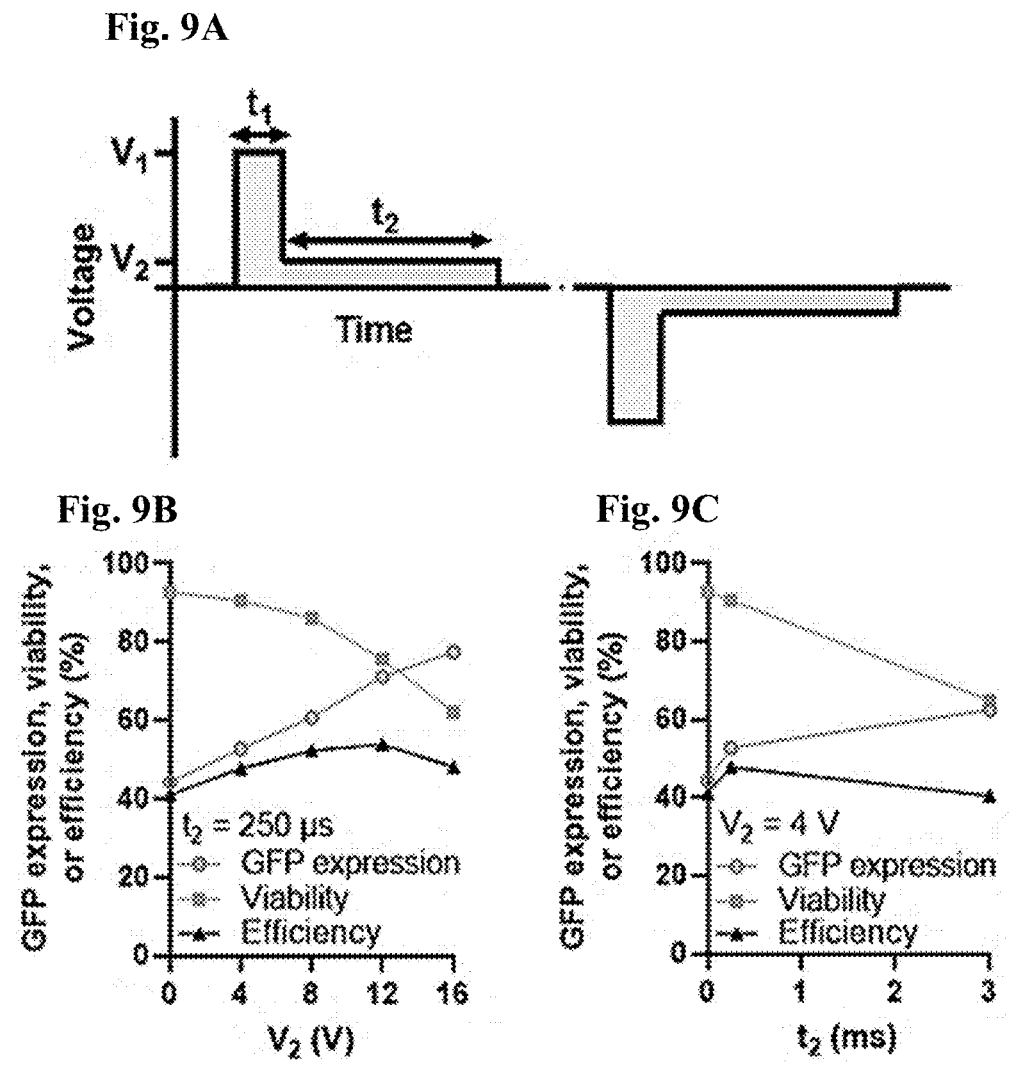

To demonstrate the flexibility of our device, we delivered plasmid DNA encoding GFP to Jurkat cells using an arbitrary waveform. We selected a dual level waveform characterized by a short-duration, high-amplitude segment ($V_1$, $t_1$) thought to nucleate pores followed by a longer-duration, low-amplitude segment ($V_2$, $t_2$) thought to grow the pores and electrophoretically drive charged cargo, such as DNA, into the cells (FIG. 9A). Dual level waveforms may balance plasmid DNA expression with cell viability. To demonstrate our system's capabilities, we selected f=66 Hz, $V_1$=21 V, and $t_1$=75 μs and measured the impact of varying $V_2$ or $t_2$ of the longer-duration, low-amplitude segment (FIG. 9A).

Figure 16B:
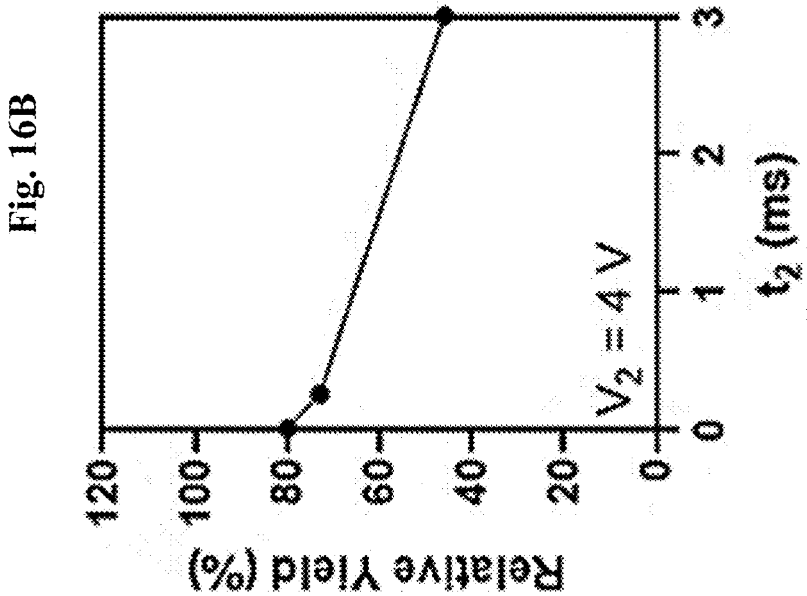
FIG. 16A-FIG. 16B: Relative yield data from delivery of an arbitrary electrical waveform to Jurkat cells.
Figure 16A:
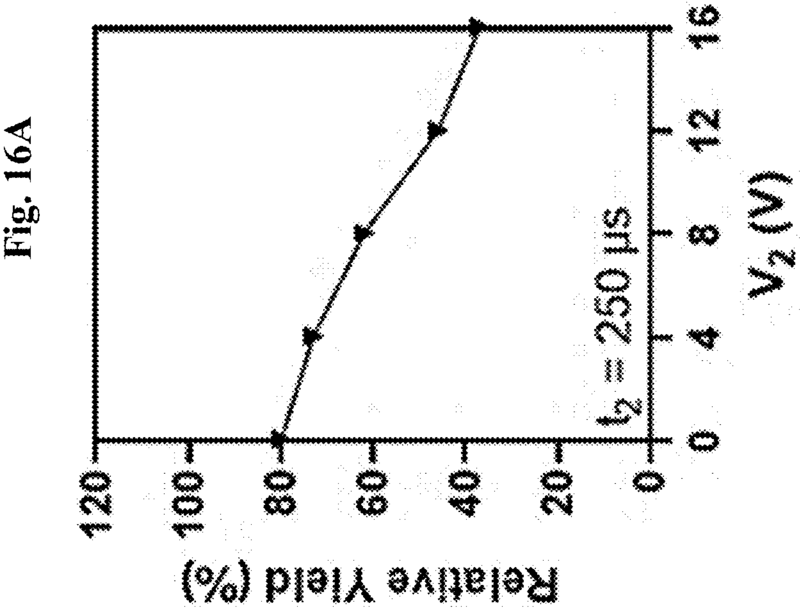

Jurkat cells were prepared as described previously. Efficiency of transfection was defined as the product of GFP expression and viability and calculated as a single metric to compare waveform performance. As either $V_2$ or $t_2$ increased, GFP expression increased while viability and relative yield decreased (FIG. 9C-FIG. 9D, FIG. 16). Notably, our metric for waveform performance, efficiency, exhibited a peak value at intermediate values of $V_2$ and $t_2$, demonstrating how a dual voltage level waveform can favorably balance GFP expression and viability. Overall, these data demonstrate the capabilities of our device to deliver an arbitrary voltage waveform and how this capability could provide advantages for improving the electroporation performance of plasmid DNA.

Example 12: Delivery of CRISPR/Cas9 RNPs Targeting TRAC

Figure 10:
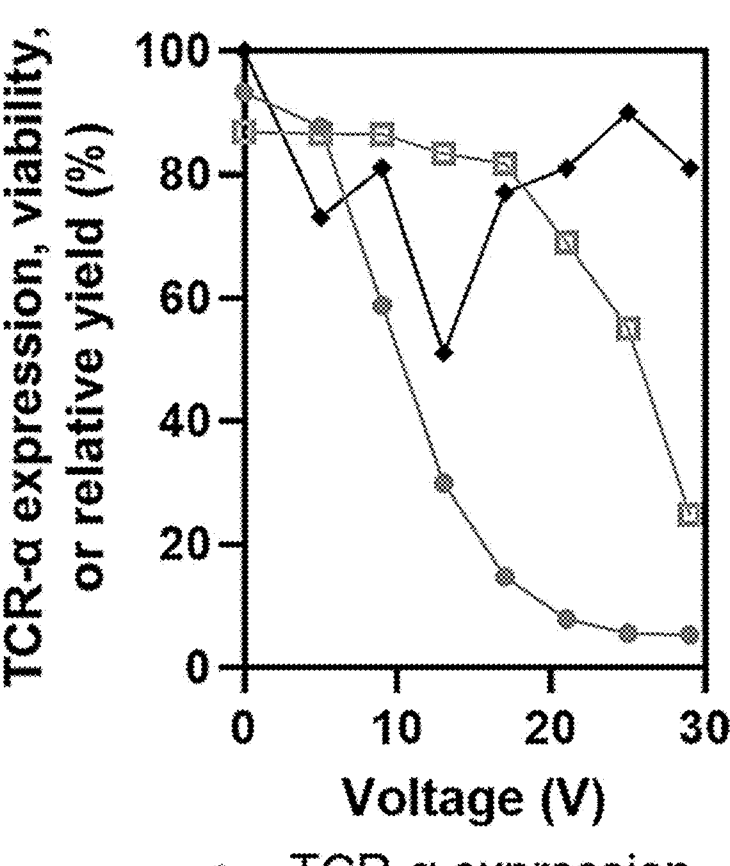
FIG. 10: Delivery of CRISPR/Cas9 RNPs targeting TRAC. Plot of TCR-α expression, viability, or relative yield as a function of applied voltage amplitude, measured 72-h after primary T cells were transfected with CRISPR/Cas9 RNPs targeting TRAC.

To demonstrate our capabilities to deliver cargo beyond GFP, we next turned to the CRISPR-Cas9 system. We chose to target the TRAC locus, which encodes for TCR-α, because knocking out TCR-α expression is being studied as a method of graft versus host disease (GVHD)-avoidance for engineering allogenic CAR T cells. Primary T cells from healthy donors were transfected four days post-activation with CD3/CD28 antibodies using bipolar rectangular waveforms (t=100 μs, f=100 Hz, V=5-29 V) and using CRISPR-Cas9 RNPs (1 μM). TCR-α expression was measured 72-h post-transfection using anti-human TCR-α antibody and flow cytometry. As the waveform voltage amplitude increased, TCR-α expression dropped precipitously from 93% to a plateau value of ~5% (FIG. 10A). Viability also decreased with increasing voltage with minimal changes up to 17 V which yielded 15% TCR-α expression and 82% viability. After 17 V, viability dropped precipitously. Overall, these data suggest our device has the capability to perform CRISPR/Cas9 genetic engineering which is a promising technique for advancing cell therapies beyond the currently approved autologous cell therapies.

Electroporation represents a promising approach to replace virus-based methods to manufacture cellular therapies, but traditional cuvette-style methods remain limited by process variability, difficult optimization, and low throughput. Here, we present a novel electroporation platform that bypasses these limitations through incorporation of a planar flow cell coupled with automated experimentation. As demonstrated by our performance data, we can rapidly explore a large parameter-space to derive conditions for efficient delivery of different molecular cargo to cells. Importantly, we also demonstrated how optimizations performed using small volumes can be directly translated into large-scale transfections for cell manufacturing. Together, these innovations demonstrate the potential for our device to address unmet needs for non-viral engineering of T cells for cell manufacturing.

We observed high efficiency delivery of mRNA encoding GFP to Jurkat and primary T cells (>98% for Jurkat, >95% primary T cells) without significantly impacting cell viability or relative yield from our device. Our mRNA delivery performance exceeds values reported from cuvette-style electroporation devices and meets or exceeds the performance metrics from other microfluidic, non-viral transfection approaches. Importantly, we were able to seamlessly scale mRNA delivery through increasing the concentration of cells in the electroporation buffer, the width of the channel, the flow rate, and the voltage temporal waveform. The combination of these scaling methods enabled us to increase throughput up to 256 million cells/min using a channel width of 10 mm, a width that can be further expanded. Overall, our results indicate that increasing the width of our channel and using demonstrated flow, chemical, and electrical conditions that we can meet the required cell quantities for cellular therapies which often require greater than 1 billion cells.

Current autologous T cell therapies require long and costly manufacturing which restrains their large-scale clinical use. Universal "off-the-shelf" or allogenic CAR-T cells from healthy donors could bypass these limitations but allogenic CAR-T cells may be swiftly eliminated by the host immune system and may also cause life-threatening graft-versus-host disease (GVHD). Disruption of the gene encoding for TCR-α (TRAC) has been reported elsewhere as a method to reduce risk of GVHD and is currently being investigated in preclinical studies and clinical trials. Here, we demonstrate delivery of CRISPR-Cas9 RNPs to efficiently knock-out primary T cell expression of TCR-α to show how our device could be used for the manufacturing of next-generation, allogenic CAR-T cells.

The thin slab geometry of our flow cell is the innovation that provides many of our device's strengths. The thin channel height (50-100 μm) enables uniform electric fields that yield highly reproducible electroporation. We report standard deviations for GFP expression and viability routinely below 5%. Additionally, thin channel height permits us to reach the necessary electric field strength for electroporation with relatively low voltage amplitude (5-30 V) compared to traditional commercial systems. For instance, we observed that mRNA expression began at a voltage amplitude of 5V and plateaued around 11V. As such, our device can avoid incorporation of expensive, complex electronics required for high voltages.

The width of our device provides a simple mechanism to scale cell throughput without changing the electric field experienced by the cells. Here, we demonstrated our scaling feature by increasing channel width and experimental throughput by a factor of five with identical performance using an identical electrical waveform. This ability to determine transfection parameters using small volumes of cells and reagents and directly translate optimized parameters for large volume, clinical-scale delivery is a key advantage of our platform. Notably, although there are multiple other continuous-flow platforms capable of non-viral transfection of primary T cells, none provide the seamless scaling capability inherent to our variable-width thin slab geometry.

For example, mechanoporation approaches achieve delivery through physical constrictions that temporarily open the plasma membrane. However, scale-up requires parallelization because the flow rate and channel dimensions influence the transfection parameters. Specifically, changing the dimensions of the channel or the fluid flow velocities in the standard mechanoporation approaches would change the hydrodynamic forces on the cells and change the pore formation. Therefore, to increase the throughput in these approaches, multiple devices are used rather than increasing the dimensions or flow rate in a device. For example, if the mechanoporation method uses a tube-like devices many tubes would typically be used to multiply the throughput of the total system, which increases the fluid control complexity of the system.

The ability to deliver an arbitrary time varying electric field provides a nearly unlimited parameter-space for optimizing performance. We utilized bipolar waveforms to limit the effect of electrochemical reactions that occur at the electrode and limit charge accumulation at the electrodes. Flexibility in design of the waveform provides the capability to tailor delivery to the particular cargo. For instance, there is evidence that electrophoretic transfer contributes to plasmid DNA delivery and has led to the emergence of waveforms with dual voltages to improve delivery performance. Indeed, we demonstrate that a dual voltage waveform can improve the efficiency of delivery of plasmid DNA to Jurkat cells. We also evaluated the impact of varying the voltage waveform amplitude as well as the average number of waveform cycles experienced by the flowing cells. Plasmid concentration, cell concentrations, and other process parameters were also varied. Increasing the cargo concentration or increasing the voltage waveform amplitude tended to increased transfection efficiency and reduce viability.

In summary, our results demonstrate the capabilities of our novel electroporation platform for high efficiency and high viability delivery of multiple cargo to Jurkat and primary T cells. The innovations afforded by our microfluidic platform and their superior performance make it a promising system for non-viral cellular reprogramming for cell therapies.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

REFERENCES CITED

1. Porter D, Levine B, Kalos M, Bagg A, June C H. Chimeric Antigen Receptor-Modified T Cells in Chronic Lymphoid Leukemia. N Engl J Med. 2011; 365:725-33.
2. Grupp S, Kalos M, Barrett D, Aplenc R, Porter D, Rheingold S, et al. Chimeric Antigen Receptor-Modified T Cells for Acute Lymphoid Leukemia. N Engl J Med. 2013; 368:1509-18.
3. Maus M V, Fraietta J A, Levine B L, Kalos M, Zhao Y, June C H. Adoptive Immunotherapy for Cancer or Viruses. Annu Rev Immunol. 2014; 32:189-225.
4. Mount N M, Ward S J, Kefalas P, Hyllner J, Mount N M. Cell-based therapy technology classifications and translational challenges. Philos Trans B. 2015; 370(20150017).
5. Buzhor E, Leshansky L, Blumethnal J, Barash H, Warshawsky D, Mazor Y, et al. Cell-based therapy approaches: the hope for incurable diseases. Regen Med. 2014; 9(5):14-35.
6. Cerrano M, Ruella M, Perales M, Vitale C, Faraci D G, Giaccone L, et al. The Advent of CAR T-Cell Therapy for Lymphoproliferative Neoplasms: Integrating Research Into Clinical Practice. Front Immunol. 2020; 11:1-25.
7. Levine B L, Miskin J, Wonnacott K, Keir C. Global Manufacturing of CAR T Cell Therapy. Mol Ther—Methods Clin Dev [Internet]. 2017; 4(March):92-101. Available from: http://dx.doi.org/10.1016/j.omtm.2016.12.006
8. Bozza M, De Roia A, Correia M P, Berger A, Tuch A, Schmidt A, et al. A nonviral, nonintegrating DNA nanovector platform for the safe, rapid, and persistent manufacture of recombinant T cells. Sci Adv. 2021; 7(16):1-14.
9. Sun S, Hao H, Yang G, Zhang Y, Fu Y. Immunotherapy with CAR-Modified T Cells: Toxicities and Overcoming Strategies. J Immunol Res. 2018; 2018:1-10.
10. Ivics Z, Lee D A, Champlin R E, Jin Z, Maiti S, Huls H, et al. The hyperactive Sleeping Beauty transposase SB100X improves the genetic modification of T cells to express a chimeric antigen receptor. Gene Ther. 2011; 18(March):849-56.
11. Roth T L, Puig-saus C, Yu R, Shifrut E, Carnevale J, Li J, et al. Reprogramming human T cell function and specificity with non-viral genome targeting. Nature [Internet]. 2018; 559:405-9. Available from: http://dx.doi.org/10.1038/s41586-018-0326-5
12. Schober K, Müller TR, Gokmen F, Grassmann S, Effenberger M, Poltorak M, et al. Orthotopic replacement of T-cell receptor α- and β-chains with preservation of near-physiological T-cell function. Nat Biomed Eng [Internet]. 2019; 3:974-84. Available from: http://dx.doi.org/10.1038/s41551-019-0409-0
13. Kotowski M, Sharma S. CRISPR-Based Editing Techniques for Genetic Manipulation of Primary T Cells. methods Protoc. 2020; 3(79).
14. Rafiq S, Hackett C S, Brentjens R J. Engineering strategies to overcome the current roadblocks in CART cell therapy. Nat Rev Clin Oncol [Internet]. 2020; 17(March):147-67. Available from: http://dx.doi.org/10.1038/s41571-019-0297-y
15. Liu X, Jiang S, Fang C, Li H, Zhang X, Zhang F, et al. Novel T cells with improved in vivo anti-tumor activity generated by RNA electroporation. Protein Cell. 2017; 8(7):514-26.
16. Prommersberger S, Reiser M, Beckmann J, Danhof S, Amberger M, Quade-Lyssy P, et al. CARAMBA: a first-in-human clinical trial with SLAMF7 CAR-T cells prepared by virus-free Sleeping Beauty gene transfer to treat multiple myeloma. Gene Ther [Internet]. 2021; 28(9): 560-71. Available from: http://dx.doi.org/10.1038/s41434-021-00254-w
17. Morita D, Nishio N, Saito S, Tanaka M, KawashimaN, Okuno Y, et al. Enhanced Expression of Anti-CD19 Chimeric Antigen Receptor in piggyBac Transposon-Engineered T Cells. Mol Ther—Methods Clin Dev [Internet]. 2018; 8:131-40. Available from: https://doi.org/10.1016/j.omtm.2017.12.003
18. Weaver J C, Chizmadzhev Y A. Theory of electroporation: A review. Bioelectrochemistry Bioenerg. 1996; 41:135-60.

19. Teissie J, Golzio M, Rols M P. Mechanisms of cell membrane electropermeabilization: A minireview of our present (lack of?) knowledge. Biochim Biophys Acta. 2005; 1724:270-80.

20. Lee W G, Demirci U, Khademhosseini A. Microscale electroporation: challenges and perspectives for clinical applications. Integr Biol. 2009; 1(3):242-51.

21. Li L H, Shivakumar R, Feller S, Allen C, Weiss J M, Dzekunov S, et al. Highly efficient, large volume flow electroporation. Technol Cancer Res Treat. 2002; 1(5): 341-9.

22. Vormittag P, Gunn R, Ghorashian S, Veraitch F S. A guide to manufacturing CAR T cell therapies. Curr Opin Biotechnol [Internet]. 2018; 53:164-81. Available from: http://dx.doi.org/10.1016/j.copbio.2018.01.025

23. Kanduser M, Miklavcic D, Pavlin M. Mechanisms involved in gene electrotransfer using high- and low-voltage pulses—An in vitro study. Bioelectrochemistry. 2009; 74(2):265-71.

24. Sukharev S I, Klenchin V A, Serov S M, Chernomordik L V., Chizmadzhev Yu A. Electroporation and electrophoretic DNA transfer into cells. The effect of DNA interaction with electropores. Biophys J. 1992; 63(5):1320-7.

25. Wong L, Brampton C, Woo D, Dreskin E. Optimizing Electroporation Conditions for High-Efficiency mRNA Transfection of CD8+T Cells with the Gene Pulser Xcell Electroporation System mRNA using the Gene Pulser Xcell Electroporation System and Gene Pulser Electroporation. 2020;

26. Lissandrello C A, Santos J A, Hsi P, Welch M, Mott V L, Kim E S, et al. High-throughput continuous-flow microfluidic electroporation of mRNA into primary human T cells for applications in cellular therapy manufacturing. Sci Rep [Internet]. 2020; 10:1-16. Available from: https://doi.org/10.1038/s41598-020-73755-0

27. Sido J M, Hemphill J B, McCormack R N, Beighley R D, Grant B F, Buie C R, et al. Electro-mechanical transfection for non-viral primary immune cell engineering. bioRxiv [Internet]. 2021; 2021.10.26.465897. Available from: http://biorxiv.org/content/early/2021/10/28/2021.10.26.465897.abstract 28. Loo J, Sicher I, Goff A, Kim O, Clary N, Alexeev A, et al. Microfluidic transfection of mRNA into human primary lymphocytes and hematopoietic stem and progenitor cells using ultra-fast physical deformations. Sci Rep [Internet]. 2021; 11(1):1-11. Available from: https://doi.org/10.1038/s41598-021-00893-4

29. Somerville R P T, Devillier L, Parkhurst M R, Rosenberg S A, Dudley M E. Clinical scale rapid expansion of lymphocytes for adoptive cell transfer therapy in the WAVE® bioreactor. J Transl Med [Internet]. 2012; 10(1): 69. Available from: http://www.translational-medicine-.com/content/10/1/69

30. Depil S, Duchateau P, Grupp S A, Mufti G, Poirot L. 'Off-the-shelf' allogeneic CAR T cells: development and challenges. Vol. 19, Nature Reviews Drug Discovery. Nature Research; 2020. p. 185-99.

31. Razeghian E, Nasution M K M, Rahman H S, Gardanova Z R, Abdelbasset W K, Aravindhan S, et al. A deep insight into CRISPR/Cas9 application in CAR-T cell-based tumor immunotherapies. Stem Cell Res Ther. 2021; 12(1): 1-17.

32. Stadtmauer E A, Fraietta J A, Davis M M, Cohen A D, Weber K L, Lancaster E, et al. CRISPR-engineered T cells in patients with refractory cancer. Science (80-). 2020 Feb. 28; 367(6481).

33. Eyquem J, Mansilla-Soto J, Giavridis T, Van Der Stegen S J C, Hamieh M, Cunanan K M, et al. Targeting a CAR to the TRAC locus with CRISPR/Cas9 enhances tumour rejection. Nature [Internet]. 2017; 543(7643):113-7. Available from: http://dx.doi.org/10.1038/nature21405

34. Osborn M J, Webber B R, Knipping F, Lonetree C L, Tennis N, DeFeo A P, et al. Evaluation of TCR gene editing achieved by TALENs, CRISPR/Cas9, and megaTAL nucleases. Mol Ther [Internet]. 2016; 24(3):570-81. Available from: http://dx.doi.org/10.1038/mt.2015.197

35. Lee J, Sharei A, Sim W Y, Adamo A, Langer R, Jensen K F, et al. Nonendocytic delivery of functional engineered nanoparticles into the cytoplasm of live cells using a novel, high-throughput microfluidic device. Nano Lett. 2012; 12(12):6322-7.

36. Sharei A, Zoldan J, Adamo A, Sim W Y, Cho N, Jackson E, et al. A vector-free microfluidic platform for intracellular delivery. Proc Natl Acad Sci USA. 2013; 110(6): 2082-7.

37. Lesueur L L, Mir L M, André F M. Overcoming the Specific Toxicity of Large Plasmids: Electrotransfer in Primary Cells In Vitro. Mol Ther—Nucleic Acids [Internet]. 2016; 5 (December 2015):e291. Available from: http://dx.doi.org/10.1038/mtna.2016.4

38. Harris E, Elmer J J. Optimization of electroporation and other non-viral gene delivery strategies for T cells. Biotechnol Prog. 2021; 37(1).

39. Stewart M P, Langer R, Jensen K F. Intracellular delivery by membrane disruption: Mechanisms, strategies, and concepts. Chem Rev. 2018; 118(16):7409-531.

40. Hyder I, Eghbalsaied S, Kues W A. Systematic optimization of square-wave electroporation conditions for bovine primary fibroblasts. BMC Mol Cell Biol. 2020; 21:1-8.

41. Kotnik T, Pucihar G, Reberšek M, Miklavčič D, Mir L M. Role of pulse shape in cell membrane electropermeabilization. Biochim Biophys Acta—Biomembr. 2003; 1614(2):193-200.

INCORPORATION BY REFERENCE

All U.S. patents, and U.S. and PCT patent application publications mentioned herein are hereby incorporated by reference in their entirety as if each individual patent or patent application publication was specifically and individually indicated to be incorporated by reference. In case of conflict, the present application, including any definitions herein, will control.

EQUIVALENTS

Those skilled in the art will recognize or be able to ascertain using no more than routine experimentation many equivalents to the specific embodiments of the present invention described herein. Such equivalents are intended to be encompassed by the following claims.

The articles "a" and "an" are used herein to refer to one or to more than one (i.e. to at least one) of the grammatical object of the article. By way of example, "an element" means one element or more than one element.

What is claimed is:

1. A method of electroporation using a microfluidic device, the method comprising:

flowing a liquid through a channel in the microfluidic device in a flow direction, the fluid including a plurality of cells and molecules, wherein the channel comprises a channel height (H) and a channel width (W), the ratio of the channel height to the channel width being less than about 0.1;

generating a time-dependent electric field across the channel and perpendicular to the flow direction using electrodes arranged transverse to the direction of flow, wherein a polarity of the time-dependent electric field is configured to alternate as a function of time, and wherein a waveform of the time-dependent electric field comprises a series of alternating positive and negative peaks; and coordinating a flow speed of the liquid through the channel and a waveform of the time-dependent voltage applied to the electrodes to generate the time-dependent electric field such that the molecules are moved into the plurality of cells after being subject to the time-dependent electric field, wherein the voltage wave form comprises a periodic bipolar waveform with alternating segments of symmetric reversed polarity, each of the alternating segments having a first segment portion followed by a second segment portion, the first segment portion having a shorter duration and a higher amplitude relative to the second segment portion.

2. The method of claim 1, further comprising selecting parameters for the electroporation, the parameters including:

a volume (V) of the liquid to be electroporated; and a time (T) to perform the electroporation in.

3. The method of claim 2, where in the flow speed is a fluid flow speed(S), and a relationship exists where H×W×S equals a throughput of the electroporation, and wherein the throughput is defined as the volume of the liquid (V) to be electroporated per the time (T).

4. The method of claim 3, wherein the channel width and the fluid flow speed are proportionally modified by a same factor to maintain a same average linear flow velocity of the plurality of cells.

5. The method of claim 1, wherein the microfluidic device comprises 2-10 electrodes.

6. The method of claim 1, wherein the channel comprises multiple pairs of electrodes to apply the time-dependent electric field.

7. The method of claim 1, wherein the microfluidic device comprises one inlet.

8. The method of claim 1, wherein the microfluidic device comprises at least two inlets.

9. The method of claim 1, wherein the channel comprises one or more electrodes disposed on each of opposite sides of the channel, wherein a space is defined between the one or more electrodes.

10. The method of claim 9, wherein the plurality of cells pass through the space in a single layer.

11. The method of claim 1, wherein the plurality of cells are selected from the group consisting of lymphocytes, T cells, primary T cells, CHO, Hela, CD8+, CD4+, CD3+, PBMC, Huh-7, Renca, NIH 3T3, Primary Fibroblasts, hMSC, K562, Vero, HEK 293, A549, B16, BHK-21, C2C12, C6, CaCo-2, CAP-T, COS-1, Cos-7, CV-1, DLD-1, H1299, Hep G2, HOS, Jurkat, L5278Y, LNCaP, MCF7, MDA-MB-231, MDCK, Mesenchymal Stem Cells, Min-6, Neuro2a, NIH3T3L1, NSO, Panc-1, PC12, PC-3, RBL, RLE, SF21, SF9, SH-SY5Y, SK-MES-1, SK-N-SH, SL3, SW403, THP-1, U205, U937, and combinations thereof.

12. The method of claim 1, wherein the microfluidic device further comprises a flow sensor configured to measure the flow speed and communicate with a feedback control mechanism.

13. The method of claim 1, wherein the channel width is constant across a length of the channel.

14. The method of claim 1, wherein the channel width varies across a length of the channel.

15. The method of claim 1, wherein the molecules are selected from the group consisting of DNA, RNA, protein, peptide, peptidomimetic, beads, dyes, or combinations thereof.

16. The method of claim 1, wherein the molecules comprise mRNA, and the mRNA is electroporated into at least a portion of the plurality of cells with a transfection efficiency of greater than 95% and less than 2% in loss of cell viability.

17. The method of claim 1, wherein the molecules are charged.

* * * * *